US009549708B2

(12) United States Patent
Mercanzini et al.

(10) Patent No.: US 9,549,708 B2
(45) Date of Patent: Jan. 24, 2017

(54) DEVICE FOR INTERACTING WITH NEUROLOGICAL TISSUE AND METHODS OF MAKING AND USING THE SAME

(75) Inventors: André Mercanzini, Renens (CH); Philippe Renaud, Preverenges (CH); Claudio Pollo, Lausanne (CH)

(73) Assignee: ECOLE POLYTECHNIQUE FEDERALE DE LAUSANNE, Lausanne (CH)

( * ) Notice: Subject to any disclaimer, the term of this patent is extended or adjusted under 35 U.S.C. 154(b) by 546 days.

(21) Appl. No.: 13/638,435

(22) PCT Filed: Mar. 31, 2011

(86) PCT No.: PCT/EP2011/055045
§ 371 (c)(1),
(2), (4) Date: Dec. 14, 2012

(87) PCT Pub. No.: WO2011/121089
PCT Pub. Date: Oct. 6, 2011

(65) Prior Publication Data
US 2013/0085361 A1    Apr. 4, 2013
Related U.S. Application Data

(60) Provisional application No. 61/320,089, filed on Apr. 1, 2010.

(51) Int. Cl.
*A61N 1/00* (2006.01)
*A61B 5/04* (2006.01)
(Continued)

(52) U.S. Cl.
CPC . *A61B 6/12* (2013.01); *A61B 5/04* (2013.01); *A61B 5/04001* (2013.01);
(Continued)

(58) Field of Classification Search
CPC .. A61N 1/3686; A61N 1/0551; A61N 1/0534; A61N 1/0529; A61N 1/0531; A61N 1/36082; A61N 1/36017; A61N 1/048; A61B 5/4893
(Continued)

(56) References Cited

U.S. PATENT DOCUMENTS 4,245,645 A    1/1981    Arseneault et al.
4,550,733 A    11/1985    Liss et al.
(Continued)

FOREIGN PATENT DOCUMENTS

EP    0 677 743    10/1995
EP    0 743 839    11/1996
(Continued)

OTHER PUBLICATIONS

US 8,388,533, 03/2013, Hafezi et al. (withdrawn)
(Continued)

*Primary Examiner* — Joseph Stoklosa
*Assistant Examiner* — Brian M Antiskay
(74) *Attorney, Agent, or Firm* — Foley & Lardner LLP; James De Vellis

(57) ABSTRACT

Described herein are microelectrode array devices, and methods of fabrication, assembly and use of the same, to provide highly localized neural recording and/or neural stimulation to a neurological target. The device includes multiple microelectrode elements arranged protruding shafts. The protruding shafts are enclosed within an elongated probe shaft, and can be expanded from their enclosure. The microelectrode elements, and elongated probe shafts, are dimensioned in order to target small volumes of neurons located within the nervous system, such as in the deep brain region. Beneficially, the probe can be used to quickly identify the location of a neurological target, and remain implanted for long-term monitoring and/or stimulation.

44 Claims, 33 Drawing Sheets

(51) Int. Cl.
*A61B 6/12* (2006.01)
*A61B 5/053* (2006.01)
*A61B 5/00* (2006.01)
*A61N 1/05* (2006.01)
*A61B 6/00* (2006.01)

(52) U.S. Cl.
CPC .......... *A61B 5/0536* (2013.01); *A61B 5/4041* (2013.01); *A61B 5/4893* (2013.01); *A61B 5/685* (2013.01); *A61B 5/6868* (2013.01); *A61B 5/6877* (2013.01); *A61B 6/501* (2013.01); *A61B 6/506* (2013.01); *A61N 1/0531* (2013.01); *A61N 1/0534* (2013.01); *A61N 1/0551* (2013.01); *A61B 2562/0209* (2013.01); *A61B 2562/046* (2013.01); *A61B 2562/125* (2013.01)

(58) Field of Classification Search
USPC ................ 600/372–374, 377–378, 544–545; 607/115–119, 122–123
See application file for complete search history.

(56) References Cited

U.S. PATENT DOCUMENTS

| | | |
|---|---|---|
| 4,837,049 A | 6/1989 | Byers et al. |
| 4,917,093 A | 4/1990 | Dufresne et al. |
| 4,928,297 A | 5/1990 | Tsutsui et al. |
| 4,969,468 A | 11/1990 | Byers et al. |
| 4,989,617 A | 2/1991 | Memberg et al. |
| 5,215,088 A | 6/1993 | Normann et al. |
| 5,391,250 A | 2/1995 | Cheney et al. |
| 5,400,784 A | 3/1995 | Durand et al. |
| 5,419,777 A | 5/1995 | Hofling |
| 5,496,369 A | 3/1996 | Howard, III |
| 5,524,338 A * | 6/1996 | Martyniuk .............. A61F 11/04 29/825 |
| 5,628,317 A | 5/1997 | Starkebaum et al. |
| 5,643,330 A | 7/1997 | Holsheimer et al. |
| 5,679,355 A | 10/1997 | Alexander et al. |
| 5,683,422 A | 11/1997 | Rise |
| 5,697,651 A | 12/1997 | Fernandes |
| 5,697,975 A | 12/1997 | Howard et al. |
| 5,702,429 A | 12/1997 | King |
| 5,713,922 A | 2/1998 | King |
| 5,713,923 A | 2/1998 | Ward et al. |
| 5,716,377 A | 2/1998 | Rise et al. |
| 5,727,552 A | 3/1998 | Ryan |
| 5,752,979 A | 5/1998 | Benabid |
| 5,755,759 A | 5/1998 | Cogan |
| 5,782,798 A | 7/1998 | Rise |
| 5,792,186 A | 8/1998 | Rise |
| 5,797,970 A | 8/1998 | Pouvreau |
| 5,800,474 A | 9/1998 | Benabid et al. |
| 5,800,535 A | 9/1998 | Howard, III |
| 5,814,092 A | 9/1998 | King |
| 5,824,029 A | 10/1998 | Weijand et al. |
| 5,833,709 A | 11/1998 | Rise et al. |
| 5,833,714 A | 11/1998 | Loeb |
| 5,843,148 A | 12/1998 | Gijsbers et al. |
| 5,893,883 A | 4/1999 | Torgerson et al. |
| 5,913,882 A | 6/1999 | King |
| 5,921,924 A * | 7/1999 | Avitall ........................ 600/374 |
| 5,927,277 A | 7/1999 | Baudino et al. |
| 5,941,906 A | 8/1999 | Barreras et al. |
| 5,957,958 A | 9/1999 | Schulman et al. |
| 5,975,085 A | 11/1999 | Rise |
| 5,978,702 A | 11/1999 | Ward et al. |
| 5,991,668 A | 11/1999 | Leinders et al. |
| 6,011,996 A | 1/2000 | Gielen et al. |
| 6,018,682 A | 1/2000 | Rise |
| 6,024,095 A | 2/2000 | Stanley, III |
| 6,033,403 A | 3/2000 | Tu et al. |
| 6,038,480 A | 3/2000 | Hrdlicka et al. |
| 6,050,992 A | 4/2000 | Nichols |
| 6,094,598 A | 7/2000 | Elsberry et al. |
| 6,104,960 A | 8/2000 | Duysens et al. |
| 6,109,269 A | 8/2000 | Rise et al. |
| 6,125,300 A | 9/2000 | Weijand et al. |
| 6,128,537 A | 10/2000 | Rise |
| 6,129,685 A | 10/2000 | Howard, III |
| 6,161,047 A | 12/2000 | King et al. |
| 6,205,359 B1 | 3/2001 | Boveja |
| 6,205,361 B1 | 3/2001 | Kuzma et al. |
| 6,216,043 B1 | 4/2001 | Swanson et al. |
| 6,227,203 B1 | 5/2001 | Rise et al. |
| 6,253,109 B1 | 6/2001 | Gielen |
| 6,253,110 B1 | 6/2001 | Brabec et al. |
| 6,263,237 B1 | 7/2001 | Rise |
| 6,266,564 B1 | 7/2001 | Hill et al. |
| 6,295,476 B1 | 9/2001 | Schaenzer |
| 6,319,241 B1 | 11/2001 | King et al. |
| 6,330,466 B1 | 12/2001 | Hofmann et al. |
| 6,337,997 B1 | 1/2002 | Rise |
| 6,343,226 B1 | 1/2002 | Sunde et al. |
| 6,353,762 B1 | 3/2002 | Baudino et al. |
| 6,356,784 B1 | 3/2002 | Lozano et al. |
| 6,356,786 B1 | 3/2002 | Rezai et al. |
| 6,356,787 B1 | 3/2002 | Rezai et al. |
| 6,364,875 B1 | 4/2002 | Stanley, III |
| 6,366,813 B1 | 4/2002 | DiLorenzo |
| 6,374,140 B1 | 4/2002 | Rise |
| 6,375,666 B1 | 4/2002 | Mische |
| 6,379,353 B1 | 4/2002 | Nichols |
| 6,415,187 B1 | 7/2002 | Kuzma et al. |
| 6,434,431 B1 | 8/2002 | Camps et al. |
| 6,479,999 B1 | 11/2002 | DeMeester et al. |
| 6,484,059 B2 | 11/2002 | Gielen |
| 6,493,590 B1 | 12/2002 | Wessman et al. |
| 6,529,774 B1 | 3/2003 | Greene |
| 6,538,443 B2 | 3/2003 | Morich et al. |
| 6,549,812 B1 | 4/2003 | Smits |
| 6,556,873 B1 | 4/2003 | Smits |
| 6,560,472 B2 | 5/2003 | Hill et al. |
| 6,560,486 B1 | 5/2003 | Osorio et al. |
| 6,587,733 B1 | 7/2003 | Cross et al. |
| 6,591,128 B1 | 7/2003 | Wu et al. |
| 6,594,524 B2 | 7/2003 | Esteller et al. |
| 6,597,953 B2 | 7/2003 | Boling |
| 6,643,552 B2 | 11/2003 | Edell et al. |
| 6,671,544 B2 | 12/2003 | Baudino |
| 6,675,046 B2 | 1/2004 | Holsheimer |
| 6,687,538 B1 | 2/2004 | Hrdlicka et al. |
| 6,690,973 B2 | 2/2004 | Hill et al. |
| 6,708,064 B2 | 3/2004 | Rezai |
| 6,718,208 B2 | 4/2004 | Hill et al. |
| 6,718,211 B2 | 4/2004 | Smits |
| 6,741,893 B2 | 5/2004 | Smits |
| 6,745,079 B2 | 6/2004 | King |
| 6,757,970 B1 | 7/2004 | Kuzma et al. |
| 6,795,737 B2 | 9/2004 | Gielen et al. |
| 6,804,552 B2 | 10/2004 | Thompson et al. |
| 6,818,396 B1 | 11/2004 | Bloch et al. |
| 6,829,498 B2 | 12/2004 | Kipke et al. |
| 6,850,802 B2 | 2/2005 | Holsheimer |
| 6,871,098 B2 | 3/2005 | Nuttin et al. |
| 6,882,881 B1 | 4/2005 | Lesser et al. |
| 6,892,097 B2 | 5/2005 | Holsheimer |
| 6,892,438 B1 | 5/2005 | Hill et al. |
| 6,904,306 B1 | 6/2005 | Wu et al. |
| 6,909,920 B2 | 6/2005 | Lokhoff et al. |
| 6,920,359 B2 | 7/2005 | Meadows et al. |
| 6,928,320 B2 | 8/2005 | King |
| 6,950,706 B2 | 9/2005 | Rodriguez et al. |
| 6,950,709 B2 | 9/2005 | Baudino |
| 6,978,171 B2 | 12/2005 | Goetz et al. |
| 6,978,178 B2 | 12/2005 | Sommer et al. |
| 6,999,819 B2 | 2/2006 | Swoyer et al. |
| 7,006,859 B1 | 2/2006 | Osorio et al. |
| 7,010,351 B2 | 3/2006 | Firlik et al. |
| 7,010,356 B2 | 3/2006 | Jog et al. |
| 7,024,246 B2 | 4/2006 | Acosta et al. |
| 7,035,690 B2 | 4/2006 | Goetz |

(56) References Cited

U.S. PATENT DOCUMENTS

| | | |
|---|---|---|
| 7,047,082 B1 | 5/2006 | Schrom et al. |
| 7,047,084 B2 | 5/2006 | Erickson et al. |
| 7,050,856 B2 | 5/2006 | Stypulkowski |
| 7,051,419 B2 | 5/2006 | Schrom et al. |
| 7,061,240 B2 | 6/2006 | Ham et al. |
| 7,063,767 B1 | 6/2006 | Tyson et al. |
| 7,076,292 B2 | 7/2006 | Forsberg |
| 7,077,822 B1 | 7/2006 | Howard, III |
| 7,107,104 B2 | 9/2006 | Keravel et al. |
| 7,133,718 B2 | 11/2006 | Bakken et al. |
| 7,146,222 B2 | 12/2006 | Boling |
| 7,151,961 B1 | 12/2006 | Whitehurst et al. |
| 7,174,219 B2 | 2/2007 | Wahlstrand et al. |
| 7,177,701 B1 | 2/2007 | Pianca |
| 7,181,288 B1 | 2/2007 | Rezai et al. |
| 7,184,829 B2 | 2/2007 | Hill et al. |
| 7,187,978 B2 | 3/2007 | Malek et al. |
| 7,191,016 B2 | 3/2007 | Marshall et al. |
| 7,191,018 B2 | 3/2007 | Gielen et al. |
| 7,200,439 B2 | 4/2007 | Zdeblick et al. |
| 7,203,548 B2 | 4/2007 | Whitehurst et al. |
| 7,204,798 B2 | 4/2007 | Zdeblick et al. |
| 7,204,833 B1 | 4/2007 | Osorio et al. |
| 7,209,787 B2 | 4/2007 | Dilorenzo |
| 7,212,851 B2 | 5/2007 | Donoghue et al. |
| 7,212,867 B2 | 5/2007 | Van Venrooij et al. |
| 7,214,189 B2 | 5/2007 | Zdeblick |
| 7,216,000 B2 | 5/2007 | Sieracki et al. |
| 7,216,001 B2 | 5/2007 | Hacker et al. |
| 7,231,256 B2 | 6/2007 | Wahlstrand et al. |
| 7,236,822 B2 | 6/2007 | Dobak, III |
| 7,242,984 B2 | 7/2007 | DiLorenzo |
| 7,276,061 B2 | 10/2007 | Schaer et al. |
| 7,280,867 B2 | 10/2007 | Frei et al. |
| 7,282,030 B2 | 10/2007 | Frei et al. |
| 7,282,050 B2 | 10/2007 | Starkebaum et al. |
| 7,286,878 B2 | 10/2007 | Stypulkowski |
| 7,286,882 B2 | 10/2007 | Cole |
| 7,288,066 B2 | 10/2007 | Drew |
| 7,289,851 B2 | 10/2007 | Gunderson et al. |
| 7,289,852 B2 | 10/2007 | Helfinstine et al. |
| 7,295,880 B2 | 11/2007 | Gielen |
| 7,298,143 B2 | 11/2007 | Jaermann et al. |
| 7,307,223 B2 | 12/2007 | Tyson et al. |
| 7,313,430 B2 | 12/2007 | Urquhart et al. |
| 7,313,440 B2 | 12/2007 | Miesel |
| 7,315,759 B2 | 1/2008 | Markowitz et al. |
| 7,317,947 B2 | 1/2008 | Wahlstrand et al. |
| 7,317,948 B1 | 1/2008 | King et al. |
| 7,319,899 B2 | 1/2008 | Keizer |
| 7,319,904 B2 | 1/2008 | Cross et al. |
| 7,321,798 B2 | 1/2008 | Muhlenberg et al. |
| 7,321,837 B2 | 1/2008 | Osorio et al. |
| 7,322,832 B2 | 1/2008 | Kronich et al. |
| 7,328,057 B2 | 2/2008 | Freas et al. |
| 7,328,068 B2 | 2/2008 | Spinelli et al. |
| 7,328,069 B2 | 2/2008 | Gerber |
| 7,330,760 B2 | 2/2008 | Heruth et al. |
| 7,337,010 B2 | 2/2008 | Howard et al. |
| 7,343,206 B2 | 3/2008 | Sage et al. |
| 7,346,395 B2 | 3/2008 | Lozano et al. |
| 7,356,369 B2 | 4/2008 | Phillips et al. |
| 7,359,837 B2 | 4/2008 | Drew |
| 7,366,572 B2 | 4/2008 | Heruth et al. |
| 7,367,956 B2 | 5/2008 | King |
| 7,369,891 B2 | 5/2008 | Augustijn et al. |
| 7,369,893 B2 | 5/2008 | Gunderson |
| 7,369,894 B2 | 5/2008 | Gerber |
| 7,385,443 B1 | 6/2008 | Denison |
| 7,388,378 B2 | 6/2008 | Gray et al. |
| 7,389,147 B2 | 6/2008 | Wahlstrand et al. |
| 7,390,311 B2 | 6/2008 | Hildebrand et al. |
| 7,391,257 B1 | 6/2008 | Denison et al. |
| 7,392,089 B2 | 6/2008 | Wahlstrand et al. |
| 7,395,113 B2 | 7/2008 | Heruth et al. |
| 7,400,927 B1 | 7/2008 | Litvin |
| 7,406,351 B2 | 7/2008 | Wesselink |
| 7,418,292 B2 | 8/2008 | Shafer |
| 7,421,297 B2 | 9/2008 | Giftakis et al. |
| 7,427,280 B2 | 9/2008 | Gerber |
| 7,429,938 B1 | 9/2008 | Corndorf |
| 7,433,734 B2 | 10/2008 | King |
| 7,442,183 B2 | 10/2008 | Baudino et al. |
| 7,447,545 B2 | 11/2008 | Heruth et al. |
| 7,450,996 B2 | 11/2008 | MacDonald et al. |
| 7,463,917 B2 | 12/2008 | Martinez |
| 7,463,928 B2 | 12/2008 | Lee et al. |
| 7,474,247 B1 | 1/2009 | Heinks et al. |
| 7,479,910 B1 | 1/2009 | Heinks et al. |
| 7,483,748 B2 | 1/2009 | Torgerson et al. |
| 7,489,966 B2 | 2/2009 | Leinders et al. |
| 7,489,970 B2 | 2/2009 | Lee et al. |
| 7,491,181 B2 | 2/2009 | Heruth et al. |
| 7,497,844 B2 | 3/2009 | Spear et al. |
| 7,497,863 B2 | 3/2009 | Solar et al. |
| 7,502,217 B2 | 3/2009 | Zhao et al. |
| 7,505,815 B2 | 3/2009 | Lee et al. |
| 7,505,869 B2 | 3/2009 | Hartlaub |
| 7,515,961 B2 | 4/2009 | Germanson et al. |
| 7,519,431 B2 | 4/2009 | Goetz et al. |
| 7,519,432 B2 | 4/2009 | Bolea et al. |
| 7,520,890 B2 | 4/2009 | Phillips |
| 7,526,339 B2 | 4/2009 | Lahti et al. |
| 7,526,340 B2 | 4/2009 | Drew |
| 7,526,341 B2 | 4/2009 | Goetz et al. |
| 7,529,582 B1 | 5/2009 | DiLorenzo |
| 7,529,586 B2 | 5/2009 | Wahlstrand et al. |
| 7,542,803 B2 | 6/2009 | Heruth et al. |
| 7,546,164 B2 | 6/2009 | King |
| 7,546,166 B2 | 6/2009 | Michels et al. |
| 7,548,775 B2 | 6/2009 | Kipke et al. |
| 7,548,786 B2 | 6/2009 | Lee et al. |
| 7,551,951 B1 | 6/2009 | Osorio et al. |
| 7,551,960 B2 | 6/2009 | Forsberg et al. |
| 7,555,345 B2 | 6/2009 | Wahlstrand et al. |
| 7,561,921 B2 | 7/2009 | Phillips et al. |
| 7,563,141 B2 | 7/2009 | Alexander et al. |
| 7,563,541 B2 | 7/2009 | Howard et al. |
| 7,578,819 B2 | 8/2009 | Bleich et al. |
| 7,580,756 B2 | 8/2009 | Schulte et al. |
| 7,582,387 B2 | 9/2009 | Howard et al. |
| 7,590,451 B2 | 9/2009 | Tronnes et al. |
| 7,590,453 B2 | 9/2009 | Heruth et al. |
| 7,590,455 B2 | 9/2009 | Heruth et al. |
| 7,591,970 B2 | 9/2009 | Olson |
| 7,594,828 B2 | 9/2009 | Alexander et al. |
| 7,594,889 B2 | 9/2009 | St. Ores et al. |
| 7,596,399 B2 | 9/2009 | Singhal et al. |
| 7,596,408 B2 | 9/2009 | Singhal et al. |
| 7,596,415 B2 | 9/2009 | Brabec et al. |
| 7,599,730 B2 | 10/2009 | Hunter et al. |
| 7,603,161 B2 | 10/2009 | Wurmfeld et al. |
| 7,603,177 B2 | 10/2009 | Sieracki et al. |
| 7,604,629 B2 | 10/2009 | Gerber et al. |
| 7,604,644 B2 | 10/2009 | Schulte et al. |
| 7,608,458 B2 | 10/2009 | Soykan et al. |
| 7,610,083 B2 | 10/2009 | Drew et al. |
| 7,611,483 B2 | 11/2009 | Gerber et al. |
| 7,614,743 B2 | 11/2009 | Geiger |
| 7,615,015 B2 | 11/2009 | Coleman |
| 7,616,998 B2 | 11/2009 | Nuttin et al. |
| 7,617,002 B2 | 11/2009 | Goetz |
| 7,620,454 B2 | 11/2009 | Dinsmoor et al. |
| 7,622,303 B2 | 11/2009 | Soykan et al. |
| 7,622,988 B2 | 11/2009 | Denison et al. |
| 7,623,053 B2 | 11/2009 | Terry et al. |
| 7,623,918 B2 | 11/2009 | Goetz |
| 7,623,919 B2 | 11/2009 | Goetz et al. |
| 7,623,923 B2 | 11/2009 | Gerber et al. |
| 7,623,930 B2 | 11/2009 | Zeijlemaker et al. |
| 7,624,293 B2 | 11/2009 | Osorio et al. |
| 7,628,780 B2 | 12/2009 | Bonner et al. |
| 7,631,415 B2 | 12/2009 | Phillips et al. |
| 7,632,225 B2 | 12/2009 | Stypulkowski |

(56) References Cited

U.S. PATENT DOCUMENTS

| | | |
|---|---|---|
| 7,635,541 B2 | 12/2009 | Scott et al. |
| 7,637,867 B2 | 12/2009 | Zdeblick |
| 7,640,059 B2 | 12/2009 | Forsberg et al. |
| 7,640,060 B2 | 12/2009 | Zdeblick |
| 7,641,992 B2 | 1/2010 | Howard et al. |
| 7,642,013 B2 | 1/2010 | Howard et al. |
| 7,647,111 B2 | 1/2010 | Ries et al. |
| 7,647,116 B2 | 1/2010 | Bauhahn |
| 7,647,117 B2 | 1/2010 | Bauhahn |
| 7,647,121 B2 | 1/2010 | Wahlstrand et al. |
| 7,650,291 B2 | 1/2010 | Rosenfeld et al. |
| 7,653,433 B2 | 1/2010 | Lozano et al. |
| 7,657,318 B2 | 2/2010 | King et al. |
| 7,657,319 B2 | 2/2010 | Goetz et al. |
| 7,660,620 B2 | 2/2010 | Zeijlemaker et al. |
| 7,660,630 B2 | 2/2010 | Dudding et al. |
| 7,662,140 B2 | 2/2010 | Heruth et al. |
| 7,662,509 B2 | 2/2010 | Howard et al. |
| 7,663,066 B2 | 2/2010 | Tyson et al. |
| 7,664,551 B2 | 2/2010 | Cigaina |
| 7,664,552 B2 | 2/2010 | Wahlstrand et al. |
| 7,668,601 B2 | 2/2010 | Hegland et al. |
| 7,671,594 B2 | 3/2010 | Gray |
| 7,676,271 B2 | 3/2010 | Wahlstrand et al. |
| 7,676,273 B2 | 3/2010 | Goetz et al. |
| 7,676,274 B2 | 3/2010 | Hung et al. |
| 7,680,540 B2 | 3/2010 | Jensen et al. |
| 7,682,355 B2 | 3/2010 | Gerber et al. |
| 7,682,745 B2 | 3/2010 | Howard et al. |
| 7,684,860 B2 | 3/2010 | Wahlstrand et al. |
| 7,684,873 B2 | 3/2010 | Gerber |
| 7,689,289 B2 | 3/2010 | King |
| 7,697,972 B2 | 4/2010 | Verard et al. |
| 7,697,995 B2 | 4/2010 | Cross et al. |
| 7,706,124 B2 | 4/2010 | Zhao et al. |
| 7,706,889 B2 | 4/2010 | Gerber et al. |
| 7,711,421 B2 | 5/2010 | Shafer et al. |
| 7,711,428 B2 | 5/2010 | Janzig et al. |
| 7,711,436 B2 | 5/2010 | Stone |
| 7,713,194 B2 | 5/2010 | Zdeblick |
| 7,713,195 B2 | 5/2010 | Zdeblick |
| 7,720,548 B2 | 5/2010 | King |
| 7,729,768 B2 | 6/2010 | White et al. |
| 7,729,780 B2 | 6/2010 | Vardiman |
| 7,738,958 B2 | 6/2010 | Zdeblick et al. |
| 7,742,823 B2 | 6/2010 | King et al. |
| 7,756,588 B2 | 7/2010 | Jog et al. |
| 7,797,029 B2 | 9/2010 | Gibson et al. |
| 7,822,483 B2 | 10/2010 | Stone et al. |
| 7,853,303 B2 | 12/2010 | Nikumb et al. |
| 7,877,149 B2 | 1/2011 | Zdeblick |
| 7,899,539 B2 | 3/2011 | Whitehurst et al. |
| 7,925,329 B2 | 4/2011 | Zdeblick et al. |
| 7,930,035 B2 | 4/2011 | DiLorenzo |
| 7,935,056 B2 | 5/2011 | Zdeblick |
| 7,941,202 B2 | 5/2011 | Hetke et al. |
| 7,945,336 B2 | 5/2011 | Sauter-Starace et al. |
| 7,969,161 B2 | 6/2011 | Behzadi et al. |
| 7,974,705 B2 | 7/2011 | Zdeblick et al. |
| 7,978,064 B2 | 7/2011 | Zdeblick et al. |
| 7,979,105 B2 | 7/2011 | Kipke et al. |
| 7,983,751 B2 | 7/2011 | Zdeblick et al. |
| 8,000,794 B2 | 8/2011 | Lozano |
| 8,000,808 B2 | 8/2011 | Hegland et al. |
| 8,032,224 B2 | 10/2011 | Miesel et al. |
| 8,036,737 B2 | 10/2011 | Goetz et al. |
| 8,036,743 B2 | 10/2011 | Savage et al. |
| 8,036,748 B2 | 10/2011 | Zdeblick et al. |
| 8,055,334 B2 | 11/2011 | Savage et al. |
| 8,055,353 B2 | 11/2011 | Kreidler et al. |
| 8,099,170 B2 | 1/2012 | Jensen et al. |
| 8,114,021 B2 | 2/2012 | Robertson et al. |
| 8,115,618 B2 | 2/2012 | Robertson et al. |
| 8,121,687 B2 | 2/2012 | Jensen et al. |
| 8,123,684 B2 | 2/2012 | Zdeblick |
| 8,172,762 B2 | 5/2012 | Robertson |
| 8,187,161 B2 | 5/2012 | Li et al. |
| 8,195,308 B2 | 6/2012 | Frank et al. |
| 8,204,586 B2 | 6/2012 | Zdeblick |
| 8,258,962 B2 | 9/2012 | Robertson et al. |
| 8,261,428 B2 | 9/2012 | Fang et al. |
| 8,280,514 B2 | 10/2012 | Lozano et al. |
| 8,332,020 B2 | 12/2012 | Zdeblick |
| 8,355,768 B2 | 1/2013 | Masmanidis et al. |
| 8,412,347 B2 | 4/2013 | Zdeblick |
| 8,473,061 B2 | 6/2013 | Moffitt et al. |
| 8,473,069 B2 | 6/2013 | Bi et al. |
| 8,489,203 B2 | 7/2013 | Ortmann |
| 8,788,064 B2 | 7/2014 | Mercanzini et al. |
| 8,874,232 B2 | 10/2014 | Chen |
| 8,897,891 B2 | 11/2014 | Romero |
| 8,938,308 B2 | 1/2015 | Meadows |
| 2002/0062143 A1 | 5/2002 | Baudino et al. |
| 2003/0004553 A1 | 1/2003 | Grill et al. |
| 2003/0023282 A1 | 1/2003 | Barrett et al. |
| 2003/0036780 A1 | 2/2003 | Barrett et al. |
| 2003/0060822 A1 | 3/2003 | Schaer et al. |
| 2003/0083724 A1 | 5/2003 | Jog et al. |
| 2003/0100823 A1 | 5/2003 | Kipke et al. |
| 2003/0135253 A1 | 7/2003 | Kokones et al. |
| 2003/0176892 A1 | 9/2003 | Shalev |
| 2004/0002635 A1 | 1/2004 | Hargrove et al. |
| 2004/0015205 A1 | 1/2004 | Whitehurst et al. |
| 2004/0039434 A1 | 2/2004 | Schrom et al. |
| 2004/0102828 A1 | 5/2004 | Lowry et al. |
| 2004/0122335 A1 | 6/2004 | Sackellares et al. |
| 2004/0133390 A1 | 7/2004 | Osorio et al. |
| 2004/0138517 A1 | 7/2004 | Osorio et al. |
| 2004/0138536 A1 | 7/2004 | Frei et al. |
| 2004/0138720 A1 | 7/2004 | Naisberg et al. |
| 2004/0138722 A1 | 7/2004 | Carroll et al. |
| 2004/0152958 A1 | 8/2004 | Frei et al. |
| 2004/0172089 A1 | 9/2004 | Whitehurst et al. |
| 2004/0193021 A1 | 9/2004 | Zdeblick et al. |
| 2004/0215288 A1 | 10/2004 | Lee et al. |
| 2004/0220637 A1 | 11/2004 | Zdeblick et al. |
| 2004/0225335 A1 | 11/2004 | Whitehurst et al. |
| 2004/0243011 A1* | 12/2004 | Plaza .................. 600/509 |
| 2004/0249417 A1 | 12/2004 | Ransbury et al. |
| 2004/0254483 A1 | 12/2004 | Zdeblick et al. |
| 2005/0004627 A1 | 1/2005 | Gibson et al. |
| 2005/0008660 A1 | 1/2005 | Kipke et al. |
| 2005/0010261 A1 | 1/2005 | Luders et al. |
| 2005/0021103 A1 | 1/2005 | DiLorenzo |
| 2005/0027284 A1 | 2/2005 | Lozano et al. |
| 2005/0033136 A1 | 2/2005 | Govari et al. |
| 2005/0038489 A1 | 2/2005 | Grill |
| 2005/0049655 A1 | 3/2005 | Boveja et al. |
| 2005/0070971 A1 | 3/2005 | Fowler et al. |
| 2005/0075681 A1 | 4/2005 | Rezai et al. |
| 2005/0113882 A1 | 5/2005 | Cameron et al. |
| 2005/0137647 A1 | 6/2005 | Wallace et al. |
| 2005/0143790 A1 | 6/2005 | Kipke et al. |
| 2005/0154425 A1 | 7/2005 | Boveja et al. |
| 2005/0171558 A1 | 8/2005 | Abovitz et al. |
| 2005/0182455 A1 | 8/2005 | Thrope et al. |
| 2005/0209511 A1 | 9/2005 | Heruth et al. |
| 2005/0209513 A1 | 9/2005 | Heruth et al. |
| 2005/0209643 A1 | 9/2005 | Heruth et al. |
| 2005/0222642 A1 | 10/2005 | Przybyszewski et al. |
| 2005/0240242 A1 | 10/2005 | DiLorenzo |
| 2005/0245988 A1 | 11/2005 | Miesel |
| 2006/0004422 A1 | 1/2006 | De Ridder |
| 2006/0030897 A1 | 2/2006 | Gilmer et al. |
| 2006/0041295 A1 | 2/2006 | Osypka |
| 2006/0049957 A1 | 3/2006 | Surgenor et al. |
| 2006/0058588 A1 | 3/2006 | Zdeblick |
| 2006/0058727 A1 | 3/2006 | Bernabei |
| 2006/0058855 A1 | 3/2006 | Gill |
| 2006/0095105 A1 | 5/2006 | Jog et al. |
| 2006/0116581 A1 | 6/2006 | Zdeblick et al. |
| 2006/0129203 A1 | 6/2006 | Garabedian et al. |
| 2006/0135877 A1 | 6/2006 | Giftakis et al. |
| 2006/0149336 A1 | 7/2006 | Meadows |

(56) References Cited

U.S. PATENT DOCUMENTS

| | | |
|---|---|---|
| 2006/0149337 A1 | 7/2006 | John |
| 2006/0167497 A1 | 7/2006 | Armstrong et al. |
| 2006/0173263 A1 | 8/2006 | He et al. |
| 2006/0173510 A1 | 8/2006 | Besio et al. |
| 2006/0178709 A1 | 8/2006 | Foster et al. |
| 2006/0195154 A1 | 8/2006 | Jaax et al. |
| 2006/0200206 A1 | 9/2006 | Firlik et al. |
| 2006/0212090 A1 | 9/2006 | Lozano et al. |
| 2006/0241717 A1 | 10/2006 | Whitehurst et al. |
| 2006/0258951 A1 | 11/2006 | Bleich et al. |
| 2006/0264777 A1 | 11/2006 | Drew |
| 2006/0276866 A1 | 12/2006 | McCreery |
| 2006/0282014 A1 | 12/2006 | Kipke et al. |
| 2006/0293720 A1 | 12/2006 | Dilorenzo |
| 2006/0293721 A1 | 12/2006 | Tarver et al. |
| 2007/0027498 A1 | 2/2007 | Maschino et al. |
| 2007/0027500 A1 | 2/2007 | Maschino et al. |
| 2007/0027514 A1 | 2/2007 | Gerber |
| 2007/0043268 A1 | 2/2007 | Russell |
| 2007/0060974 A1 | 3/2007 | Lozano |
| 2007/0067002 A1 | 3/2007 | Lozano |
| 2007/0067003 A1 | 3/2007 | Sanchez et al. |
| 2007/0088403 A1 | 4/2007 | Wyler et al. |
| 2007/0088404 A1 | 4/2007 | Wyler et al. |
| 2007/0093870 A1 | 4/2007 | Maschino |
| 2007/0100389 A1 | 5/2007 | Jaax et al. |
| 2007/0100392 A1 | 5/2007 | Maschino et al. |
| 2007/0100393 A1 | 5/2007 | Whitehurst et al. |
| 2007/0100398 A1 | 5/2007 | Sloan |
| 2007/0106143 A1 | 5/2007 | Flaherty |
| 2007/0123765 A1 | 5/2007 | Hetke et al. |
| 2007/0123944 A1 | 5/2007 | Zdeblick |
| 2007/0135721 A1 | 6/2007 | Zdeblick |
| 2007/0142872 A1 | 6/2007 | Mickle et al. |
| 2007/0150024 A1 | 6/2007 | Leyde et al. |
| 2007/0173890 A1 | 7/2007 | Armstrong |
| 2007/0173896 A1 | 7/2007 | Zdeblick |
| 2007/0173897 A1 | 7/2007 | Zdeblick |
| 2007/0173901 A1 | 7/2007 | Reeve |
| 2007/0173908 A1 | 7/2007 | Begnaud |
| 2007/0179558 A1 | 8/2007 | Gliner et al. |
| 2007/0179569 A1 | 8/2007 | Zdeblick |
| 2007/0185537 A1 | 8/2007 | Zdeblick |
| 2007/0185544 A1 | 8/2007 | Dawant et al. |
| 2007/0185548 A1 | 8/2007 | Zdeblick |
| 2007/0185549 A1 | 8/2007 | Zdeblick |
| 2007/0197892 A1 | 8/2007 | Shen et al. |
| 2007/0203537 A1 | 8/2007 | Goetz et al. |
| 2007/0203546 A1 | 8/2007 | Stone et al. |
| 2007/0208394 A1 | 9/2007 | King et al. |
| 2007/0213784 A1 | 9/2007 | Pless |
| 2007/0213785 A1 | 9/2007 | Osorio et al. |
| 2007/0213786 A1 | 9/2007 | Sackellares et al. |
| 2007/0219591 A1 | 9/2007 | Zdeblick et al. |
| 2007/0225674 A1 | 9/2007 | Molnar et al. |
| 2007/0225773 A1 | 9/2007 | Shen et al. |
| 2007/0225774 A1 | 9/2007 | Eskandar et al. |
| 2007/0233192 A1 | 10/2007 | Craig |
| 2007/0249953 A1 | 10/2007 | Frei et al. |
| 2007/0249954 A1 | 10/2007 | Virag et al. |
| 2007/0250133 A1 | 10/2007 | Carlson et al. |
| 2007/0255323 A1 | 11/2007 | Werder et al. |
| 2007/0255338 A1 | 11/2007 | Wahlstrand |
| 2007/0255374 A1 | 11/2007 | Kolafa et al. |
| 2007/0255531 A1 | 11/2007 | Drew |
| 2007/0265683 A1 | 11/2007 | Ehrlich |
| 2007/0282389 A1 | 12/2007 | Moxon et al. |
| 2007/0293908 A1 | 12/2007 | Cowan et al. |
| 2008/0021514 A1 | 1/2008 | Pless |
| 2008/0021517 A1 | 1/2008 | Dietrich |
| 2008/0027289 A1 | 1/2008 | Zdeblick |
| 2008/0027487 A1 | 1/2008 | Patel et al. |
| 2008/0027503 A1 | 1/2008 | Marrosu et al. |
| 2008/0027504 A1 | 1/2008 | Bedenbaugh |
| 2008/0027540 A1 | 1/2008 | Cumming |
| 2008/0039895 A1 | 2/2008 | Fowler et al. |
| 2008/0046012 A1 | 2/2008 | Covalin et al. |
| 2008/0046013 A1 | 2/2008 | Lozano |
| 2008/0058630 A1 | 3/2008 | Robertson |
| 2008/0077186 A1 | 3/2008 | Thompson et al. |
| 2008/0077191 A1 | 3/2008 | Morrell |
| 2008/0103547 A1 | 5/2008 | Okun et al. |
| 2008/0103548 A1 | 5/2008 | Fowler et al. |
| 2008/0103578 A1 | 5/2008 | Gerber |
| 2008/0114417 A1 | 5/2008 | Leyde |
| 2008/0119900 A1 | 5/2008 | DiLorenzo |
| 2008/0139870 A1 | 6/2008 | Gliner et al. |
| 2008/0140152 A1 | 6/2008 | Imran et al. |
| 2008/0154328 A1 | 6/2008 | Thompson et al. |
| 2008/0154331 A1 | 6/2008 | John et al. |
| 2008/0161881 A1 | 7/2008 | Firlik et al. |
| 2008/0161896 A1 | 7/2008 | Sauter-Starace et al. |
| 2008/0172103 A1 | 7/2008 | Kao et al. |
| 2008/0177196 A1 | 7/2008 | Burdick et al. |
| 2008/0188905 A1 | 8/2008 | Swartz |
| 2008/0195166 A1 | 8/2008 | Sun et al. |
| 2008/0195227 A1 | 8/2008 | Boling et al. |
| 2008/0208283 A1 | 8/2008 | Vetter et al. |
| 2008/0208287 A1 | 8/2008 | Palermo et al. |
| 2008/0215125 A1 | 9/2008 | Farah et al. |
| 2008/0221642 A1 | 9/2008 | Humayun et al. |
| 2008/0242976 A1 | 10/2008 | Robertson et al. |
| 2008/0255439 A1 | 10/2008 | Tang et al. |
| 2008/0255629 A1 | 10/2008 | Jenson et al. |
| 2008/0255647 A1 | 10/2008 | Jensen et al. |
| 2008/0269835 A1 | 10/2008 | Carlson et al. |
| 2008/0269842 A1 | 10/2008 | Giftakis et al. |
| 2008/0275526 A1 | 11/2008 | Lozano |
| 2008/0284599 A1 | 11/2008 | Zdeblick et al. |
| 2008/0294218 A1 | 11/2008 | Savage et al. |
| 2008/0300652 A1 | 12/2008 | Lim et al. |
| 2008/0306394 A1 | 12/2008 | Zdeblick et al. |
| 2008/0312726 A1 | 12/2008 | Frank et al. |
| 2008/0316020 A1 | 12/2008 | Robertson et al. |
| 2009/0027504 A1 | 1/2009 | Lim et al. |
| 2009/0062879 A1 | 3/2009 | Li et al. |
| 2009/0082645 A1 | 3/2009 | Hafezi et al. |
| 2009/0105784 A1 | 4/2009 | Massoud-Ansari et al. |
| 2009/0118806 A1 | 5/2009 | Vetter et al. |
| 2009/0132042 A1 | 5/2009 | Hetke et al. |
| 2009/0171416 A1 | 7/2009 | Firlik et al. |
| 2009/0177144 A1 | 7/2009 | Masmanidis et al. |
| 2009/0187196 A1 | 7/2009 | Vetter |
| 2009/0204183 A1 | 8/2009 | Kreidler et al. |
| 2009/0240314 A1 | 9/2009 | Kong et al. |
| 2009/0253977 A1 | 10/2009 | Kipke et al. |
| 2009/0256702 A1 | 10/2009 | Robertson et al. |
| 2009/0292325 A1 | 11/2009 | Cederna et al. |
| 2009/0299174 A1 | 12/2009 | Wright et al. |
| 2009/0306728 A1 | 12/2009 | Wright et al. |
| 2009/0306729 A1 | 12/2009 | Doerr |
| 2009/0312770 A1 | 12/2009 | Kozai et al. |
| 2009/0318824 A1 | 12/2009 | Nishida et al. |
| 2009/0325424 A1 | 12/2009 | Aarts et al. |
| 2010/0014541 A1 | 1/2010 | Harriman |
| 2010/0015274 A1 | 1/2010 | Fill |
| 2010/0030298 A1 | 2/2010 | Martens et al. |
| 2010/0036468 A1 | 2/2010 | Decre et al. |
| 2010/0069717 A1 | 3/2010 | Hafezi et al. |
| 2010/0076536 A1 | 3/2010 | Merz et al. |
| 2010/0087853 A1 | 4/2010 | Kipke et al. |
| 2010/0100152 A1 | 4/2010 | Martens et al. |
| 2010/0106178 A1 | 4/2010 | Obermiller et al. |
| 2010/0114193 A1 | 5/2010 | Lozano et al. |
| 2010/0114234 A1 | 5/2010 | Zdeblick |
| 2010/0114250 A1 | 5/2010 | Zdeblick |
| 2010/0130844 A1* | 5/2010 | Williams et al. ............ 600/378 |
| 2010/0145216 A1 | 6/2010 | He et al. |
| 2010/0145414 A1 | 6/2010 | Decre et al. |
| 2010/0152747 A1 | 6/2010 | Padiy et al. |
| 2010/0198315 A1 | 8/2010 | Martens et al. |
| 2010/0249883 A1 | 9/2010 | Zdeblick |
| 2010/0274305 A1 | 10/2010 | Gliner et al. |
| 2010/0292602 A1 | 11/2010 | Worrell et al. |

(56) References Cited

U.S. PATENT DOCUMENTS

| | | |
|---|---|---|
| 2010/0298908 A1 | 11/2010 | Vardiman |
| 2010/0298917 A1 | 11/2010 | Vardiman |
| 2010/0298918 A1 | 11/2010 | Vardiman |
| 2010/0312188 A1 | 12/2010 | Robertson et al. |
| 2010/0312228 A1 | 12/2010 | Zdeblick et al. |
| 2010/0318163 A1 | 12/2010 | Zdeblick |
| 2010/0331807 A1 | 12/2010 | Whitehurst et al. |
| 2011/0001488 A1 | 1/2011 | Behzadi et al. |
| 2011/0022124 A1 | 1/2011 | Zdeblick et al. |
| 2011/0034964 A1 | 2/2011 | Bi et al. |
| 2011/0034970 A1* | 2/2011 | Barker .................. 607/72 |
| 2011/0040203 A1 | 2/2011 | Savage et al. |
| 2011/0071766 A1 | 3/2011 | Dolan et al. |
| 2011/0130809 A1 | 6/2011 | Zdeblick |
| 2011/0152988 A1 | 6/2011 | Whitehurst et al. |
| 2011/0154655 A1 | 6/2011 | Hetke et al. |
| 2011/0184495 A1 | 7/2011 | Wang et al. |
| 2011/0190860 A1 | 8/2011 | Harberts et al. |
| 2011/0196454 A1 | 8/2011 | Strand et al. |
| 2011/0208225 A1 | 8/2011 | Martens et al. |
| 2011/0213382 A1 | 9/2011 | Decre et al. |
| 2011/0218417 A1 | 9/2011 | Boogaard et al. |
| 2011/0224757 A1 | 9/2011 | Zdeblick et al. |
| 2011/0224765 A1 | 9/2011 | Harberts et al. |
| 2011/0224766 A1 | 9/2011 | Tol et al. |
| 2011/0282179 A1 | 11/2011 | Zdeblick |
| 2012/0004520 A1 | 1/2012 | Whitworth et al. |
| 2012/0004527 A1 | 1/2012 | Thompson et al. |
| 2012/0004716 A1 | 1/2012 | Langhammer et al. |
| 2012/0007734 A1 | 1/2012 | Berkman et al. |
| 2012/0022341 A1 | 1/2012 | Zdeblick |
| 2012/0035684 A1 | 2/2012 | Thompson et al. |
| 2012/0053344 A1 | 3/2012 | Lagos Gonzalez |
| 2012/0059444 A1 | 3/2012 | Pardoel et al. |
| 2012/0062379 A1 | 3/2012 | Hafezi et al. |
| 2012/0095355 A1 | 4/2012 | Zdeblick |
| 2012/0109262 A1 | 5/2012 | Martens |
| 2012/0109599 A1 | 5/2012 | Martens |
| 2012/0116188 A1 | 5/2012 | Frank et al. |
| 2012/0136420 A1 | 5/2012 | Pardoel et al. |
| 2012/0150256 A1 | 6/2012 | Martens |
| 2012/0184837 A1 | 7/2012 | Martens et al. |
| 2012/0253442 A1 | 10/2012 | Gliner et al. |
| 2012/0277821 A1 | 11/2012 | Martens et al. |
| 2012/0296444 A1 | 11/2012 | Greenberg et al. |
| 2012/0303088 A1 | 11/2012 | Van Kaam et al. |
| 2012/0303089 A1 | 11/2012 | Martens et al. |
| 2012/0303107 A1 | 11/2012 | Decre et al. |
| 2012/0316630 A1 | 12/2012 | Firlik et al. |
| 2013/0009691 A1 | 1/2013 | Blanken et al. |
| 2013/0030366 A1 | 1/2013 | Robertson et al. |
| 2013/0046356 A1 | 2/2013 | Jensen et al. |
| 2013/0060102 A1 | 3/2013 | Zdeblick |
| 2013/0085361 A1 | 4/2013 | Mercanzini et al. |
| 2013/0131754 A1 | 5/2013 | Sarvazyan |
| 2013/0144132 A1 | 6/2013 | Hafezi et al. |
| 2013/0172716 A1 | 7/2013 | Lozano et al. |
| 2013/0193950 A1 | 8/2013 | Hafezi et al. |
| 2013/0204318 A1 | 8/2013 | Young |
| 2013/0223028 A1 | 8/2013 | Arne et al. |
| 2013/0231188 A1 | 9/2013 | Berberich et al. |
| 2013/0282090 A1 | 10/2013 | Decre et al. |
| 2013/0345780 A1 | 12/2013 | Tabada et al. |
| 2013/0345789 A1 | 12/2013 | Havel et al. |
| 2014/0039578 A1 | 2/2014 | Whitehurst et al. |

FOREIGN PATENT DOCUMENTS

| | | |
|---|---|---|
| EP | 0 892 654 | 1/1999 |
| EP | 0 895 483 | 2/1999 |
| EP | 0 959 942 | 12/1999 |
| EP | 1 048 319 | 11/2000 |
| EP | 1 062 973 | 12/2000 |
| EP | 1 102 607 | 5/2001 |
| EP | 1 257 320 | 11/2002 |
| EP | 1 446 189 | 8/2004 |
| EP | 1 514 576 | 3/2005 |
| EP | 1 750 798 | 2/2007 |
| EP | 1 890 764 | 2/2008 |
| EP | 1 931 419 | 6/2008 |
| EP | 1 985 579 | 10/2008 |
| EP | 1 993 665 | 11/2008 |
| EP | 2 046 441 | 4/2009 |
| EP | 2 066 396 B1 | 6/2009 |
| EP | 2 069 003 | 6/2009 |
| EP | 2 131 916 | 12/2009 |
| EP | 2 167 188 | 3/2010 |
| EP | 2 320 221 | 5/2011 |
| EP | 2 341 979 | 7/2011 |
| EP | 2 456 513 A1 | 5/2012 |
| EP | 2 542 303 A1 | 1/2013 |
| EP | 2 559 454 A1 | 2/2013 |
| EP | 2 604 313 | 6/2013 |
| EP | 2 620 179 A1 | 7/2013 |
| EP | 2 623 154 A1 | 8/2013 |
| EP | 2 626 108 A1 | 8/2013 |
| EP | 2 626 109 A1 | 8/2013 |
| EP | 2 626 110 A1 | 8/2013 |
| EP | 2 626 111 A1 | 8/2013 |
| EP | 2 656 875 A1 | 10/2013 |
| EP | 2 656 876 A1 | 10/2013 |
| EP | 2 674 193 A1 | 12/2013 |
| WO | WO-98/10010 | 3/1998 |
| WO | WO-03/022354 | 3/2003 |
| WO | WO-03/028521 | 4/2003 |
| WO | WO-03/066152 | 8/2003 |
| WO | WO 03/066153 A2 | 8/2003 |
| WO | WO-03/066157 | 8/2003 |
| WO | WO-2004/045707 | 6/2004 |
| WO | WO-2005/002467 | 1/2005 |
| WO | WO-2005/067792 | 7/2005 |
| WO | WO-2005/112216 | 11/2005 |
| WO | WO-2006/104432 | 10/2006 |
| WO | WO-2007/002144 | 1/2007 |
| WO | WO-2007/009070 | 1/2007 |
| WO | WO-2007/011611 | 1/2007 |
| WO | WO-2007/025356 | 3/2007 |
| WO | WO-2007/028003 A2 | 3/2007 |
| WO | WO-2007/042999 | 4/2007 |
| WO | WO-2007/092330 | 8/2007 |
| WO | WO-2007/100428 | 9/2007 |
| WO | WO-2007/108718 | 9/2007 |
| WO | WO-2008/003318 | 1/2008 |
| WO | WO-2008/005478 | 1/2008 |
| WO | WO-2008/016881 | 2/2008 |
| WO | WO-2008/035285 | 3/2008 |
| WO | WO-2008/035344 | 3/2008 |
| WO | WO-2008/051463 | 5/2008 |
| WO | WO-2008/064269 A2 | 5/2008 |
| WO | WO-2008/068759 | 6/2008 |
| WO | WO-2008/075294 | 6/2008 |
| WO | WO-2008/077440 | 7/2008 |
| WO | WO-2008/089726 | 7/2008 |
| WO | WO-2008/107822 | 9/2008 |
| WO | WO-2008/109298 | 9/2008 |
| WO | WO-2008/133616 | 11/2008 |
| WO | WO-2008/133683 | 11/2008 |
| WO | WO-2008/138305 | 11/2008 |
| WO | WO-2010/014686 | 2/2010 |
| WO | WO-2010/055421 | 5/2010 |
| WO | WO-2011/115999 | 9/2011 |
| WO | WO-2013/014206 | 1/2013 |

OTHER PUBLICATIONS

US 8,469,885, 06/2013, Hafezi et al. (withdrawn)

Rousche, et al., "Flexible polyimide-based intracortical electrode arrays with bioactive capability," IEEE Transactions on Biomedical Engineering 48(3): 361-371 (Mar. 2001).

Sepulveda et al., "Finite Element Analysis of Current Pathways with Implanted Electrodes", J. Biomed. Eng. 1983, vol. 5, pp. 41-48.

International Search Report for PCT/EP2011/055045 dated Jul. 18, 2011 (4 pages).

(56) References Cited

OTHER PUBLICATIONS

U.S. Appl. No. 07/151,961, filed Feb. 3, 1988, Masahiko Okunuki et al.
Australian Patent Examination Report No. 1 dated Jan. 30, 2014 in corresponding Australian Application No. 2010326613, 2 pages.
Australian Patent Examination Report No. 1 dated Jan. 31, 2014 in corresponding Australian Application No. 2009315316, 3 pages.
Benabid, et al. "Combined (Thalamotomy and Stimulation) Stereotactic Surgery of the VIM Thalamic Nucleus for Bilateral Parkinson Disease", Proceedings of the Meeting of the American Society for Stereotactic and Functional Neurosurgery, Montreal 1987 Appl. Neurophysiol. 50: 344-346.
Canadian Office Action for Application No. 2,743,575 dated Sep. 25, 2014, 3 pages.
Cogan, Stuart F., et al. "Plasma-enhanced chemical vapor deposited silicon carbide as an implantable dielectric coating." Journal of Biomedical Materials Research Part A 67.3 (2003): 856-867.
Communication from the European Patent Office in Application No. 09795810.2 dated Sep. 14, 2011.
Decision of Rejection and Decision for Dismissal of Amendment in JP Patent Application No. 2011-543841 dated May 15, 2014.
EIC Biomedical, "Thin-film Encapsulation for Neural Recording and Stimulation Electrodes", Silicon carbide and oxycarbide, Apr. 2008: pp. 1-2.
English translation of Notice of Reasons for Rejection in JP application No. 2011-543841 dated Oct. 21, 2013.
European Communication and Search Report for Application No. 09795810.2 dated Sep. 25, 2013.
European Communication mailed May 22, 2013 including search report for EP application No. 12198290.4-1652.
European Search Report for Appl. Ser. No. 09803534.8 dated Jul. 21, 2011.
European Search Report for Appl. Ser. No. 13169272.5 dated Aug. 30, 2013.
European Search Report for application No. EP 14172592 dated Aug. 28, 2014, 8 pages.
Examination Report for EP09795810.2 dated Jun. 22, 2012.
Examination Report from European Patent Office in 09 795 810.2 dated May 8, 2014.
Examination Report in AU Patent Application No. 2009276603 dated Mar. 3, 2014.
Fierce Medical Devices, "Medtronic Announces First U.S. Implant of World's Smallest, Minimally Invasive Cardiac Pacemaker", Feb. 20, 2014, pp. 1-3.
Gibney, "St. Jude places its Nanostim leadless pacemaker in a U.K. patient", Fierce Medical Devices, Jan. 27, 2014, pp. 1-3.
International Preliminary Report on Patentability for PCT/EP2010/068658 dated Jun. 5, 2012.
International Preliminary Report on Patentability for PCT/IB2009/007715 dated May 17, 2011.
International Preliminary Report on Patentability for PCT/US2009/052077 dated Feb. 1, 2011.
International Search Report and Written Opinion for PCT/EP2010/068658 dated Mar. 21, 2011.
International Search Report and Written Opinion in PCT/US09/52077 dated Sep. 25, 2009.
International Search Report for PCT/IB2009/007715 dated Apr. 22, 2010.
Notice of Allowance for U.S. Appl. No. 14/287,917 dated Apr. 15, 2015.
Notice of Reasons for Rejection for Japanese Patent Application No. 2011-543841 dated May 30, 2013.
Notice of Reasons for Rejection in JP Patent Application No. 2011-521276 dated Mar. 3, 2014.
Notice of Reasons for Rejection in JP Patent Application No. 2011-521276 dated May 30, 2013.
Notice of Reasons for Rejections for Japanese Patent Appl. Ser. No. 2012-541491 dated Aug. 28, 2014, 8 pages.
Office Action for Canadian Appl. Ser. No. 2743575 dated Jan. 21, 2015 (4 pages).
Office Action for EPO Appl. Ser. No. 10787404.2 dated May 6, 2015.
Office Action for European Application No. 10787404.2 dated Mar. 26, 2013.
Office Action for Japanese Appl. Ser. No. 2013-501857 dated Jun. 1, 2015.
Office Action for Japanese Appl. Ser. No. 2013-501857 dated Sep. 17, 2014.
Pollak, et al. "Effets de la Stimulation du Noyau Sous-Thalamique Dans La Maladie De Parkinson", Rev. Neurol (Paris),149, 3, 175-176. Mason, Paris, 1993.
Second Notice of Reasons for Rejection for Japanese Application No. 2012-541491 mailed Apr. 8, 2015.
US Notice of Allowance for U.S. Appl. No. 14/316,154 dated Apr. 20, 2015.
US Notice of Allowance for U.S. Appl. No. 13/512,936 dated Feb. 20, 2014.
US Notice of Allowance for U.S. Appl. No. 13/512,936 dated Nov. 25, 2013.
US Notice of Allowance for U.S. Appl. No. 13/056,261 dated May 8, 2014.
US Notice of Allowance in U.S. Appl. No. 13/128,821 dated Dec. 24, 2013.
US Notice of Allowance in U.S. Appl. No. 13/128,821 dated Mar. 25, 2014.
US Office Action for U.S. Appl. No. 13/128,821 dated Dec. 14, 2012.
US Office Action for U.S. Appl. No. 13/128,821 dated Apr. 24, 2012.
US Office Action for U.S. Appl. No. 14/316,154 dated Dec. 18, 2014.
US Office Action for U.S. Appl. No. 13/512,936 dated Aug. 14, 2013.
US Office Action for U.S. Appl. No. 13/056261 dated Jan. 9, 2014.
US Office Action in U.S. Appl. No. 13/056,261 dated Aug. 7, 2013.
US Office Action on U.S. Appl. No. 14/287,917 dated Sep. 26, 2014.
Written Opinion for PCT/EP2010/068658 dated Jun. 1, 2012.
Written Opinion for Singapore Application No. 201103393-3 dated May 2, 2012.
Written Opinion of the International Search Authority for PCT/IB2009/07715 dated May 12, 2011.
Office Action for Canadian Appl. Ser. No. 2732309 dated Dec. 7, 2015.
US Notice of Allowance for U.S. Appl. No. 14/470,356 dated Apr. 13, 2016.
US Notice of Allowance for U.S. Appl. No. 14/470,356 dated Mar. 18, 2016.
US Office Action for U.S. Appl. No. 14/309,491 dated Mar. 3, 2016.
US Office Action for U.S. Appl. No. 14/470,423 dated Jan. 21, 2016.
US Office Action for U.S. Appl. No. 13/128,821 dated Nov. 14, 2013.
US Corrected Notice of Allowability for U.S. Appl. No. 14/470,356 dated May 18, 2016.
US Notice of Allowance for U.S. Appl. No. 14/309,491 dated May 11, 2016.
Decision of Rejection for Japanese Appl. Ser. No. 2012-541491 dated Oct. 26, 2015.
International Search Report and Written Opinion for PCT Appl. Ser. No. PCT/IB2015/053610 dated Jul. 20, 2015.
International Search Report and Written Opinion for PCT Appl. Ser. No. PCT/IB2015/056437 dated Nov. 5, 2015.
International Search Report and Written Opinion for PCT Ser. Appl. No. PCT/IB2015/056438 dated Nov. 5, 2015.
Office Action for Canadian Appl. Ser. No. 2743575 dated Jun. 11, 2015.
Office Action for Canadian Appl. Ser. No. 2743575 dated Sep. 14, 2015.
Office Action for EPO Appl. Ser. No. 14172592.9 dated Aug. 20, 2015.

(56) References Cited

OTHER PUBLICATIONS

US Notice of Allowance for U.S. Appl. No. 14/287,917 dated Jul. 20, 2015.
US Office Action for U.S. Appl. No. 14/309,491 dated Jul. 28, 2015.

* cited by examiner

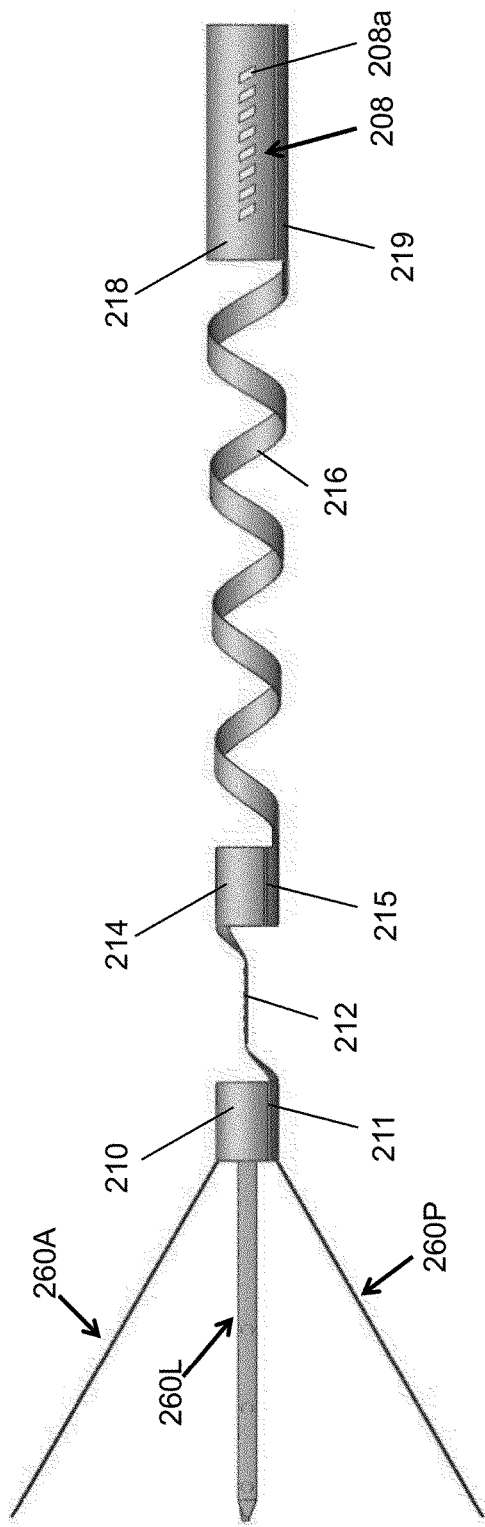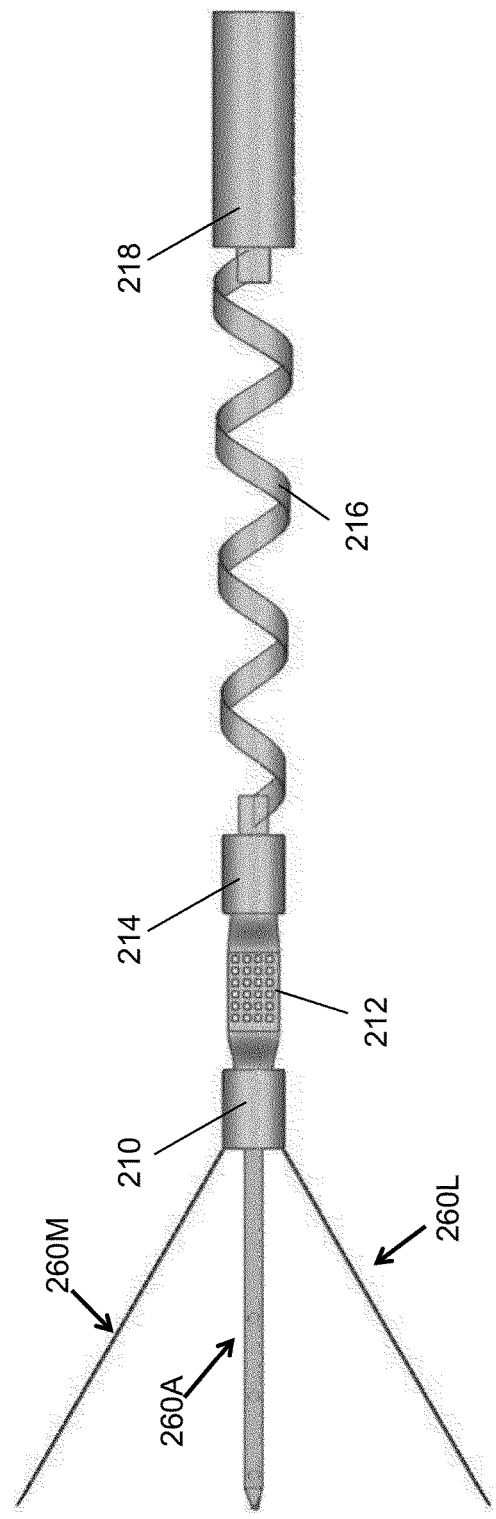
FIG. 8A
FIG. 8B

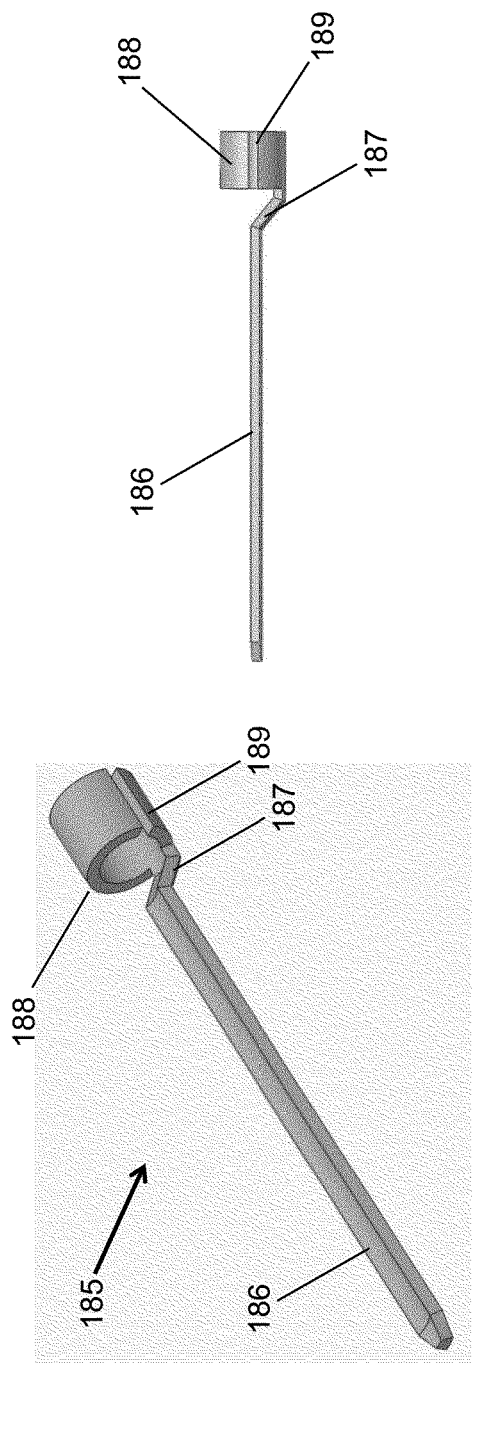
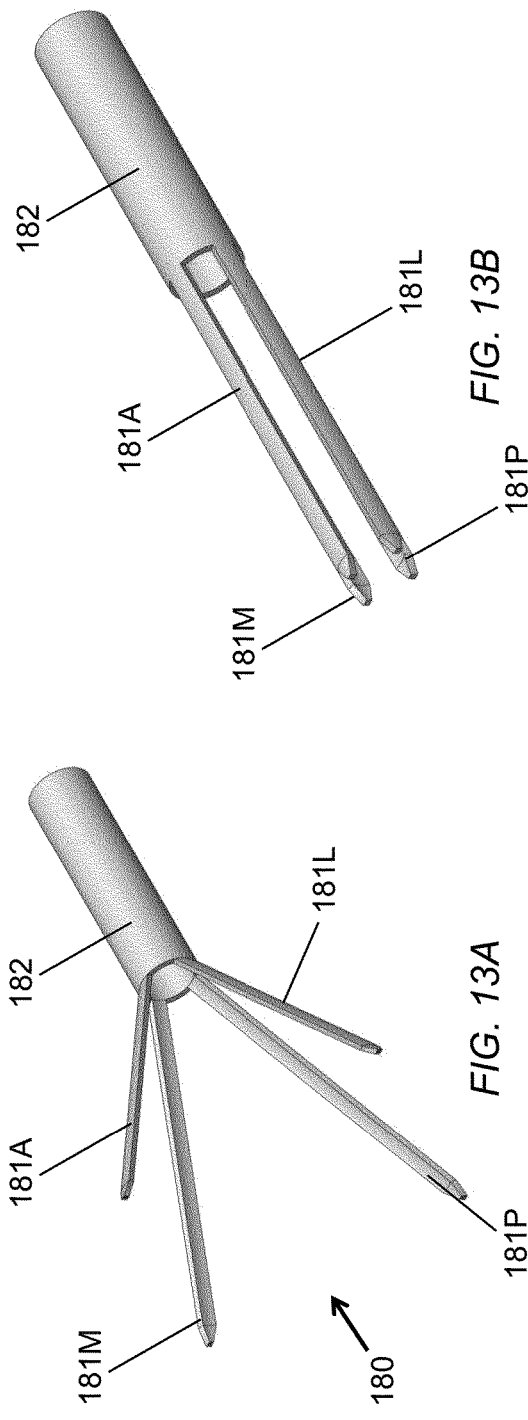
FIG. 12A
FIG. 12B
FIG. 13A
FIG. 13B

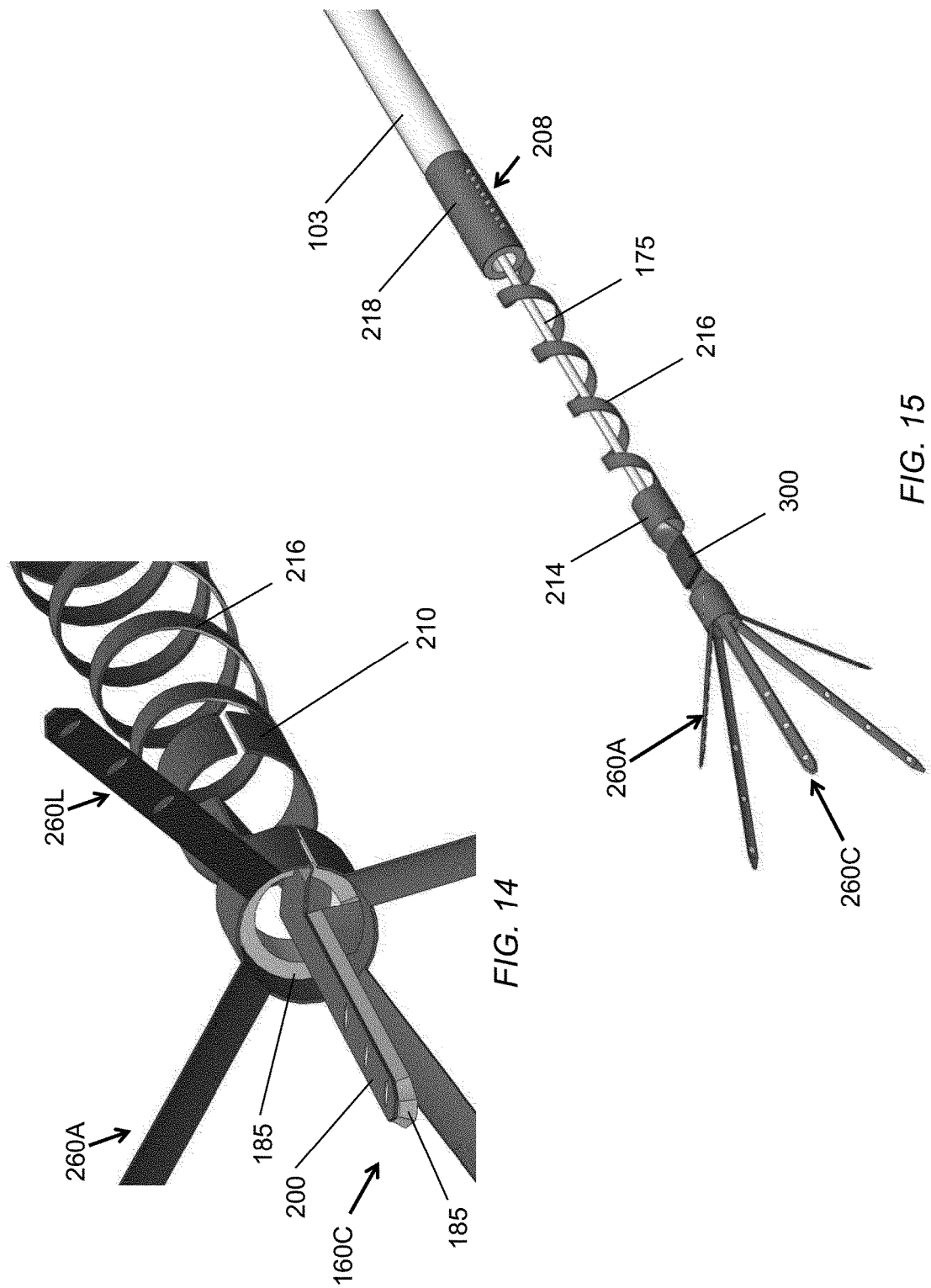

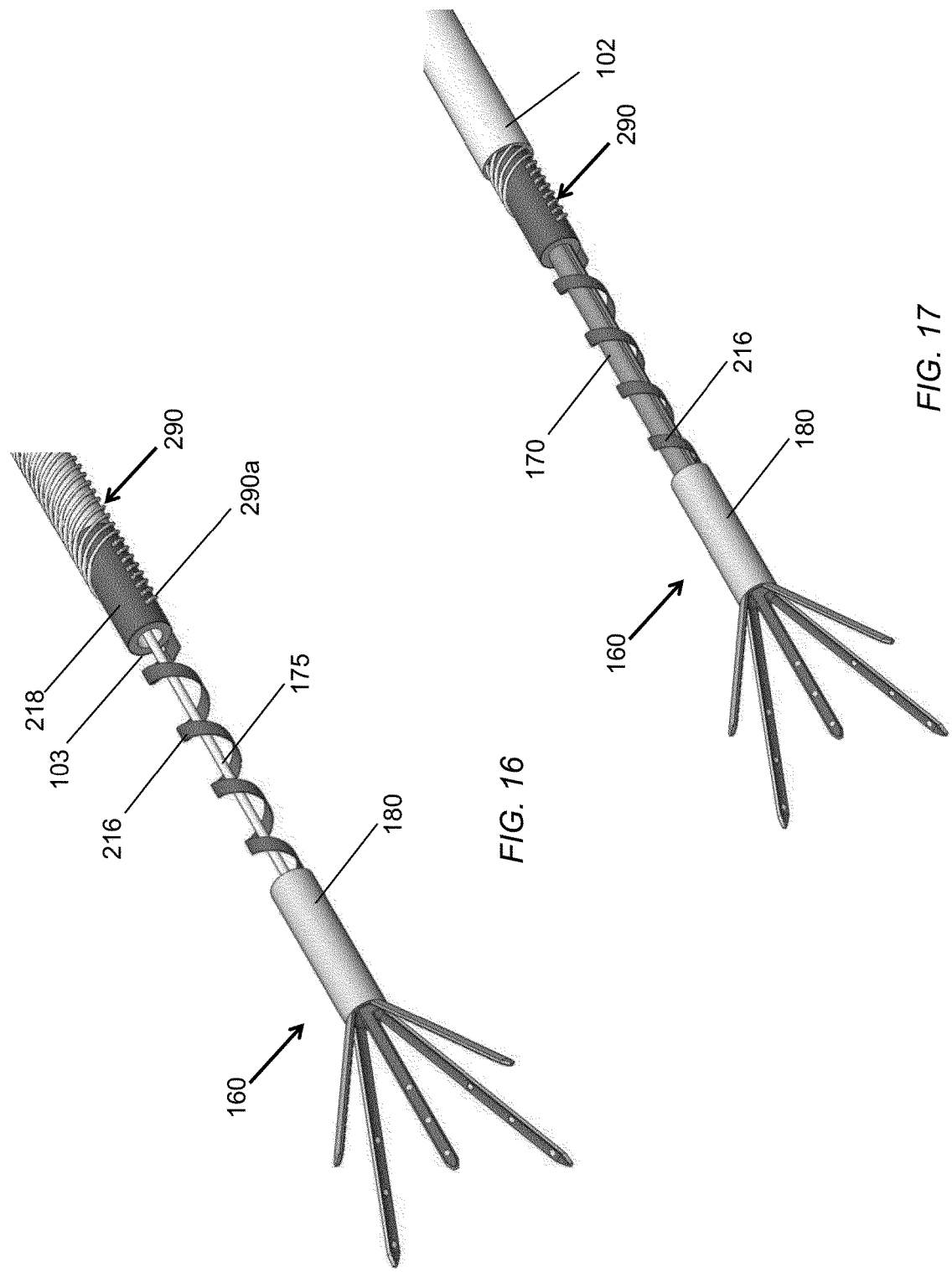

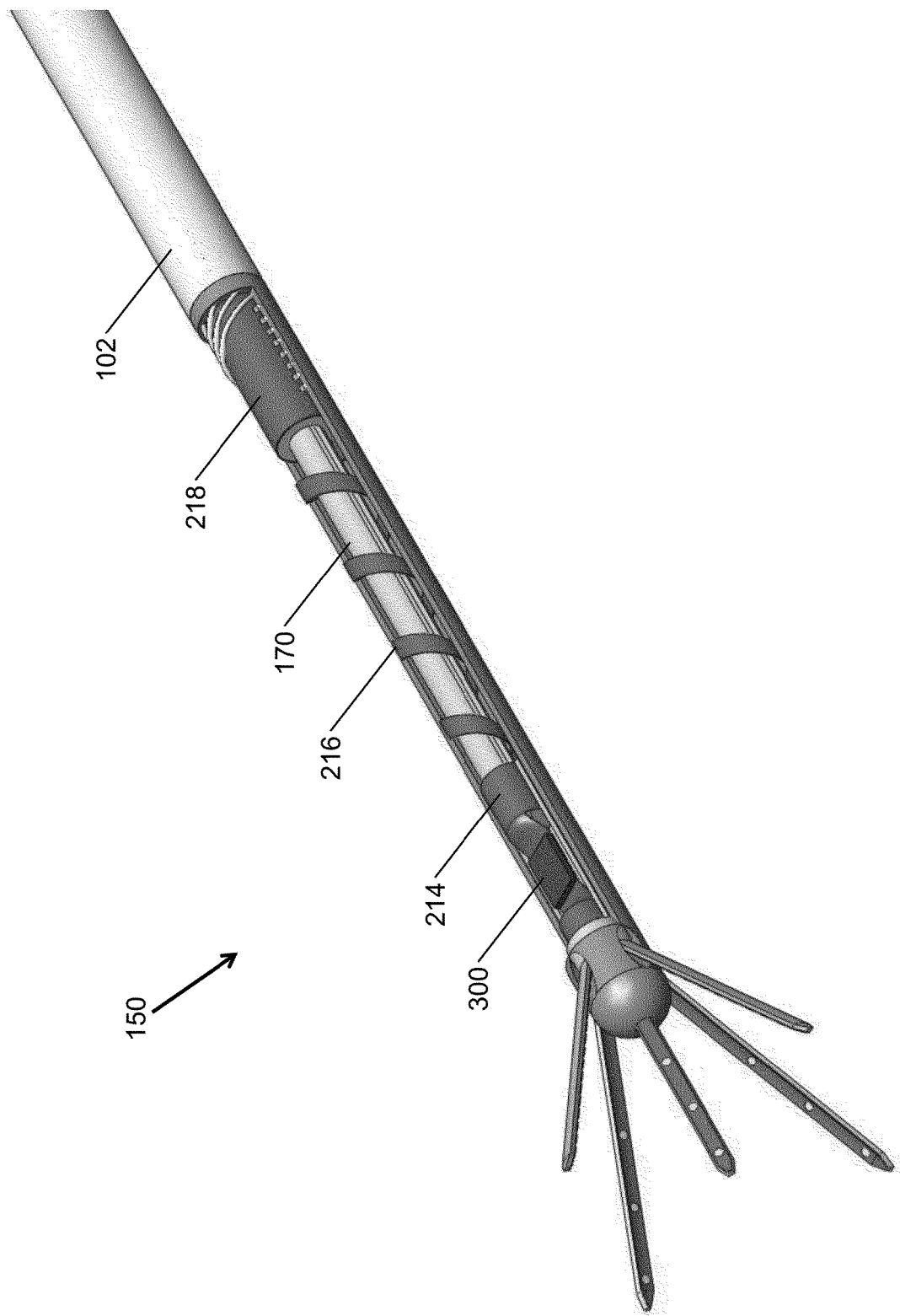

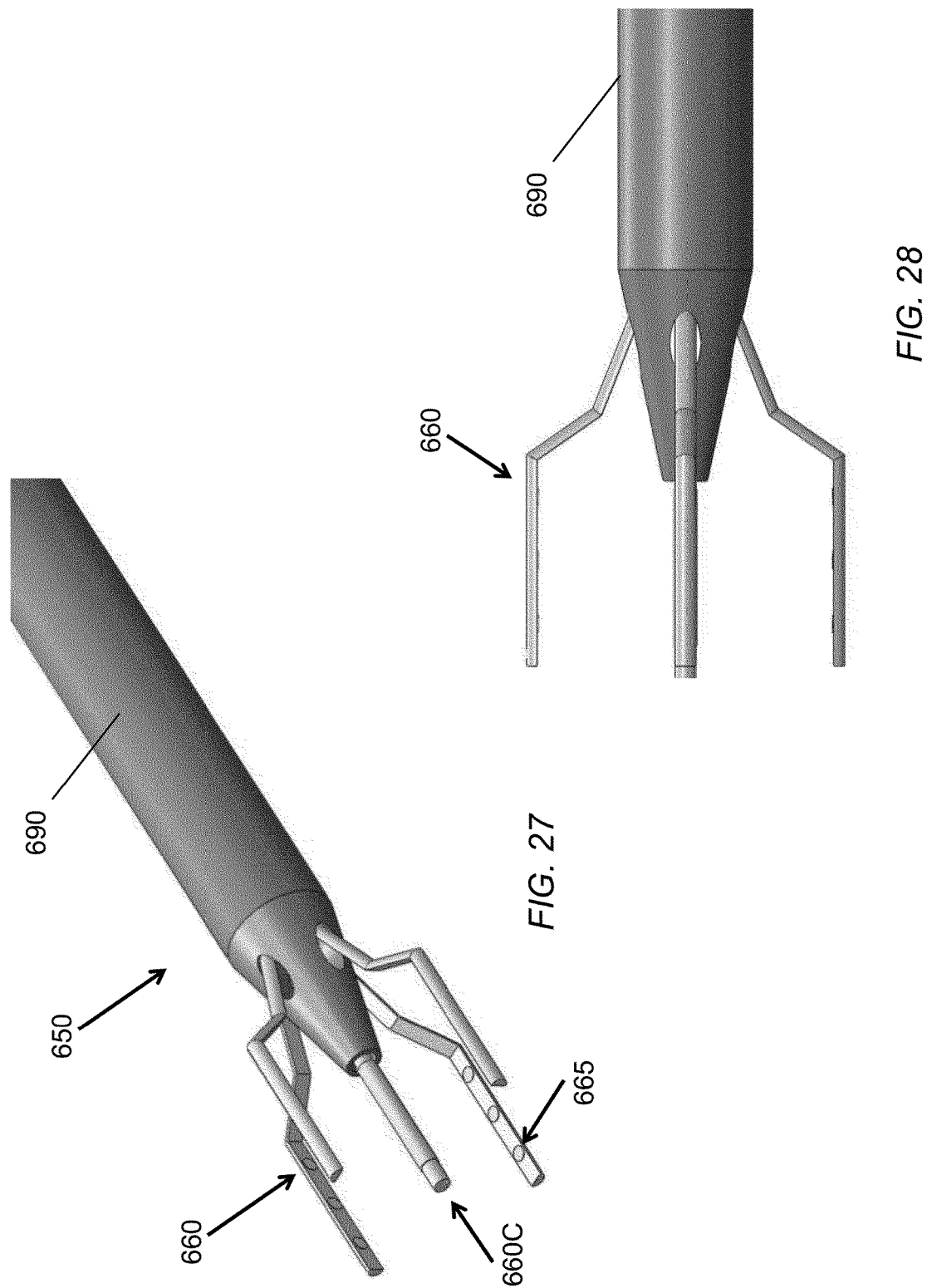

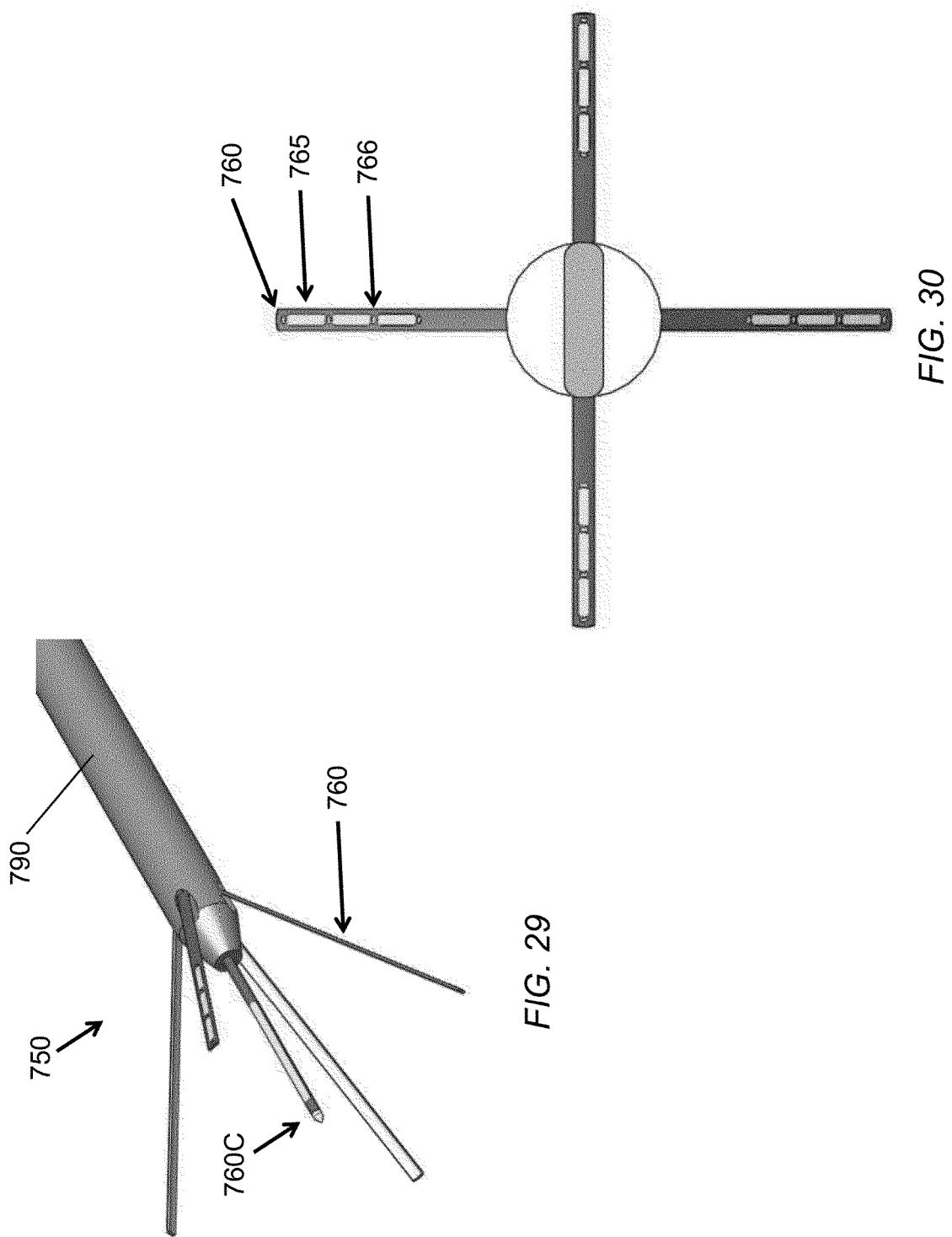

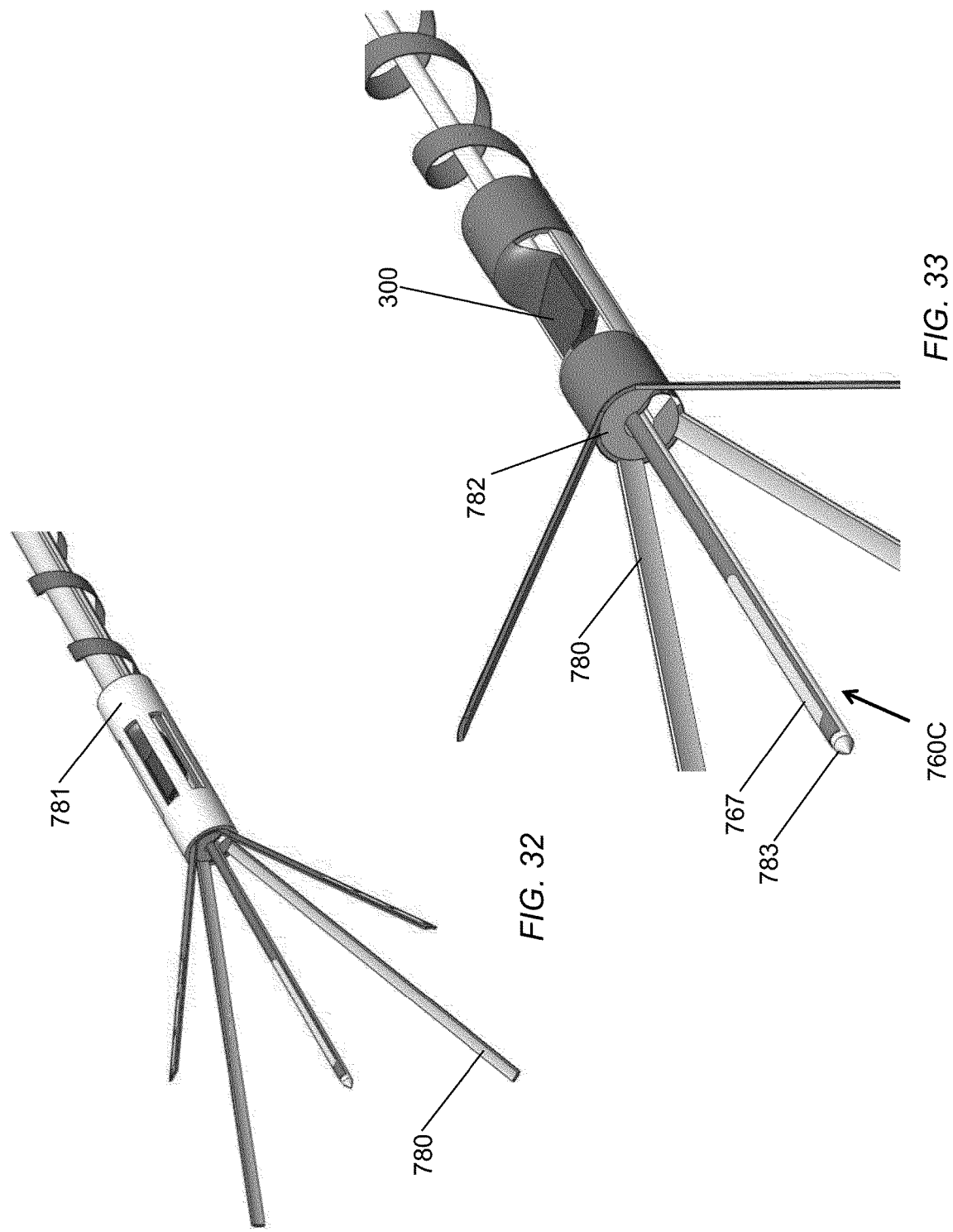

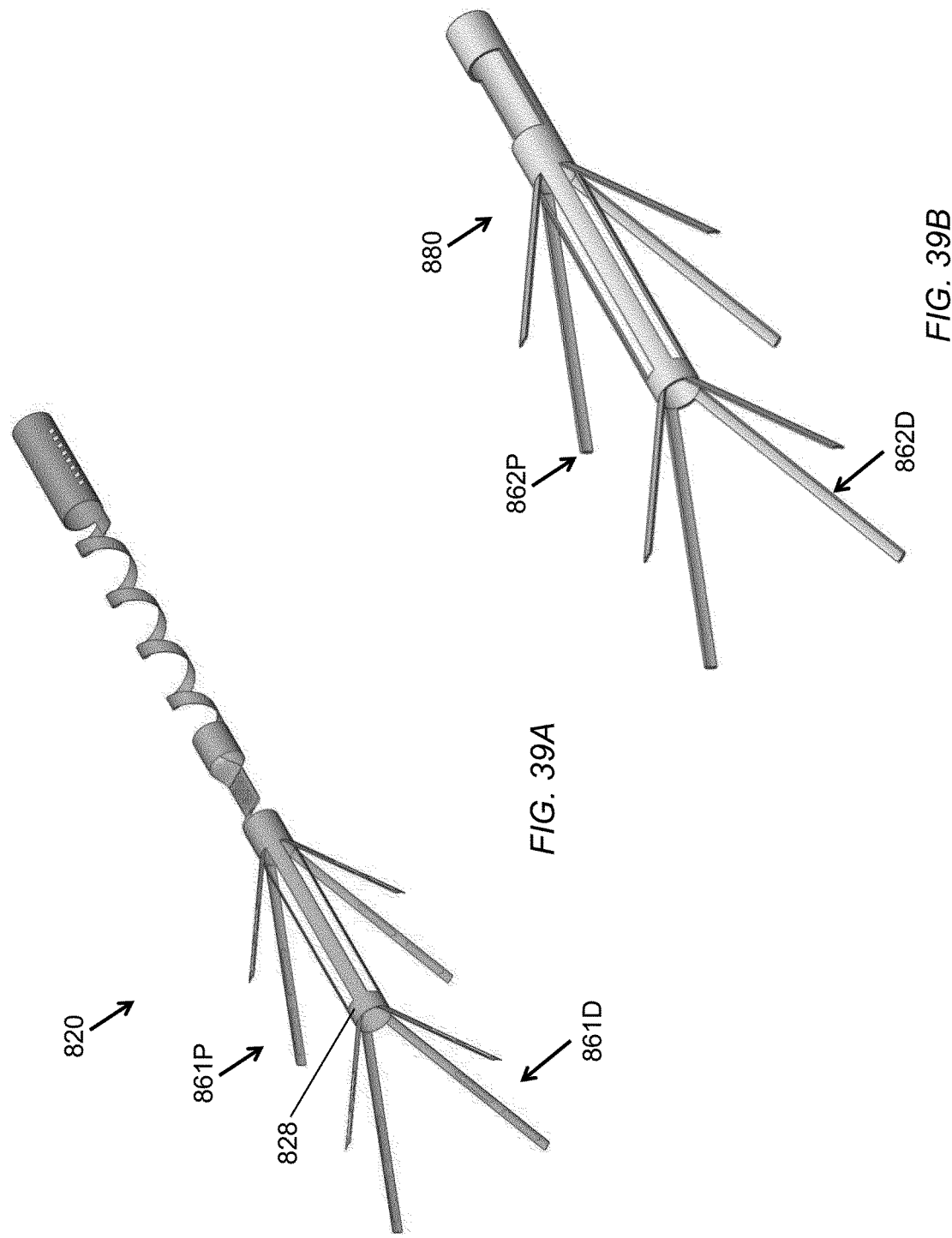

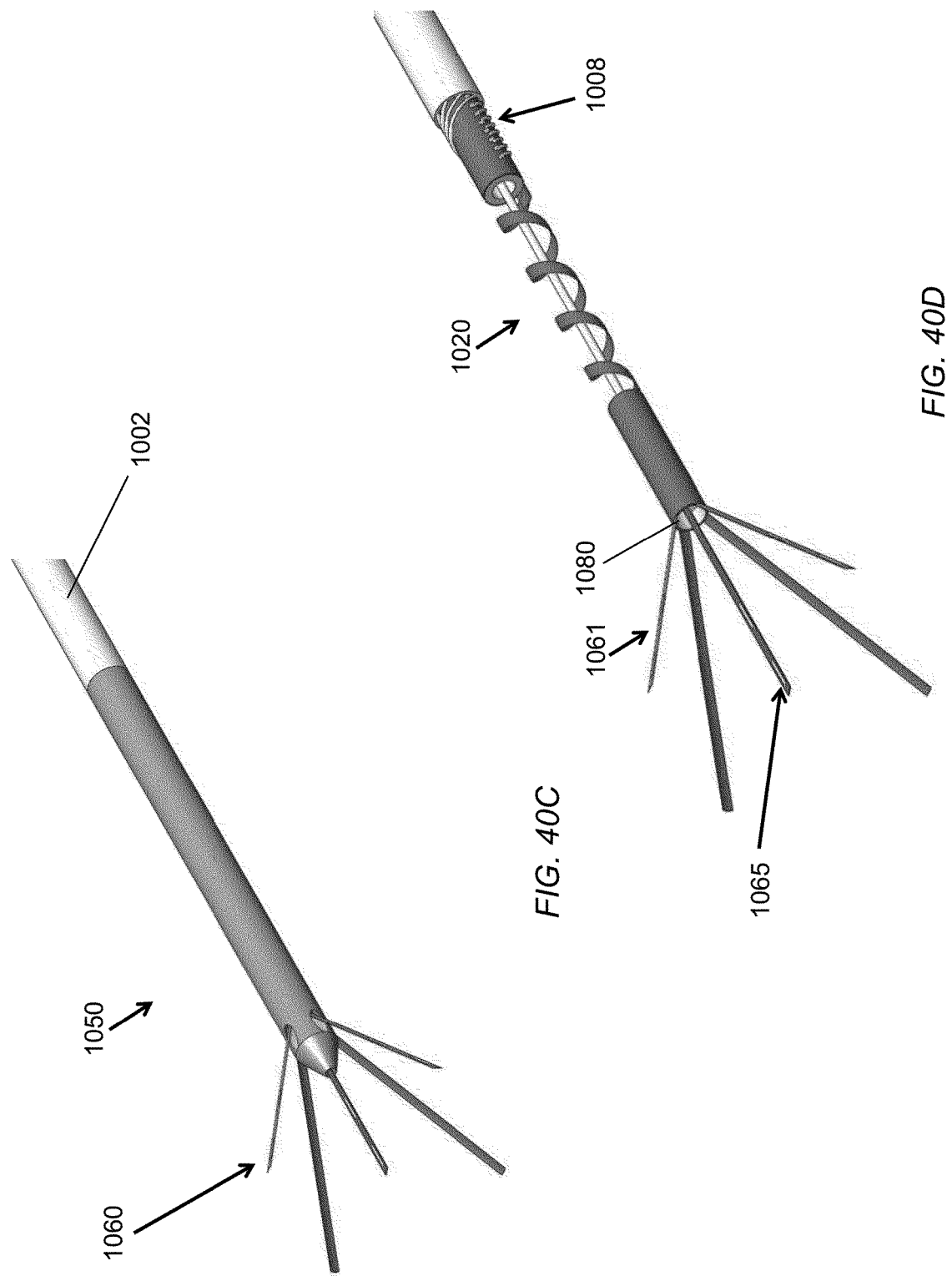

DEVICE FOR INTERACTING WITH NEUROLOGICAL TISSUE AND METHODS OF MAKING AND USING THE SAME

CROSS REFERENCE TO RELATED APPLICATIONS

The present application is a U.S. National Stage of PCT International Application Number PCT/EP2011/055045, filed Mar. 31, 2011, which claims priority to U.S. Provisional Application Ser. No. 61/320,089 filed Apr. 1, 2010, the entire contents of the foregoing applications are incorporated by reference herein.

FIELD

The present disclosure relates generally to field of interacting with biological tissue using electrical probes, and more particularly to interacting with a neurological target through the use of microelectrode probes.

BACKGROUND

Neural recording and neurostimulation are categories of medical devices that are used to interact electrically with tissue. In the case of neural recording, physiological measurements are performed of neurological tissue that can diagnose, or treat, a patient. In the case of neurostimulation, electric charge is transferred to the tissue in order to create a therapeutic outcome, or to generate a diagnosis. Neural recording and neurostimulation devices are used today in the cochlea, the retina, the peripheral nervous system, the spine, the brain, and other parts of the body.

In a particular application where both neural recording and neurostimulation are utilized, conductive electrodes are placed in contact with deep brain structures in order to treat certain neurological conditions. In the case of stimulating the Pedunculopontine Nucleus, for example, as described in U.S. Pat. No. 6,356,784, the therapy can treat the symptoms of Movement Disorders such as Parkinson's disease. In the case of stimulating Brodmann Area 25, for example, as described in U.S. Pat. No. 7,346,395, the therapy can treat the symptoms of Mood and Anxiety Disorders.

Generally, neural recording is performed in deep brain structures by surgically inserting conductive electrodes and amplifying neurological signals using external electronic equipment. Neurostimulation, is performed by surgically implanting conductive electrodes in the target, and using an implantable pulse generator to apply electrical signals to the conductive electrodes.

In some cases, such as described in U.S. Pat. No. 6,016,449, a system has been developed where both neural recording and neurostimulation functions are available in a single, long term implantable, device.

In most techniques, the electrodes used for neural stimulation that are placed in contact with tissue have been metallic, cylindrical, with very sharp distal ends. In most cases, they only contain one microelectrode, which severely limits the amount of physiological information that can be collected from the patient.

In other techniques, the electrodes used for neurostimulation that are placed in contact with tissue have been metallic, cylindrical, and relatively large in size (e.g., 1.27 mm in diameter and 1.5 mm in length). In most cases, there are four or eight cylindrical electrodes placed on a common axis. The stimulation methods are generally invasive, such as with the electrodes used in Deep Brain Stimulation, and the electrode lead is generally attached implantable pulse generator.

Furthermore, advances in micromachining technology have developed whole new applications for medical devices, and in particular, implantable devices such as for the treatment and diagnosis of neurological disorders.

Advances in the imaging of tissue have elucidated the function and anatomy of brain and nervous tissue, permitting the development of new therapies which include electrical stimulation methods. A number of research groups have reported on different approaches for imaging methods, and the construction of implantable devices to deliver therapies. The imaging methods are generally extra-corporeal, and involve large and/or sophisticated equipment such as Magnetic Resonance Imaging systems.

One of the great challenges for clinicians delivering electrical stimulation therapy is in localizing the correct location for electrode placement, and then confining the stimulation field to the appropriate anatomical target to deliver the therapy, without inducing side effects. Clinicians generally combine pre-operative navigational planning derived from Magnetic Resonance Imaging and/or Computed Tomography scan imaging systems, with intra-operative microelectrode recordings of electrophysiological phenomenon to find and locate the optimal target.

Volumes of anatomical interest are commonly found using microelectrode recording techniques which involve invasively inserting metal tips to find the area of interest by its electrophysiological activity. This may be uncertain, time consuming, and repetitive insertions may be hazardous to patient health.

Unfortunately, there are several limitations to current practice including uncertainty, discomfort for the patient, and a heavy financial burden to deliver the therapy. These factors can render the therapy less attractive to clinicians, patients and payers.

It would be a very useful advancement in the art of neural recording and neurostimulation device technology and in the practice of functional neurostimulation if the same device could image a volume of brain tissue, and stimulate the same volume of tissue with precision and safety.

There are many other medical applications for the present device, such as detecting malignant tissue within healthy tissue.

SUMMARY

The present disclosure provides a design and method which permit the imaging of small volumes of tissue along with the capability of stimulating precise areas within the volume of tissue. The imaging method presents an advancement over conventional methods that have relied on expensive and low resolution systems. The stimulation method presents an advancement over conventional techniques which have not permitted the precise steering of electrical fields into the optimal tissue activation volume required to deliver effective therapy. Combined, the imaging and stimulation method offers, for the first time, precise and high resolution stimulation of tissue in specific areas and volumes.

The disclosed devices and methods have special applications in medical use, particularly in the treatment of neurological disorders. Embodiments provide an unprecedented resolution in the imaging of tissue volumes by detecting local differences in electrical characteristics. In this way, some embodiments provide an imaging device, which while invasive and constrained in use, is able to provide a highly accurate registration of the imaged volume. The image registration permits the identification of anatomical structures, their surfaces and volumes, and their electrical characteristics such as, but not limited to, permittivity and conductivity.

When combined with stimulation methods, the device permits stimulation within specific regions, surfaces, and volumes of the registered image. The presently disclosed devices and methods provide the clinician and/or surgeon a tool by which they can both visualize the tissue of interest, and stimulate specific areas within it. This greatly increases the accuracy and safety of a surgery along with an improvement in the chronic therapeutic effects of stimulation.

The use of localized tomographical imaging to determine implant location and stimulation volume is a unique and important advancement in the field of neurological devices. Following the present disclosure, for the first time, clinicians will be able to substantially decrease the uncertainty in device placement, and increase the specificity of the location of stimulation.

The techniques described herein enjoy a number of advantages over conventional techniques to image tissue. Conventional methods in imaging require expensive equipment installations and resolution is increased by high field strengths in the case of Magnetic Resonance Imaging, or high X-ray dosages in the case of Computed Tomography scans. These high fields are not compatible with implantable devices containing metallic features, and artifacts caused by devices translate to image drift, errors, or decreased resolution in the registered image.

By bringing the imaging device into contact with the volume of interest, and measuring local differences in electrical characteristics of the volume, the some embodiments provide for images of unprecedented resolution and fidelity.

Likewise, the techniques for stimulation described herein enjoy a number of advantages over conventional efforts to stimulate tissue in a highly localized manner Conventional methods rely on implantable devices with electrical leads often composed of cylindrical contacts, or metal tips. Most methods rely on stimulation volumes extending only outwards from the device, as in the case of a cylindrical device.

One possible approach to this issue is the use of smaller electrodes, in order to stimulate with greater precision. However, there are practical limitations in surgery which prevent the clinician from precisely targeting the intended region. The image registration is often performed before the surgery, and subsequently navigational software is used to plan the implant trajectory and location. One approach is to incorporate the MRI into the surgery, and perform intra-operative imaging, however, this is economically unviable in many hospitals, and the low field strengths required to maintain compatibility with the implanted devices limit the resolution which can be achieved. For example, a surgeon would implant a cylindrical electrode lead after finding and confirming the stereotactic co-ordinates of the target site. As a more specific example, a neurosurgeon might implant an electrode lead in the Subthalamic Nucleus (STN) to treat the symptoms of Parkinson's Disease. The surgeon might not be able to easily find the STN, and even more commonly, might not be able to locate the area within the STN that they seek to stimulate using electric current. Furthermore, if the clinician seeks to stimulate only a specific area, surface, volume, or population of neurons or fiber bundles in, around, or near the STN, it would not be possible using today's technology because of the size and geometry of existing electrode leads, which are considerably larger than the aforementioned targets.

The presently disclosed devices and methods greatly improve current practice without fundamentally changing the surgical procedures currently in use. As an example, a neurosurgeon targeting the STN would implant the device using stereotactic co-ordinates very close to the STN. The surgeon would then deploy the several prongs from the device into and around the STN. The imaging method would be performed, which would provide the surgeon with a highly localized and high resolution image of the volume of tissue within the prongs of the device. The image will consist of a 2D or 3D tomography of the volume of tissue. The image is constructed using the differences in electrical characteristics of the volume such as, but not limited to, conductivity, permittivity, conductivity and/or permittivity anisotropy. The image can therefore provide information about, but not limited to, the location and direction of fiber tracts, neural cell density, the interface between grey and white matter. The image is created using electrical impedance tomography techniques which involve a sequence of steps by which current is applied between two electrodes and a potential difference is preferably detected across two different electrodes, or the same electrodes. By repeating this procedure across all the electrodes in the periphery of the imaged volume, an image can be registered with the tomographic data using any one of a number of image reconstruction techniques and algorithms.

Once the image has been registered, and the clinician can visualize what the device's exact location is, electrical stimulation can be applied to specific areas of the volume using the principles of neurostimulation and the superposition of electric fields. The clinician can then steer the stimulation field, and the volume of tissue activation, to particular areas of the volume. For example, the image might display the interface between the surface of the STN and fibers that are projecting from it, or to it. The clinician can then choose to stimulate this surface and the volume of activation is directed there by combining signals from several electrodes on the device prongs.

As a result, a previously inaccessible region can be quickly located, and stimulated, thereby decreasing surgical times and increasing the efficacy of treatment. In contrast, conventional devices were limited by the geometrical arrangement and size of electrodes, and by the lack of simultaneous or in-situ imaging when stimulating.

Another serious limitation to conventional devices is post-implantation movement. A patient that is reacting positively to the stimulation therapy might experience a movement of their electrode after implantation and thus, an immediate decrease or full halt in efficacy and the possible introduction of side effects. With the present device, if a device shift occurs, the volume of interest can be re-imaged, and the stimulation volume can be re-directed to the proper region.

The presently described devices and methods benefit from the ability of modern microfabrication techniques to facilitate the construction of the device. Recent advances in surface micromachining permit various electrode geometries consisting of favorable materials such as Platinum and Platinum-Iridium to be manufactured. The electrode substrates can then be assembled onto cut cylindrical components which consist of the prongs of the device. This assembly is further contained in an implantable catheter from which the prongs would extend during surgery.

In one aspect, an implantable neurological probe is disclosed including: an elongated probe assembly; at least one protruding shafts arranged at the distal end of the elongated probe assembly; a plurality of microelectrode elements arranged on the surface of the protruding shafts; at least one electrical contact arranged proximally along the elongated probe assembly; and at least one electrical conductor in electrical communication between at least one of the microelectrode elements and the at least one electrical contact.

In some embodiments, the protruding shafts can be reversibly retracted within the elongated probe assembly. In some embodiments, the elongated probe shaft is configured for insertion into a human body using an accepted procedure for insertion of deep brain stimulation leads. In some embodiments, the diameter of the elongated probe assembly is between 1 mm and 3 mm.

In some embodiments, at least one of the plurality of microelectrode elements is a stimulating electrode and at least one of the plurality of microelectrode elements is a detecting electrode. In some embodiments, at least one of the plurality of microelectrodes elements is both a stimulating electrode and a detecting electrode.

In some embodiments, each microelectrode element is formed on a conductive film, and where each microelectrode element is embedded within two isolating substrates. In some embodiments, the microelectrode embedded substrate is formable into a cylindrical assembly. In some embodiments, the protruding shafts can be formed to bend radial from the longitudinal axis of the cylindrical assembly. In some embodiments, one of the protruding shafts is longitudinal and centered along the longitudinal axis of the cylindrical assembly. In some embodiments, the protruding shafts are stiffened by a supporting member. In some embodiments, the longitudinal protruding shaft is stiffened by a supporting member.

In another aspect, a method for finding a neurological target including: implanting a neurological probe within a vicinity of a neurological target site, the neurological probe including an elongated cylindrical member, a plurality of protruding shafts, a plurality of microelectrode elements on each protruding shaft, at least one electrical contact arranged proximally along the probe shaft, and at least one electrical conductor in electrical communication between at least one of the plurality of the microelectrode elements and the at least one electrical contact; retracting the protruding shafts within the elongated cylindrical member before surgical implantation; expanding the protruding shafts in the vicinity of the neurological target site following implantation; recording electrophysiological signals from the neurological target site using at least one of the microelectrode elements on at least one of the protruding shafts; and stimulating the neurological target using at least one of the microelectrode elements on at least one of the protruding shafts.

In some embodiments, the protruding shafts are retracted within the elongated cylindrical member using a flexible pull wire situated in a lumen of the elongated cylindrical member. In some embodiments, the protruding shafts are expanded from within the elongated cylindrical member using a rigid, or semi-rigid, push rod situated in a lumen of the elongated cylindrical member. In some embodiments, the act of positioning the distal end of the neurological probe includes recording neural activity detected by at least one of the plurality of microelectrode elements and repositioning the distal end of the neurological probe as required, until the recorded activity is indicative of the distal end of the elongated probe shaft being located sufficiently at the neurological target site.

In some embodiments, the act of positioning the distal end of the neurological probe includes stimulating neural activity by applying electrical signals to at least one of the plurality of microelectrode elements on at least one of the plurality of protruding shafts, performing a clinical evaluation of the efficacy on the stimulation site in the implanted patient, and repositioning the distal end of the neurological probe as required, until the patient's response is indicative of the distal end of the elongated probe shaft being located sufficiently at the neurological target site.

In some embodiments, the act of positioning the distal end of the neurological probe includes inhibiting neural activity by applying electrical signals to at least one of the plurality of microelectrode elements on at least one of the plurality of protruding shafts, performing a clinical evaluation of the efficacy on the inhibition site in the implanted patient, and repositioning the distal end of the neurological probe as required, until the patient's response is indicative of the distal end of the elongated probe shaft being located sufficiently at the neurological target site.

In another aspect, a method is disclosed for finding a neurological target including: implanting a neurological probe within a vicinity of a neurological target site, the neurological probe including an elongated cylindrical member, a plurality of protruding shafts, a plurality of microelectrode elements on each protruding shaft, at least one electrical contact arranged proximally along the probe shaft, and at least one electrical conductor in electrical communication between at least one of the plurality of the microelectrode elements and the at least one electrical contact; retracting the protruding shafts within the elongated cylindrical member before surgical implantation; expanding the protruding shafts in the vicinity of the neurological target site following implantation; applying an oscillating electric current between at least two of the microelectrode elements on at least one of the protruding shafts; and detecting an electric voltage between at least two of the microelectrode elements on at least one of the protruding shafts.

In some embodiments, the act of applying oscillating currents and detecting electric voltages is performed to image the electrical characteristics of the volume of neurological tissue between the protruding shafts.

In another aspect, an implantable neurological probe is disclosed including: an elongated shaft having a distal end and an internal lumen; a support cylinder slidingly disposed in only a distal portion of the internal lumen; a plurality of shafts coupled to the support cylinder and arranged to be selectively extended from the distal end of the elongated shaft; a plurality of microelectrode elements disposed on each of the plurality of shafts, the microelectrode elements including a planar substrate having an insulative layer and a plurality of conductive traces disposed on the insulative layer, a stylet removably disposed in the internal lumen and configured to contact the support cylinder to selectively extend the plurality of shafts during implantation; and a pull wire coupled to the support cylinder to selectively retract the support cylinder and plurality of shafts within the internal lumen.

Some embodiments include a push-pull rod which includes the pull wire and the stylet.

In some embodiments, the elongated shaft is configured for insertion into a human body using an accepted procedure for insertion of deep brain stimulation leads.

In some embodiments, the diameter of the elongated shaft is between 1 mm and 3 mm.

In some embodiments, at least one of the plurality of microelectrode elements is a stimulating electrode and at least one of the plurality of microelectrode elements is a detecting electrode. In some embodiments, at least one of the plurality of microelectrodes elements is both a stimulating electrode and a detecting electrode.

In some embodiments, each microelectrode element is formed on a conductive film, and where each microelectrode element is embedded within two isolating substrates.

In some embodiments, the microelectrode embedded substrate is formable into a cylindrical assembly.

In some embodiments, the protruding shafts can be formed to bend radially from the longitudinal axis of the cylindrical assembly.

In some embodiments, one of the protruding shafts extends and is centered along the longitudinal axis of the cylindrical assembly.

In some embodiments, the protruding shafts are stiffened by a supporting member. In some embodiments, the longitudinal protruding shaft is stiffened by a supporting member.

In another aspect, an implantable neurological probe is disclosed including: an elongated shaft having a distal end and an internal lumen; a plurality of shafts arranged to be selectively extended from the distal end of the elongated shaft; and a plurality of microelectrode elements disposed on each of the plurality of shafts, the microelectrode elements including a planar substrate having an insulative layer and a plurality of conductive traces disposed on the insulative layer. In some embodiments, the plurality of shafts define a substantially cylindrical volume when fully extended.

In some embodiments, the elongated shaft is configured for insertion into a human body using an accepted procedure for insertion of deep brain stimulation leads.

In some embodiments, the diameter of the elongated shaft is between 1 mm and 3 mm.

In some embodiments, at least one of the plurality of microelectrode elements is a stimulating electrode and at least one of the plurality of microelectrode elements is a detecting electrode.

In some embodiments, at least one of the plurality of microelectrodes elements is both a stimulating electrode and a detecting electrode. In some embodiments, each microelectrode element is formed on a conductive film, and where each microelectrode element is embedded within two isolating substrates. In some embodiments, the microelectrode embedded substrate is formable into a cylindrical assembly. In some embodiments, the protruding shafts can be formed to bend radially from the longitudinal axis of the cylindrical assembly. In some embodiments, one of the protruding shafts extends and is centered along the longitudinal axis of the cylindrical assembly. In some embodiments, the protruding shafts are stiffened by a supporting member. In some embodiments, the longitudinal protruding shaft is stiffened by a supporting member.

In another aspect, a method is disclosed for finding a neurological target including: implanting a neurological probe within a vicinity of a neurological target site, the neurological probe including: an elongated shaft having a distal end and an internal lumen; a support cylinder slidingly disposed in only a distal portion of the internal lumen; a plurality of shafts coupled to the support cylinder and arranged to be selectively extended from the distal end of the elongated shaft; a plurality of microelectrode elements disposed on each of the plurality of shafts, the microelectrode elements including a planar substrate having an insulative layer and a plurality of conductive traces disposed on the insulative layer, a stylet removably disposed in the internal lumen and configured to contact the support cylinder to selectively extend the plurality of shafts during implantation; and a pull wire coupled to the support cylinder to selectively retract the support cylinder and plurality of shafts within the internal lumen. In some embodiments, the method further includes: retracting the plurality of shafts within the internal lumen before surgical implantation; extending the plurality of shafts in the vicinity of the neurological target site following implantation; recording electrophysiological signals from the neurological target site using at least one of the microelectrode elements on at least one of the protruding shafts; and stimulating the neurological target using at least one of the microelectrode elements on at least one of the plurality of shafts.

In some embodiments, the method includes: after the acts of recording and stimulating, retracting the plurality of shafts within the internal lumen and removing the neurological probe from a subject.

In some embodiments, the protruding shafts are retracted using the pull wire. In some embodiments, the plurality of shafts are extended using the stylet. In some embodiments, the neurological probe includes a push-pull rod which includes the pull wire and the stylet In some embodiments, the act of recording neurophysiological signals includes recording neural activity detected by at least one of the plurality of microelectrode elements and repositioning the distal end of the elongated shaft as required, until the recorded activity is indicative of the distal end of the elongated probe shaft being located sufficiently at the neurological target site.

Some embodiments include stimulating neural activity by applying electrical signals to at least one of the plurality of microelectrode elements on at least one of the plurality of shafts, performing a clinical evaluation of the efficacy on the stimulation site in the implanted patient, and repositioning the distal end of the elongated shaft as required, until the patient's response is indicative of the distal end of the elongated shaft being located sufficiently at the neurological target site.

Some embodiments include inhibiting neural activity by applying electrical signals to at least one of the plurality of microelectrode elements on at least one of the plurality of shafts, performing a clinical evaluation of the efficacy on the inhibition site in the implanted patient, and repositioning the distal end of elongated shaft as required, until the patient's response is indicative of the distal end of the elongated shaft being located sufficiently at the neurological target site.

In another aspect, a method is disclosed for finding a neurological target including: implanting a neurological probe within a vicinity of a neurological target site, the neurological probe including: an elongated shaft having a distal end and an internal lumen; a support cylinder slidingly disposed in only a distal portion of the internal lumen; a plurality of shafts coupled to the support cylinder and arranged to be selectively extended from the distal end of the elongated shaft; a plurality of microelectrode elements disposed on each of the plurality of shafts, the microelectrode elements including a planar substrate having an insulative layer and a plurality of conductive traces disposed on the insulative layer, a stylet removably disposed in the internal lumen and configured to contact the support cylinder to selectively extend the plurality of shafts during implantation; and a pull wire coupled to the support cylinder to selectively retract the support cylinder and plurality of shafts within the internal lumen. Some embodiments include retracting the plurality of shafts within the internal lumen before surgical implantation; expanding the plurality of shafts in the vicinity of the neurological target site following implantation; applying an oscillating electric current between at least two of the microelectrode elements on at least one of the plurality of shafts; and detecting an electric voltage between at least two of the microelectrode elements on at least one of the plurality of shafts.

Some embodiments include: after the act of detecting, retracting the plurality of shafts within the internal lumen and removing the neurological probe from a subject.

Some embodiments include imaging the electrical characteristics of the volume of neurological tissue between the plurality of shafts based on the applied oscillating electric current and the detected electric voltage.

In some embodiments, the neurological probe includes a push-pull rod which includes the pull wire and the stylet.

In another aspect, a method for finding a neurological target including: implanting a neurological probe within a vicinity of a neurological target site, the neurological probe including: an elongated shaft having a distal end and an internal lumen; a plurality of shafts arranged to be selectively extended from the distal end of the elongated shaft; and a plurality of microelectrode elements disposed on each of the plurality of shafts, the microelectrode elements including a planar substrate having an insulative layer and a plurality of conductive traces disposed on the insulative layer, where the plurality of shafts define a substantially cylindrical volume when fully extended. In some embodiments, the method includes: retracting the plurality of shafts within the internal lumen before surgical implantation; extending the plurality of shafts in the vicinity of the neurological target site following implantation; recording electrophysiological signals from the neurological target site using at least one of the microelectrode elements on at least one of the protruding shafts; and stimulating the neurological target using at least one of the microelectrode elements on at least one of the plurality of shafts.

In some embodiments, the protruding shafts are retracted using a pull wire. In some embodiments, he plurality of shafts are extended using a stylet. In some embodiments, the neurological probe includes a push-pull rod which includes the pull wire and the stylet.

In some embodiments, the act of recording neurophysiological signals includes recording neural activity detected by at least one of the plurality of microelectrode elements and repositioning the distal end of the elongated shaft as required, until the recorded activity is indicative of the distal end of the elongated probe shaft being located sufficiently at the neurological target site.

Some embodiments include: after the acts of recording and stimutating, retracting the plurality of shafts within the internal lumen and removing the neurological probe from a subject Some embodiments include stimulating neural activity by applying electrical signals to at least one of the plurality of microelectrode elements on at least one of the plurality of shafts; performing a clinical evaluation of the efficacy on the stimulation site in the implanted patient; and repositioning the distal end of the elongated shaft as required, until the patient's response is indicative of the distal end of the elongated shaft being located sufficiently at the neurological target site.

Some embodiments include inhibiting neural activity by applying electrical signals to at least one of the plurality of microelectrode elements on at least one of the plurality of shafts, performing a clinical evaluation of the efficacy on the inhibition site in the implanted patient, and repositioning the distal end of elongated shaft as required, until the patient's response is indicative of the distal end of the elongated shaft being located sufficiently at the neurological target site.

In another aspect, a method for finding a neurological target including: implanting a neurological probe within a vicinity of a neurological target site, the neurological probe including: an elongated shaft having a distal end and an internal lumen; a plurality of shafts arranged to be selectively extended from the distal end of the elongated shaft; and a plurality of microelectrode elements disposed on each of the plurality of shafts, the microelectrode elements including a planar substrate having an insulative layer and a plurality of conductive traces disposed on the insulative layer, where the plurality of shafts define a substantially cylindrical volume when fully extended. Some embodiment include retracting the plurality of shafts within the internal lumen before surgical implantation; expanding the plurality of shafts in the vicinity of the neurological target site following implantation; applying an oscillating electric current between at least two of the microelectrode elements on at least one of the plurality of shafts; and detecting an electric voltage between at least two of the microelectrode elements on at least one of the plurality of shafts.

Some embodiments include imaging the electrical characteristics of the volume of neurological tissue between the plurality of shafts based on the applied oscillating electric current and the detected electric voltage.

Some embodiments include: after the act of detecting, retracting the plurality of shafts within the internal lumen and removing the neurological probe from a subject Various embodiments may include any of the above described elements or steps alone, or in any suitable combination.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views.

FIG. 8A is a planar top view of the microelectrode array film assembly of FIG. 7.

FIG. 8B is a planar side view of the microelectrode array film assembly of FIG. 7.

FIG. 12A is a perspective view of a central pin component.

FIG. 12B is a planar side view of the central pin component of FIG. 12A.

FIG. 13A is a perspective view of the outer legs component shown in the expanded position.

FIG. 13B is a perspective view of the outer legs component shown in the retracted position.

FIG. 14 is a perspective view of the microelectrode array film assembly of FIG. 7 shown assembled to the central pin component of FIG. 12A.

FIG. 15 is a perspective view of the microelectrode assembly of FIG. 14 shown assembled to the flexible pull wire, and a microelectronic component.

FIG. 16 is a perspective view of the microelectrode assembly of FIG. 15 shown assembled to helical lead wires, and the outer legs component of FIG. 13A.

FIG. 17 is a perspective view of the microelectrode assembly of FIG. 16 shown assembled to an outer tubing and a stiff push rod.

FIG. 20 is a cut-away perspective view of the microelectrode assembly of FIG. 4A with segments of the perforated end cap and outer legs component removed.

FIG. 27 is a perspective view of an alternative embodiment of the elongated microelectrode assembly of FIG. 1.

FIG. 28 is a planar side view of the alternative embodiment of FIG. 27.

FIG. 29 is a perspective view of an alternative embodiment of FIG. 1 where the microelectrode arrays are placed on the outside of the protruding shafts.

FIG. 30 is a planar back view of the alternative embodiment of FIG. 29.

FIG. 32 is a detail perspective view of the alternative embodiment of FIG. 29.

FIG. 33 is an additional detail perspective view of the alternative embodiment of FIG. 29.

FIG. 39A is a perspective view of the microelectrode array film required in the assembly of the alternative embodiment of FIG. 37.

FIG. 39B is a perspective view of the protruding shaft support required in the assembly of the alternative embodiment of FIG. 37.

FIG. 40C is a perspective view of an alternative embodiment of FIG. 1 where the protruding shafts are not rigidified by the protruding shaft support.

FIG. 40D is a detail perspective view of the alternative embodiment of FIG. 40C.

DETAILED DESCRIPTION

Figure 1:
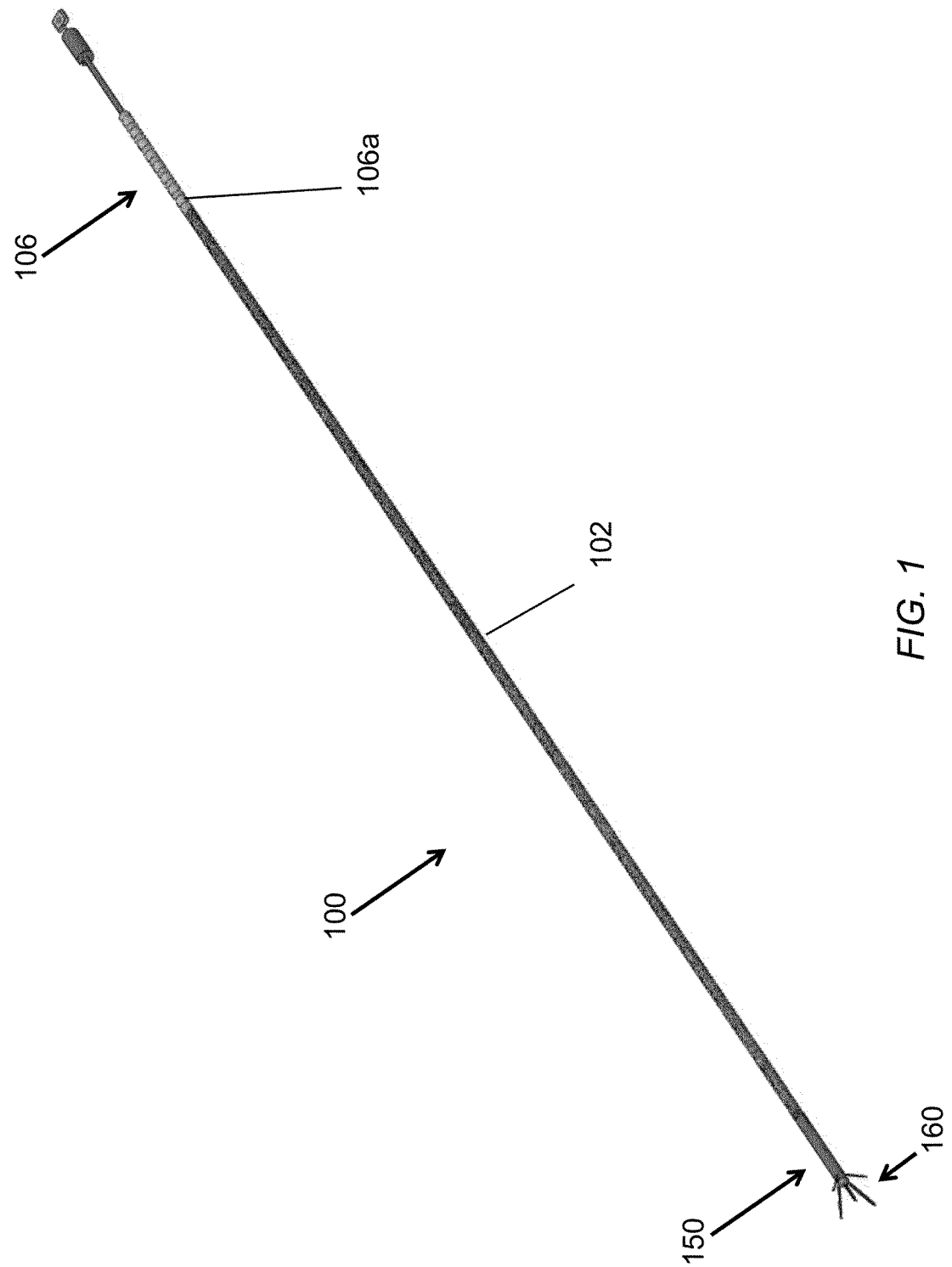
FIG. 1 is a perspective view of one embodiment of an elongated microelectrode assembly.

Described herein are microelectrode array devices, and methods of fabrication and use of the same, to provide highly localized and efficient electrical stimulation of a neurological target, such as individual neurons, groups of neurons, and neural tissue as may be located in an animal nervous system, such as deep within a human brain. In small, difficult to find brain targets such as the Pedunculopontine Nucleus, or in targets that requires highly localized levels of neural stimulation, such as the Subthalamic Nucleus, many microelectrodes are required in the brain region to find the target using electrophysiological recording. A higher number of microelectrodes will increase the chance of finding the neurons required for therapeutic stimulation. The microelectrode, or group of microelectrodes, that are closest to the target brain region will be used for chronic, therapeutic stimulation or inhibition.

The stimulation can be highly localized, because the microelectrode elements can be as small as only 2 µm or large as 2 mm in either of diameter or width. The relative spacing between such microelectrode elements can also be as small as only 2 µm or as large as 2 mm Generally, microelectrodes of about 150 µm in diameter, with about a 1000 µm spacing are particularly efficient in stimulating neural tissue.

An array of such microelectrode elements may consist of one or more such elements (e.g., sixteen elements), each disposed at a respective position, or site. This is in contrast to currently available stimulation leads, such as the Model 3387 or Model 3389 DBS leads commercially available from Medtronic, Inc. of Minneapolis, Minn. Such commercially available devices include relatively large, cylindrical electrodes measuring about 1.5 mm in height, and having a maximum of only four electrodes in use today for deep brain stimulation.

Smaller microelectrode elements can be used to provide neurological stimulation that is highly localized and efficient because an array of such microelectrodes can also be used to identify the stimulation region of interest. For example, one or more microelectrode elements of such an array of microelectrode elements can be used to record neuronal activity in the vicinity of the detecting/recording microelectrode elements. Such refinement offered by the relatively small size and/or spacing of the microelectrode elements can be used to obtain a highly localized map of neuronal activity in the region surrounding the implant. A suitably dimensioned microelectrode array having multiple microelectrode elements positioned in a general vicinity of a neurological target, can be used to locate a precise neurological target without further repositioning, by identifying those one or more microelectrode elements located in a very specific region of the neurological target. The microelectrode array can be programmed to stimulate in a very specific region, for example, using only a certain number of the microelectrode elements to actively stimulate the surrounding neurons and/or neuronal tissue, while other electrode elements of the array remain inactive.

In the embodiments described, the microelectrode arrays are positioned in three dimensional space. This has been a previous limitation of such microelectrode devices, which were usually implement in linear arrays, or two dimensional arrays on films. In the present embodiment microelectrode arrays are positioned along shafts which radiate from a central lumen, in order to cover as much volume in the target region with microelectrode arrays.

In some embodiments, an elongated device including such microelectrode arrays having elements with relatively small size and/or spacing can be used to obtain a highly localized map of neuronal activity in the region surrounding the implant. For example, such a device configured with a linear array of microelectrodes positioned along a length of a distal end of the device can be placed into a patient's brain. Preferably, the elements of the microelectrode array envelop a region including the neurological target. Neurological activity can then be independently detected by one or more of the microelectrode elements. The detected activity may be captured in a recorder or display device, allowing a clinician to identify which one or more of the microelectrode elements is positioned closest to the intended target. Knowing a respective location of each of the microelectrode elements along the device, and determining the distance to a reference, such as the patient's skull, a precise location of the target can be determined as the distance along a trajectory of the device, measured from the reference to the particular microelectrode element. Beneficially, location of the target can be determined without any repositioning of the elongated device, thereby simplifying the medical procedure and reducing patient risk.

In some embodiments, the device is for acute intra-surgical use, being removed after the target has been located, being replaced with a chronic probe, positioned at the determined target location. Alternatively or in addition, the device itself can be left in place as a chronic device, the same microelectrodes, or different ones, being used to record and/or stimulate the neurological target over an extended period.

One embodiment of a microelectrode device illustrated in FIG. 1 includes an elongated microelectrode lead assembly 100 sometimes referred to as an electrode lead. The microelectrode lead assembly 100 includes an external cylindrical member 102 including a microelectrode array assembly 150 located relative to a distal end and one or more electrical contacts 106 located relative to a proximal end. The exemplary microelectrode lead assembly 100 includes one or more microelectrode array shafts 160 adjacent to its distal tip. The microelectrode array assembly 150 has five protruding shafts 160, with disc microelectrode elements disposed along an interior surface of an extended substrate. In the present embodiment four shafts protrude, to one of the anterior, posterior, lateral, or medial directions. An additional shaft protrudes along the same longitudinal axis of the electrode lead, referred to as the central shaft. The microelectrode lead assembly 100 also includes eight electrically conductive, cylindrical contacts, or contact rings (generally 106) distributed along a longitudinal axis of the proximal end of the assembly 100. In the exemplary embodiment, each of the microelectrode elements is in electrical communication with a proximal contact 106 via an embedded microelectronic element. In use, stimulation signals are directed from an implantable pulse generator, or controller to the microelectrode array. Additionally, in use, recording signals are directed from the microelectrode array to an implanted or external data recorder.

The microelectrode lead assembly 100 is preferably sized and shaped for its intended neurological application. For example, the microelectrode lead assembly 100 may be at least partially placed within the central nervous system. Alternatively or in addition, the microelectrode lead assembly 100 may be at least partially placed within other parts or organs of the body, such as the epidural space of the spine, or other locations within the peripheral nervous system, or within an organ such as the liver or heart. Thus the diameter and length of the microelectrode lead assembly 100 may vary depending on the particular anatomical target. Additionally, the configuration of the microelectrode array shafts 160 is also sized and shaped for an intended neurological target. The number, shape, orientation, size, and spacing of the microelectrode elements of the array can be defined in response to the intended neurological target.

In at least some embodiments one or more of the microelectrode elements are sized and or spaced to record from and/or stimulate neurons. The microelectrode lead assembly 100 can be used to detect and/or record neuronal activity at the neurological target. Neuronal activity naturally occurring within the neurological target gives rise to local electromagnetic fields that can be detected by one or more of the microelectrode elements of the microelectrode array. For example, electric fields produced by neurons will polarize one or more of the microelectrode elements. Such polarization gives rise to an electrical potential with respect to a reference, such as electrical ground, or another one of the microelectrode elements. Such electric activity can be further conducted to one or more of the cylindrical contacts 106 through the internal electrical conductors. One or more of the cylindrical contacts 106, in turn, can be connected to one or more additional medical devices for further processing of the detected electrical activity. For example, the cylindrical contacts 106 can be coupled to a display device or recording device for displaying and/or recording electrical activity from the neurological target.

Alternatively or in addition, one or more of the microelectrode elements can be used to electrically stimulate the neurological target. For example, one or more externally generated electrical signals can be applied to one or more of the cylindrical contacts 106. These electrical signals can be conducted through the internal electrical conductors to one or more of the microelectrode elements of the microelectrode array. Depending on the amplitude and polarity of the electrical signals, an electrical field will be induced by the polarized microelectrode elements. Electrical fields induced by such polarization can interact with one or more neurons at the neurological target.

Alternatively or in addition, one or more of the microelectrode elements can be used to perform Electrical Impedance Tomography of a neurological target or other bodily organ. For example, one or more externally generated electrical signals can be applied as a current to one or more of the microelectrode elements. Depending on the physiological characteristics of the tissue being imaged, and depending on the frequencies of the current signals applied, an electrical field will be induced in the tissue. Electrical fields induced by such polarization can be detected by other microelectrode elements, thereby creating a localized image of conductivity, permittivity, and/or other electrical characteristics.

Mechanical components of the implantable neurological lead assembly 100 include the elongated outer cylindrical member 102, which can be a simple polymeric cylinder, or a rigid metallic or rigid polymeric cylinder. The outer cylindrical member 102 can vary in length and diameter but is generally at least about 28 cm long, (e.g., at least 20 cm long, at least 25 cm long, at least 28 cm long, at least 30 cm long, etc.) and around 1.27 mm in diameter (e.g., in the range of 1.0-2.0 mm in diameter).

The neurological lead 100 can be implanted near a neurological target, such as a target brain structure, using common neurosurgical techniques such as stereotaxy or endoscopy. The microelectrode lead assembly 100 can be inserted in its retracted state without support, or within a supporting cannula having an inner dimension slightly larger than the outer dimension of the device. The cannula, when used, would be removed once the microelectrode lead assembly 100 has been suitably positioned. In some embodiments a lumen along the axis of the outer cylindrical member 102 permits the insertion of a rigid stylet which renders the microelectrode lead assembly 100 rigid during surgical implantation. This is particularly helpful during insertion, positioning and repositioning of flexible embodiments of the microelectrode lead assembly 100. The stylet is removed after implantation leaving the probe in its surgical target. In some embodiments the stylet is also a rigid push rod, which is used to expand the microelectrode array shafts 160 into the tissue. In some embodiments, the microelectrode lead assembly 100 contains a flexible pull wire which is used to pull the microelectrode array shafts 160 back into the retracted position. In yet additional embodiments, the microelectrode lead assembly 100 contains only one rigid push-pull rod which is used to both push and pull the microelectrode array shafts 160 in its expanded and retracted position respectively. In yet additional embodiments, where the microelectrode lead assembly 100 is not intended to remain in the patient's brain after surgery, the rigid push-pull rod may be permanently attached to the microelectrode array shafts 160.

A clinician can connect one or more of the microelectrode elements to a display unit or a recording unit through the cylindrical contacts 106. The recording unit, not shown, allows a clinician to identify certain regions of the brain according to their electrical activity. In some embodiments, such recording information can be processed automatically, through the use of a suitably programmed computer processor. The electrodes used to record from the brain can be the same electrodes as those used to stimulate tissue. The recording electrodes can also be separate from those used to stimulate the brain. This situation might be preferred because electrodes destined for recording may be different in size and design than those for stimulation.

The operator can connect the electrodes to an external stimulation source or an implantable source. In either instance, the source can include a pulse generator for applying signals to the electrode sites. The signals from such a pulse generator can be connected directly to the electrodes, or they can be preprocessed using electronics embedded in the device. The electronics can filter certain parts of the original signal. If there are more electrodes than signals, the electronics can route or otherwise interconnect the stimulation source as necessary.

Figure 2:
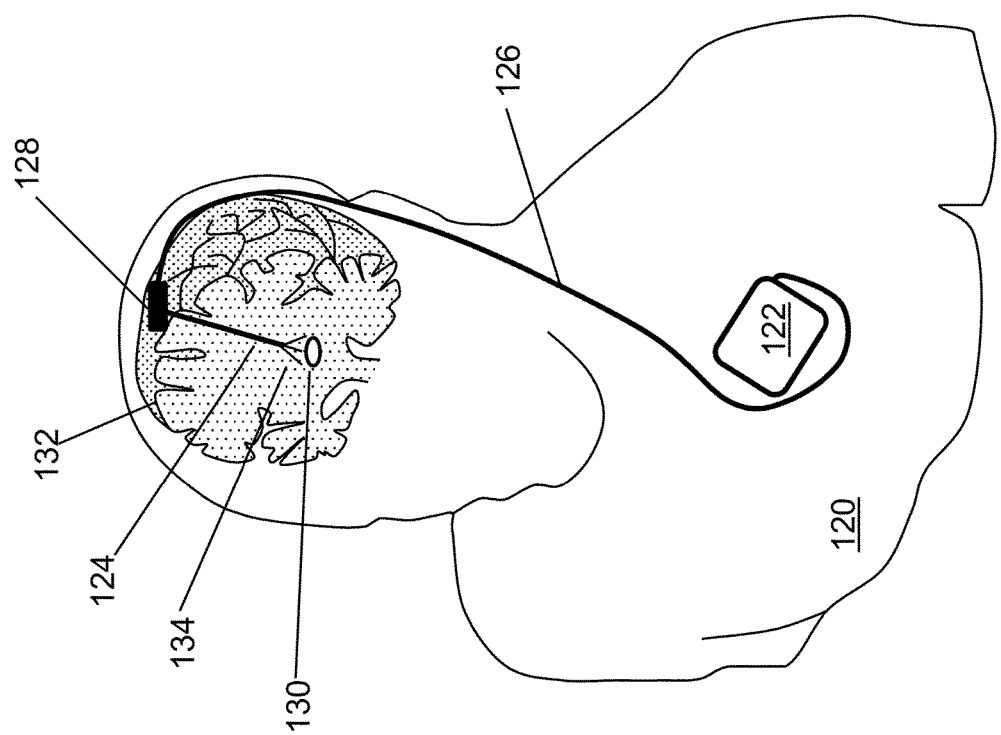
FIG. 2 is a perspective view of a portion of a human anatomy illustrating an exemplary elongated microelectrode assembly implanted therein.

A perspective view of the portion of a human anatomy is illustrated in FIG. 2, showing implantation of an exemplary elongated microelectrode probe assembly 124 position for interaction with a neurological target located deep within the brain. A distal portion of the microelectrode probe assembly 124 is positioned at the neurological target 130, in this instance located within the human brain 132. Several exemplary microelectrode array shafts 134 protrude from the distal portion of the microelectrode probe assembly 124. In some embodiments the proximal end of the microelectrode probe assembly 124 is connected to a first medical device 128. For example, the first medical device 128 may include an electronic assembly implanted external to the brain 132 to minimize invasion into the body. Alternatively or in addition, a second medical device, which again may include an electronic assembly such as a pulse generator 122 can be implanted at a remote portion of the subject body. As shown, a second electronic assembly 122 is implanted within a chest cavity 120. When one or more medical devices, such as the exemplary pulse generator 122 are located remotely in this manner, a cable 126 may also be implanted within the subject's body to interconnect the pulse generator 122 to the electronic assembly 128, when present or directly to cylindrical contacts located at the proximal end of the microelectrode probe assembly 124.

Figure 3:
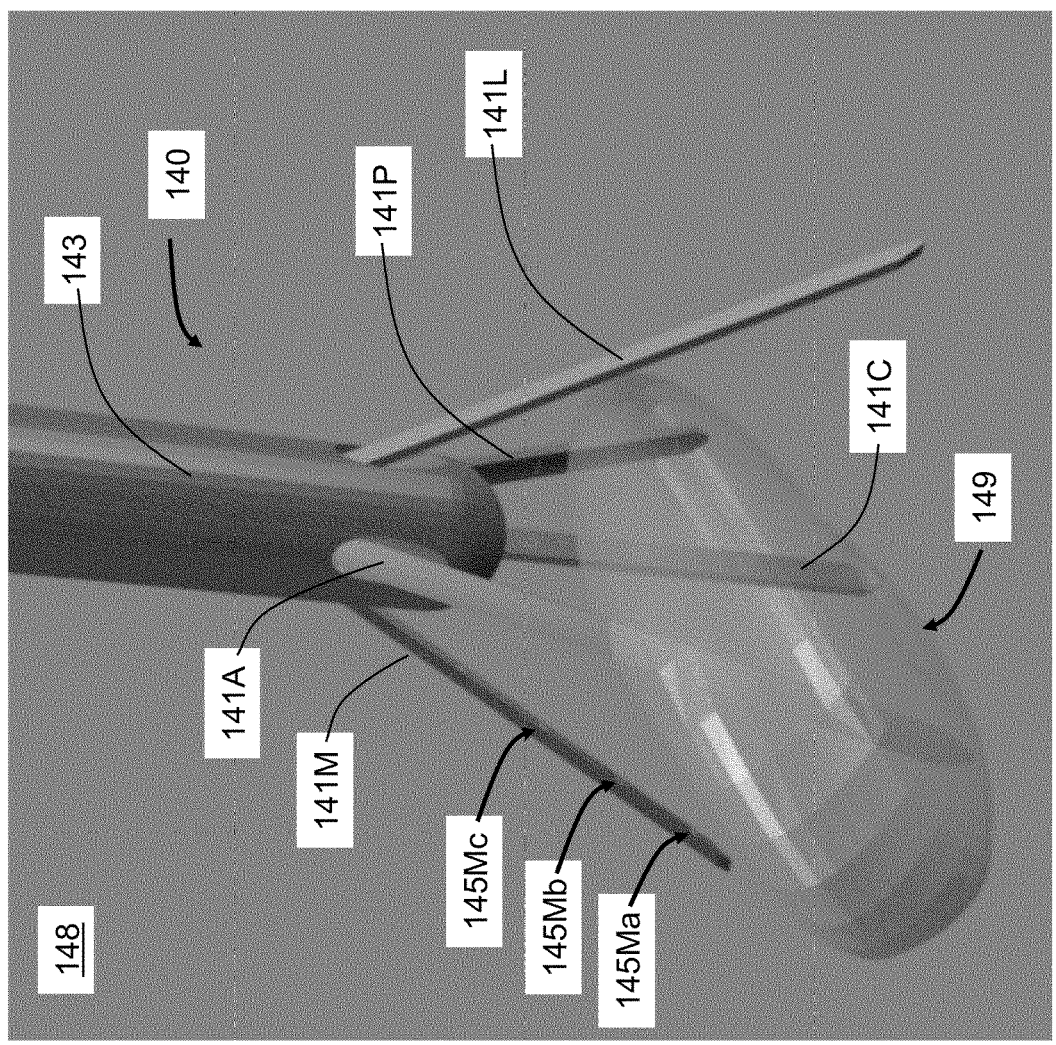
FIG. 3 is a perspective view of a portion of a human anatomy illustrating an exemplary microelectrode structure positioned at a neurological target.

Referring now to FIG. 3, a cross-sectional view of a portion of an anatomy 148 is shown, illustrating an exemplary microelectrode probe assembly 140 positioned at a neurological target 148 (e.g., subthalmic nucleus, shown). The microelectrode probe assembly 140 includes five microelectrode array shafts, 141A, 141P, 141L, 141M, 141C (generally 141) protruding from a cylindrical containment structure 143. On each microelectrode array shaft 141 are three microelectrode elements 145 distributed linearly along the microelectrode array shaft 141. Preferably, the microelectrode probe assembly 140, and its protruding microelectrode electrode arrays shafts 141 are shaped, spaced, and sized to allow one or more of the microelectrode elements 145 to be positioned at the neurological target 149.

As illustrated, one or more of the microelectrode elements 145 of the microelectrode probe assembly 140 are positioned in intimate contact with the neurological target 149. In more detail, each microelectrode element 145 is a disc electrode along a shaft. It is understood that some microelectrode array shafts 141 can be in contact with the neurological target, while other microelectrode array shafts 141 are not (as shown). Additionally, it is understood that some microelectrode elements 145 can be in contact with the neurological target, while other microelectrode elements 145 are not (as shown). In at least some embodiments, one or more of the microelectrode elements 145 are remotely accessible from a proximal end of the probe assembly 140 via one or more electrically conductive leads (not shown).

In at least some embodiments, selectable microelectrode elements 145 can be activated to record and or stimulate the target 149. For example, recordings of neurological activity from microelectrode elements 145 in contact with the target 149 can be used to identify the location of the target 149 relative to the probe assembly 140 or relative to a standard stereotactic reference coordinate. As determined form the recordings, only those microelectrode elements 145 in contact with the target may be activated to stimulate the target.

Any of the supporting structures described herein, such as the supporting structure 140 illustrated here can be a ridged, or semi rigid structure, such as a polymeric cylinder. Alternatively or in addition, the structure can be a flexible structure, such as one or more flexible substantially non conducting substrate (i.e., a bi-electric ribbon) onto which the microelectrode elements 145 are formed as electrically conductive film layers. The one or more microelectrode elements 145 are in communication with electronic circuitry (not shown) through one or more electrical leads (not shown) that can be routed through an internal lumen of a supporting structure 140 and/or formed using elongated film layers along a flexible, ribbon like supporting structure 140.

In some embodiments, the microelectrode elements 145 can be placed into the brain generally for recording and/or stimulation of the cortex and for deep brain stimulation and/or recording of neurological targets including the subthalamic nucleus and the pedunculopontine nucleus. The microelectrode elements 145 can also be placed in other parts of the body, such as the spine, the peripheral nervous system for neural recording and/or neural stimulation of such portions of an animal anatomy. Although microelectrodes are discussed generally throughout the various embodiments, there is no intention to limit the upper or lower size of the microelectrodes. The devices and methods described herein are generally scalable, with a microelectrode size determined according to the intended application. For at least some of the neurological applications, microelectrodes are dimensioned sub-millimeter. In some embodiments, the microelectrodes are formed as planar structures having a diameter of about 150 μm that are arranged in a linear array with center to center spacing of about 1000 μm. The planar structure of the microelectrodes can have regular shapes, such as circles, ellipses, polygons, irregular shapes, or a combination of such regular and/or irregular shapes.

This probe assembly 140 is implantable near a neurological target, such as a target brain structure, using common neurosurgical techniques such as stereotaxy or endoscopy. The device might be inserted without support or within a cannula which may have an inner dimension slightly larger than the outer dimension of the device. Alternatively, or in addition to, the device may have a rigid stylet running along its central axis with an outer diameter that is smaller than the inner diameter of an axial lumen in the device. When used, such a cannula, or a stylet, is generally retracted once the device is in position.

The operator can connect the probe assembly 140 to a recorder unit configured to identify certain regions of the neurological target (e.g., the brain) according to the electrical activity detected by the probe assembly 140. In some embodiments, the microelectrode elements 145 used to record from the neurological target 149 can be the same microelectrodes as those used to stimulate the target in applications in which both recording and stimulation are accomplished. Alternatively or in addition, the microelectrode elements 145 used to record from the neurological target 149 can be separate microelectrode elements 145 from those used to stimulate the target 149. In some embodiments, microelectrodes destined for recording (e.g., 145) may differ in one or more of size, shape, number, and arrangement from those microelectrodes destined for stimulation, e.g., using different microelectrodes.

The microelectrode elements 145 configured for stimulation can be connected to a stimulation source through one or more interconnecting leads. In some embodiment, at least a portion of the stimulation source can be extracorporeal. Alternatively or in addition, the stimulation source can be in vivo. Any implanted elements of the stimulation source are preferably fabricated and/or contained with a hermetically sealed, bio-compatible envelope. Such bio-compatible packaging of signal sources is well known, for example, in the area of artificial pacemakers. The stimulation source, when provided, may be a controllable signal generator producing a desired signal according to a prescribed input. For example, the signal generator may receive an input indicative of a desired output stimulation signal frequency. Such output stimulation signals can have a variety of wave forms, such as pulses, charged balanced pulses, sinusoidal, square wave, triangle wave, and combinations of such basic wave forms.

In some embodiments, the stimulation source includes a pulse generator for applying signals to the microelectrodes site. The signals from the pulse generator can be connected directly to the microelectrodes, or they can be preprocessed using electronics. In some embodiments, such preprocessing electronics are embedded within the implantable device. The preprocessing electronics can filter certain parts of an original signal, such as a cardiac pacemaker signal, in order to select preferred frequency components of the original signal that are at or near a peak resistance frequency of the microelectrodes. For embodiments in which there are more microelectrodes than signals, electronics can route the stimulation signals to preferred one or more of the microelectrodes.

Figure 4:
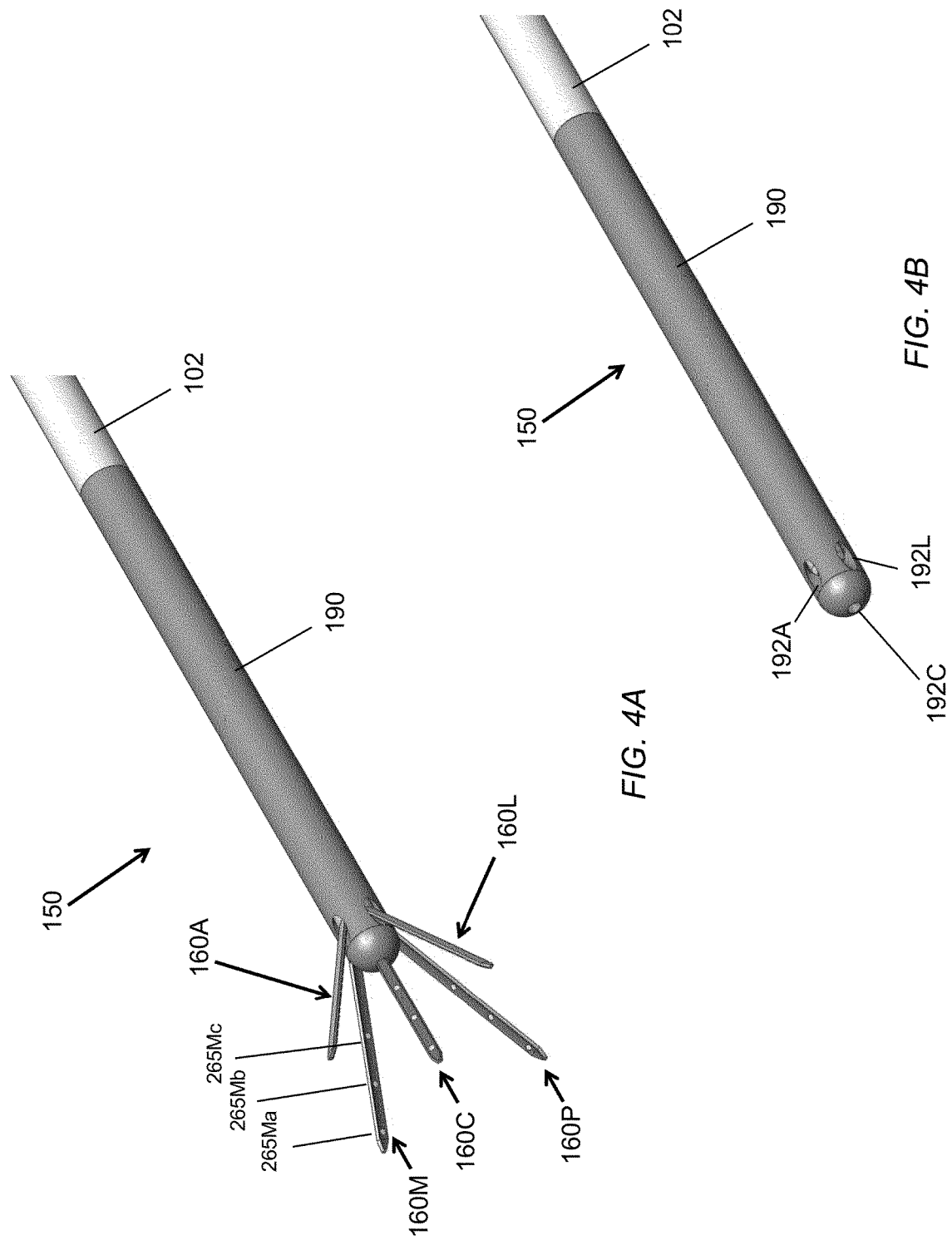
FIG. 4A is a perspective view of a distal portion of the elongated microelectrode assembly of FIG. 1 in the expanded position.
FIG. 4B is a perspective view of a distal portion of the elongated microelectrode assembly of FIG. 1 in the retracted position.

Referring now to FIG. 4A a more detailed view of a distal end of the microelectrode probe assembly 100 is shown. The microelectrode array assembly 150 includes a perforated end-cap 190 which contains the protruding microelectrode array shafts 160A, 160L, 160P, 160M, and 160C (generally 160). The microelectrode arrays shafts 160 are lettered A, L, P, M, and C in order to coincide with the anatomical convention of Anterior, Lateral, Posterior, Medial, and Central positions respectively. Each microelectrode array shaft 160 contains three microelectrode elements 265 in a linear arrangement. The microelectrode elements 265 on microelectrode array shaft 160M are shown and labeled 265Ma, 265Mb, and 265Mc. Microelectrode element 265Ma is the most distal along microelectrode array shaft 160M, whereas microelectrode element 265Mc is the most proximal. Each microelectrode array shaft 160 contains three microelectrode elements 265 on its interior surface.

Referring now to FIG. 4B a more detailed view of a distal end of the microelectrode probe assembly 100 in the retracted position is shown. In this state, the protruding microelectrode shafts 160 have been retracted into the interior of the perforated end-cap 190 and are completely contained within the microelectrode array assembly 150. Also visible are the perforations 192 on the perforated end-cap 190 which correspond to each microelectrode array shaft 160. The perforations 192 are lettered A, L, P, M, and C in order to coincide with the anatomical convention of Anterior, Lateral, Posterior, Medial, and Central positions respectively. The perforated end-cap 190 is attached to the outer cylindrical member 102.

Figure 5:
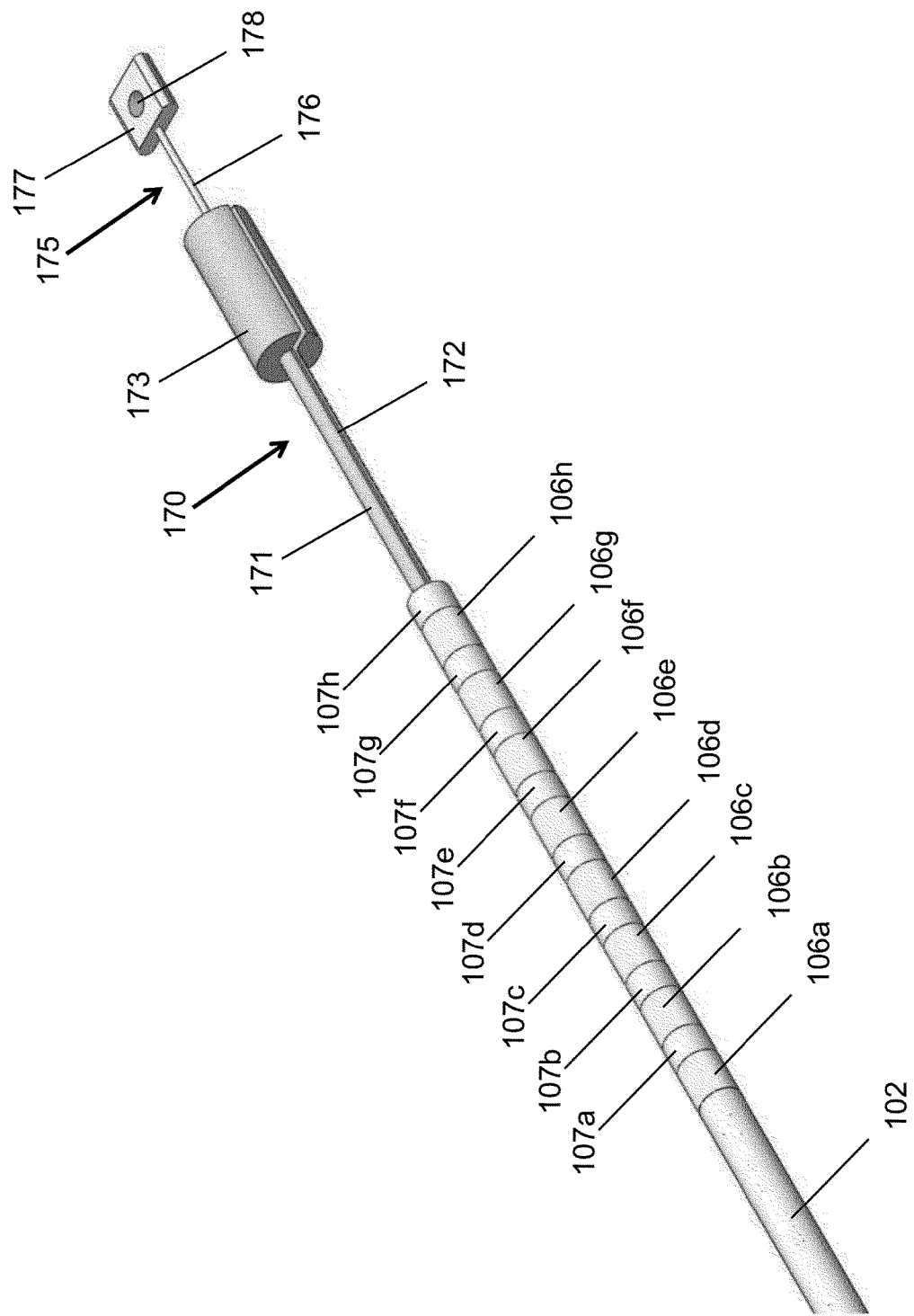
FIG. 5 is a perspective view of a proximal portion of the elongated microelectrode assembly of FIG. 1.

Referring now to FIG. 5 a more detailed view of the proximal end of the microelectrode probe assembly is shown. The cylindrical contacts 106 are arranged along the longitudinal axis of the outer cylindrical member 102. Each of the eight cylindrical contacts 106, 106a through 106h, is electrically connected to a lead wire (not shown) which is in communication with the distal end of the microelectrode lead assembly 100. In the exemplary embodiment each cylindrical contact measures 1.27 mm in diameter, and 2 mm in length. The cylindrical contacts 106 are spaced from each other by insulating cylindrical contacts 107a through 107h (generally 107). In some embodiments there may only be one cylindrical contact 106, while in other embodiments there may be two or more cylindrical contacts 106. Generally there are between four and eight cylindrical contacts 106.

The microelectrode lead assembly 100 contains one removable rigid push rod 170, and one non-removable flexible pull wire 175. The rigid push rod 170 is used to expand the microelectrode array assembly 150 into its expanded state. The flexible pull wire 175 is used to pull the microelectrode array assembly 150 back into is retracted state. As shown, the rigid push rod 170 is composed of three features. The first feature is a hollow rigid stylet 172 that is also used to straighten the microelectrode lead assembly 100 during implantation. The second feature is a longitudinal slit 173 which permits access to the central lumen of the rigid stylet 172. The third feature is the push handle 174 which permits the operator to apply a pressure and expand the microelectrode array assembly 150 at the distal end. As shown, the flexible pull wire 175 has three features. The first feature is a flexible central wire 176 which is permanently attached to the microelectrode array assembly 150 at the distal end. The second feature is a pull handle 178 which the operator can use to retract the microelectrode array assembly at the distal end by pulling. The third feature is a hole 179 in the pull handle 178 which the operator can use to facilitate the pulling action required of the component. Together, push rod 170 and pull rod 175 are used in order to expand and retract the microelectrode array shafts 160 and the distal end of the microelectrode lead assembly 100.

Figure 6:
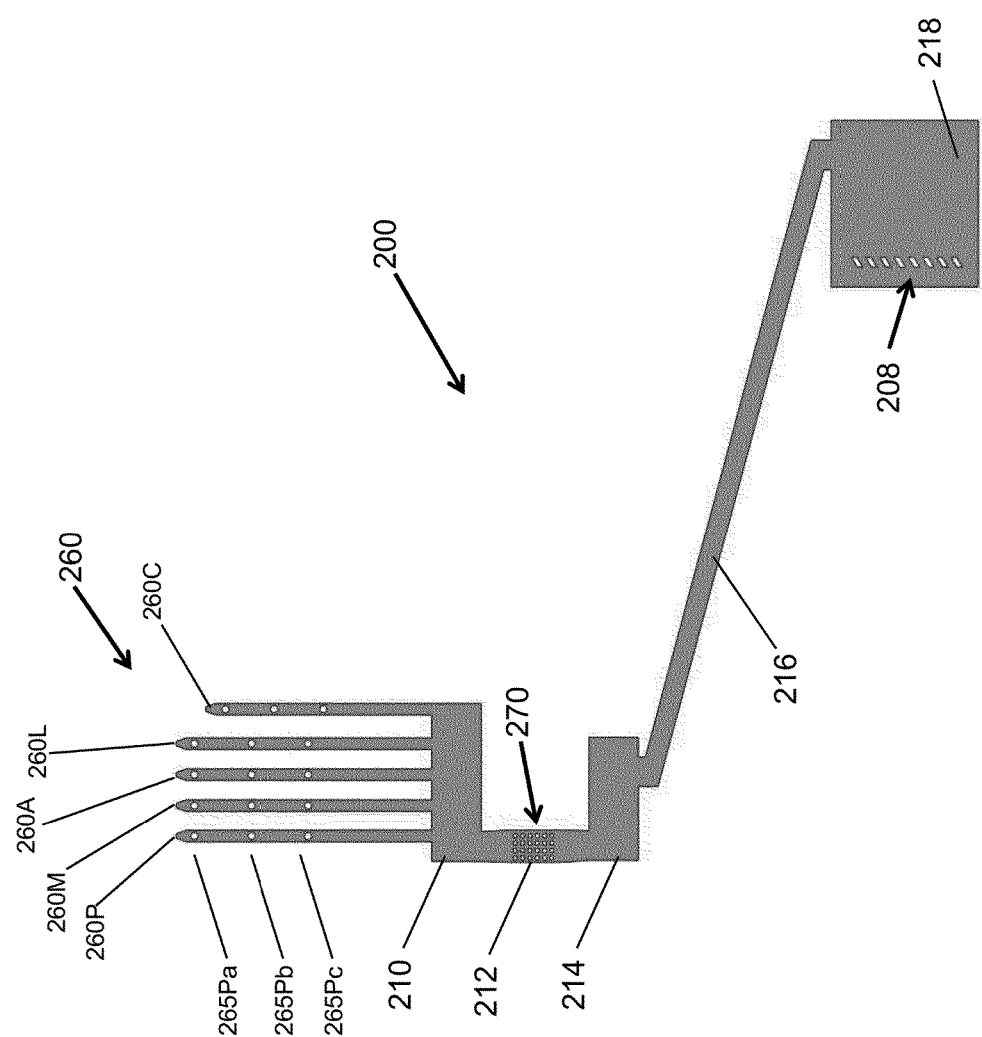
FIG. 6 is a planar view of an embodiment of a microelectrode array film.

Referring now to FIG. 6 a more detailed view of the microelectrode array film 200 is shown in its non-assembled state. The microelectrode array film 200 is produced using a sequential production method where several films are deposited one atop the other. The first film is a polymeric, isolating film such as polyimide. The second film is a conductive, preferably noble metallic film such as platinum. The second film is structured in order to create metallic traces and discs. The third film is a polymeric, isolating film, such as polyimide. The third and first films are then structured to provide the outline shown in FIG. 6. Embedded metallic layers are not shown, while metallic discs and electrical contacts are exposed. The microelectrode film shafts 260 correspond each to one of the microelectrode array assembly shafts 160 shown previously. The microelectrode film shafts 260 are numbered corresponding to their appropriate shaft, Anterior, Lateral, Posterior, Medial, and Central as 260A, 260L, 260P, 260M, and 260C. The microelectrode film shafts 260 contain the microelectrode elements 265. The microelectrode elements 265 on microelectrode film shaft 260P are labeled as an example, where 265Pa is the most distal microelectrode element and 265Pc is the most proximal microelectrode element. The length of microelectrode film shaft 260C and the spacing of its microelectrode elements 265 differs slightly from the other geometries because it forms part of the central microelectrode array shaft 160 and will not be at an angle to the longitudinal axis of the microelectrode lead assembly 100.

The next feature on the microelectrode array film 200 is the distal structural cylinder 210 which is shown in its flattened state, but once assembled will be used to stabilize the film in its final assembly. The microelectronic platform 212 is where a subsequent microelectronic component will be attached. The microelectronic component is explained in detail below. It is preferably attached to the microelectrode array film 200 while it is still in its flattened state. On the microelectronic platform 212 are arranged the microelectronic platform bond bands 270 which are used to electrically communicate the microelectrode elements 265 to external equipment through the microelectronic component. They are arranged in a two dimensional array. The central structural cylinder 214 which is shown in its flattened state, but once assembled will be used to stabilize the film in its final assembly. The helical ribbon cable 216 which is shown in its flattened state, but once assembly will be used to permit movement of the microelectrode array assembly 150 within the microelectrode lead assembly 100. The proximal structural cylinder 218 is shown in its flattened state, but will be attached to an internal cylinder within the microelectrode lead assembly 100 and is the only non-moving part of the microelectrode array film 200. On the proximal structural cylinder 218 are the proximal contact pads 208 which are used to communicate the elements of the microelectronic component to lead wires that communicate the distal portion of the microelectronic lead assembly 100 to its proximal portion.

Figure 7:
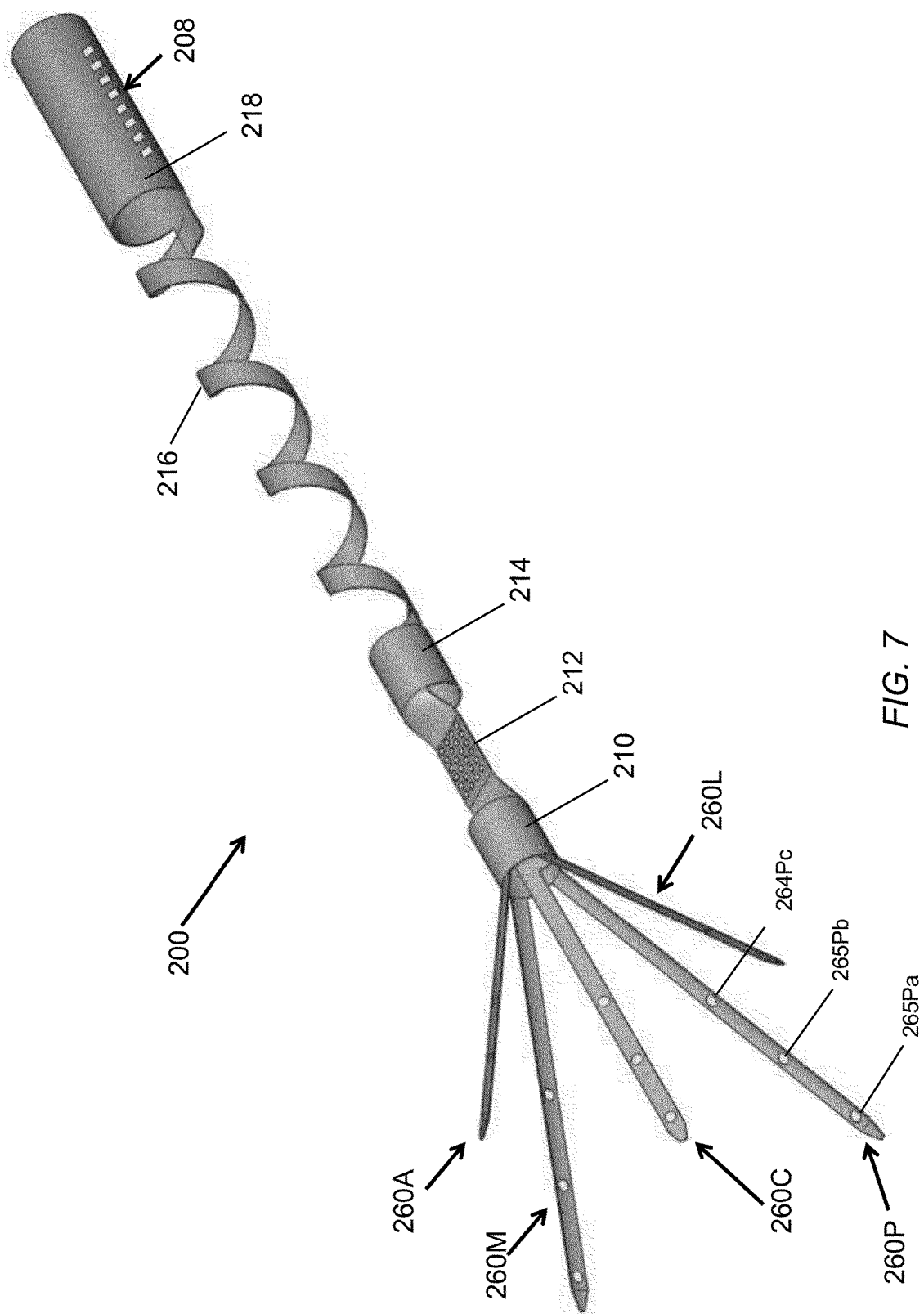
FIG. 7 is a perspective view of the embodiment of a microelectrode array film of FIG. 6 after it has been assembled.

FIG. 7 demonstrates the microelectrode array film 200 in its assembled, and expanded state. The central microelectrode film shaft 260C, and the four microelectrode film shafts 260A, 260L, 260P, 260M are shown, with their respective microelectrode elements 265 on the interior of the assembly. The distal structural cylinder 210 is shown curled into its cylindrical state. The microelectronic platform 212 is shown bent it its horizontal position. The central structural cylinder 214 is shown curled into its cylindrical state. The helical ribbon cable 216 is shown curled and pulled into its assembled state. The proximal structural cylinder 218 is shown curled into its position, with proximal contact pads 208 exposed. The microelectrode array film 200 can be assembled into this configuration in steps, or after assembly with subsequent components.

FIG. 8A is a planar side view of the microelectrode array film 200 in its assembled, and expanded state. The important features to note in this view are the slits 211, 215, 219 in the structural cylinders 210, 214 and 216 respectively which are present because of the curling required to assemble the film into its position.

FIG. 8B is a planar top view of the microelectrode array film 200 in its assembled, and expanded state.

Figure 9:
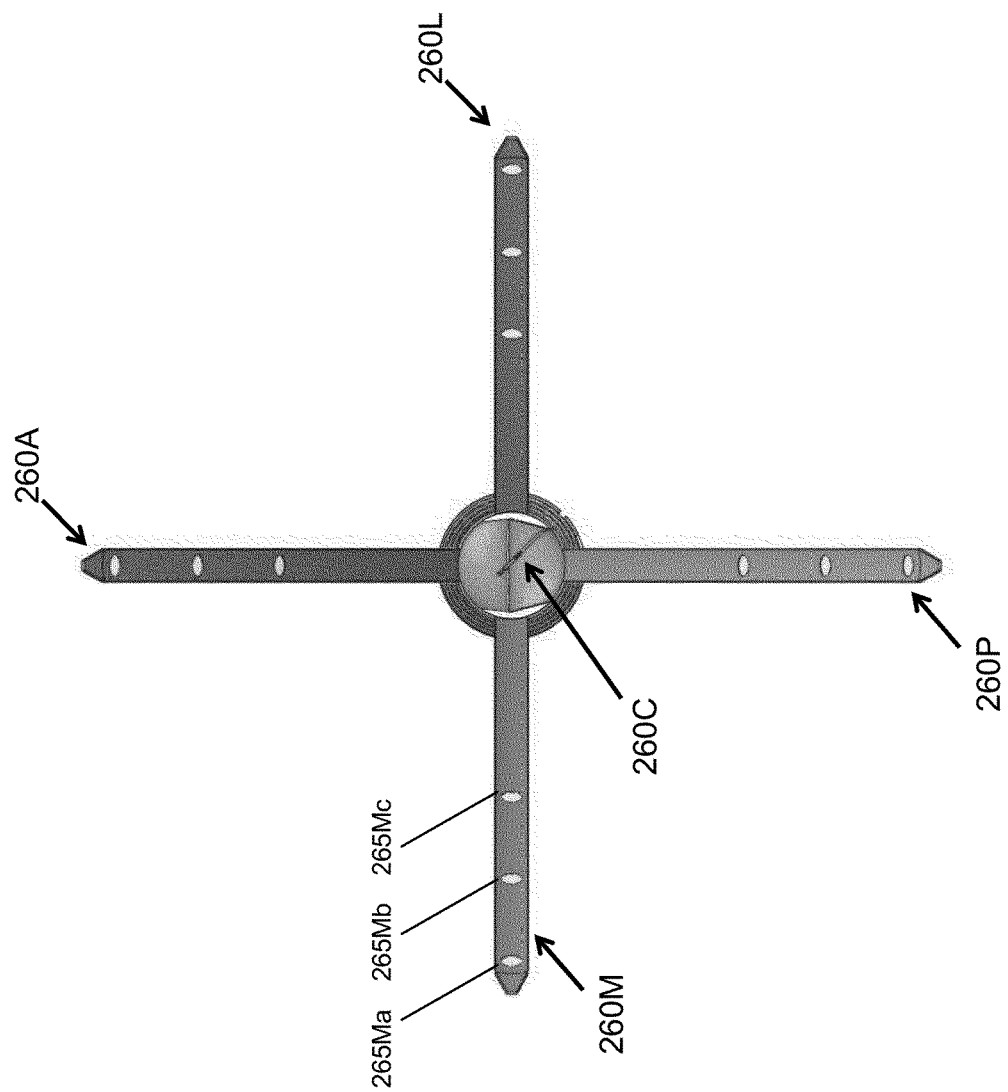
FIG. 9 is a planar frontal view of the microelectrode array film assembly of FIG. 7.

FIG. 9 is a planar front view of the microelectrode array film 200 in its assembled, and expanded state. The position of the four angled microelectrode film shafts 260 are shown, and the interior microelectrode elements 265 are visible.

Figure 10:
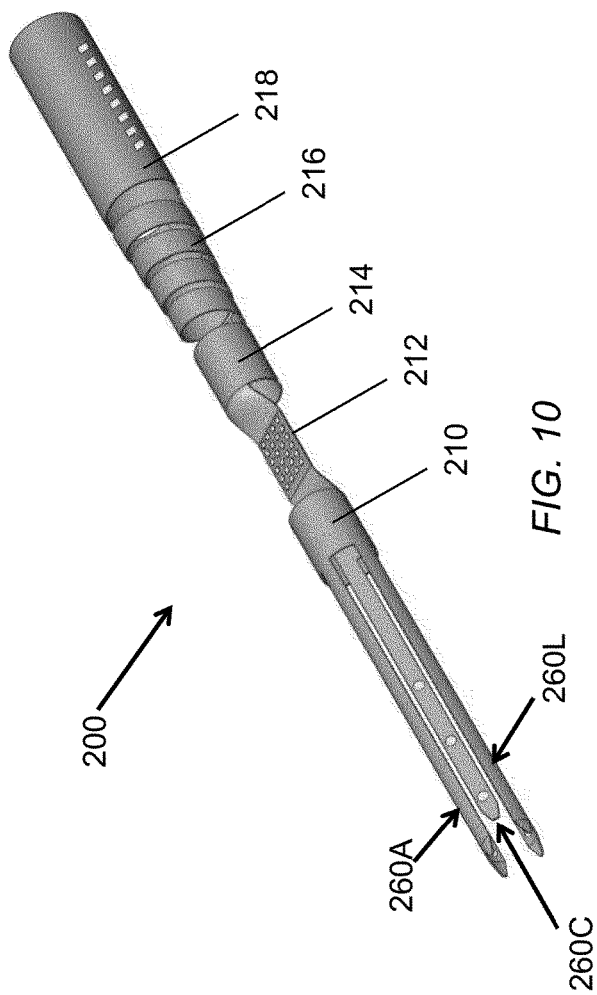
FIG. 10 is a perspective view of the microelectrode array film assembly of FIG. 7 in the retracted position.

FIG. 10 demonstrates the microelectrode array film 200 in its assembled, and retracted state. The central microelectrode film shaft 260C, and the four microelectrode film shafts 260A, 260L, 260P, 260M are shown, with their respective microelectrode elements 265 on the interior of the assembly. These microelectrode film shafts 260 have moved from their angle position into a closed position. The structural cylinders 210, 214 and 218 have not change in shape. Structural cylinders 210 and 214 have not moved in position relative to each other. Structural cylinders 210 and 214 have both moved closer to structural cylinder 218. This movement has caused the reversible of the helical ribbon cable 216.

Figure 11:
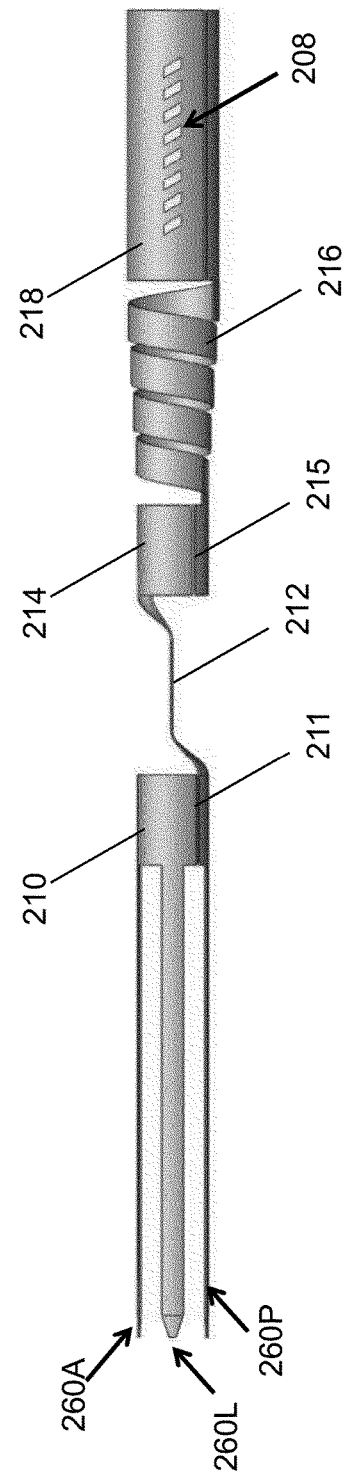
FIG. 11 is a planer view of the retracted microelectrode array film assembly of FIG. 10.

FIG. 11 demonstrates a planar side view of the microelectrode array film 200 in its assembled, and retracted state. The anterior microelectrode film shaft 260A and the posterior microelectrode film shaft 260P are in parallel positions.

Referring now to FIG. 12A, a perspective view of the central pin 185 is shown. This pin will be assembled in a subsequent step to the microelectrode array film 200. The central pin has several features including a protruding axial shaft 186, a cylindrical member 188, and a lengthwise slit 189 on the cylindrical member 188. The protruding axial shaft 186 has a bend 187 which permits it to be positioned along the longitudinal axis of the cylindrical member 188. Generally, the component is formed from a rigid cylindrical material such as medical grade stainless steel which has been cut by a laser into the present shape. FIG. 12B demonstrates a side view of the central pin 185.

Referring now to FIG. 13A, a perspective view of the expandable shaft support 180 is shown. The expandable shaft support 180 is composed of cylindrical member 182, from which protrude four semi-rigid shafts into the Anterior direction 181A, the Lateral direction 181L, the Posterior direction 181P, and the Medial direction 181M. The semi-rigid shafts 181 are expanded radially from the longitudinal axis of the cylindrical member 182. Generally, the component is formed from a rigid cylindrical material such as medical grade stainless steel which has been cut by a laser into the present shape. FIG. 13B demonstrates a perspective view of the expandable shaft support 180 in its retracted position.

Referring now to FIG. 14, the central pin 185 is shown assembled onto the central microelectrode film shaft 260C to form the central microelectrode array shaft 160C.

Referring now to FIG. 15, the microelectronic component 300 has been assembled onto the microelectronic component platform 212. Contact pads on the microelectronic component 300 have been attached to their respective microelectronic contact pads 270 on the microelectrode array film. The proximal structural cylinder 218 has been attached and wrapped around the internal elongated cylindrical member 103 which extends to the proximal portion of the microelectrode lead assembly 100. The distal portion of the central pull wire 175 is visible. It is permanently attached to the interior of the central support cylinder 214 and is used to pull the assembly into its retracted position.

Referring now to FIG. 16, microelectrode array film 200 has been assembled onto the interior circumference of the expandable shaft support 180 forming the microelectrode array shafts 160. In addition, the helical lead wires 290 have been wound around the internal cylindrical member 103 and have been attached to their respective proximal contact pads 208.

Referring now to FIG. 17, the microelectrode array shafts 160 are shown with the stiff push rod 170 in contact. The stiff push rod 170 is used to push the assembly into its expanded position. Additionally, the assembly is shown with outer cylindrical member 102 in its assembled position.

Figure 18:
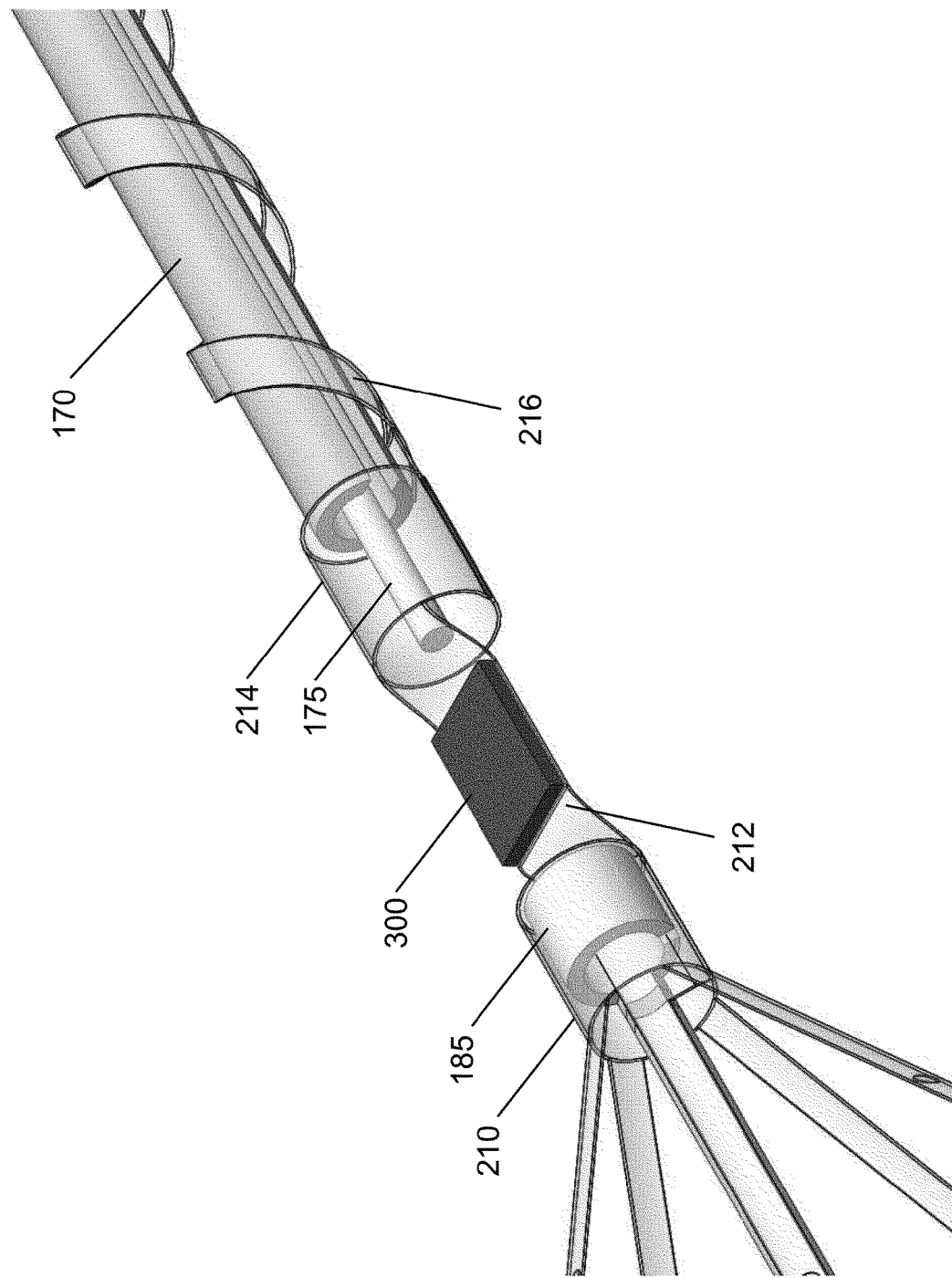
FIG. 18 is a close-up perspective view of the microelectrode assembly of FIG. 17 showing the flexible pull wire and the stiff push rod in more detail.

FIG. 18 is a close-up perspective view of the interior assembly to demonstrate the positions of the stiff push rod 175 and the flexible pull wire 170.

Figures 19A, 19B:
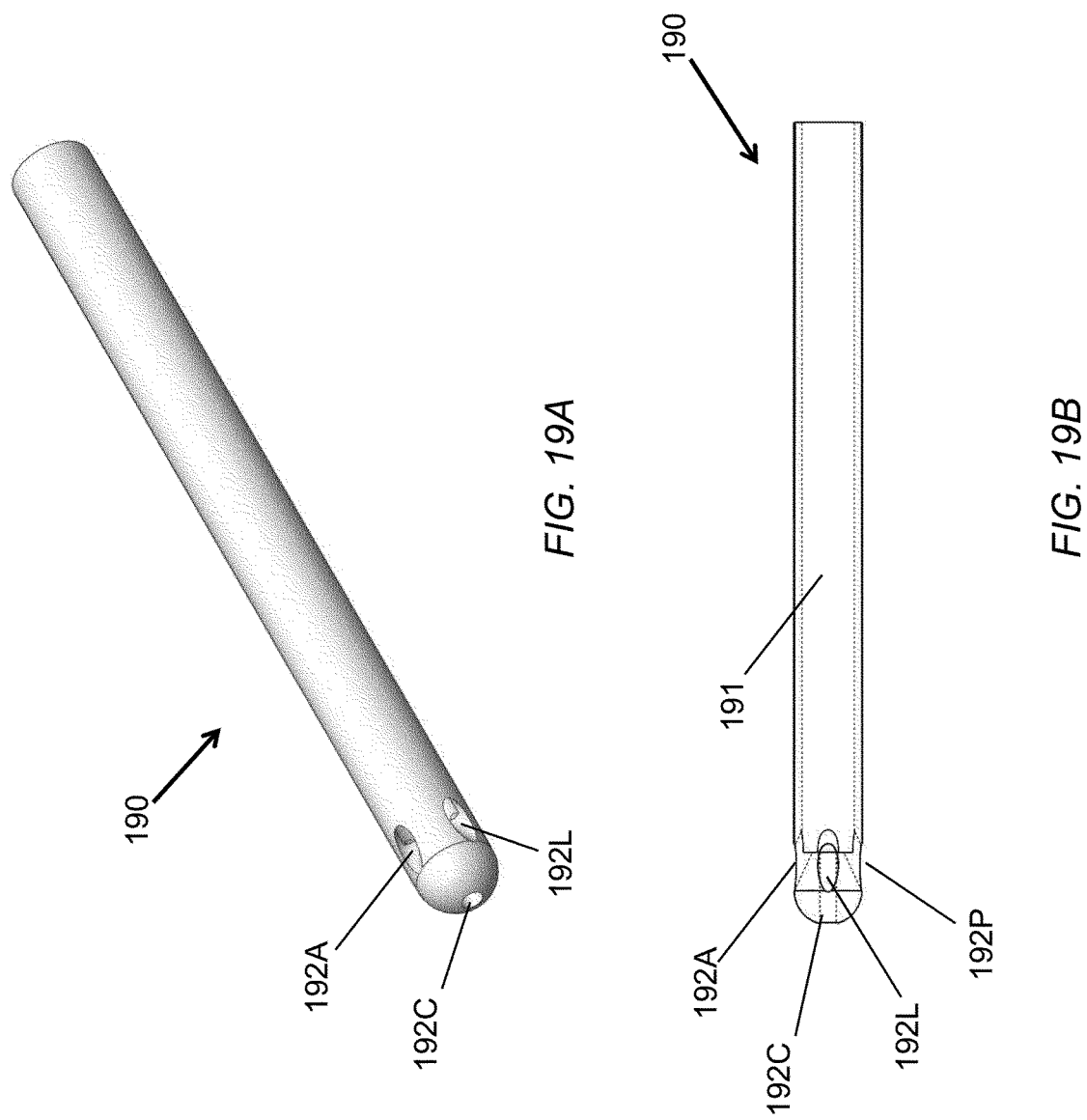
FIG. 19A is a perspective view of the perforated end cap.
FIG. 19B is a planar view of the perforated end cap.

FIG. 19A is a perspective view of the perforated end-cap 190 which demonstrates the perforations 192 from which the microelectrode shafts will emerge. FIG. 19B is a planar cutaway view demonstrating the cavity 191 within the perforated end-cap 190 in which the entire microelectrode array shaft assembly 160 is housed.

FIG. 20 is a cut-away perspective view with several elements removed for clarity of the assembly in the expanded position. Part of the perforated end cap 190 and the expandable shaft support 180 have been removed in order to reveal the positions of the microelectrode component 300, and the stiff push rod 170.

Figure 21:
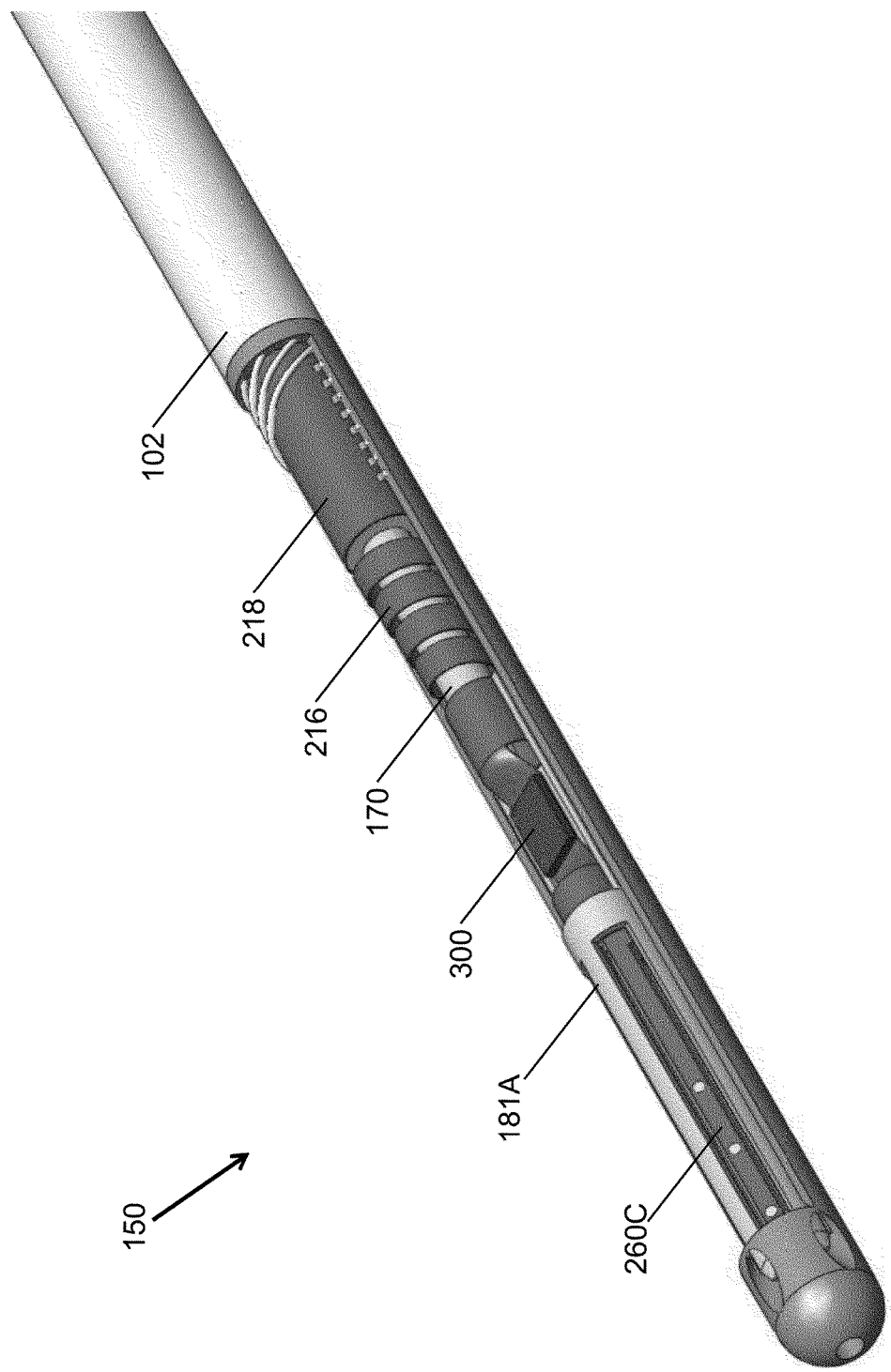
FIG. 21 is a cut-away perspective view of the retracted microelectrode assembly of FIG. 4B with segments of the perforated end cap and outer legs component removed.

FIG. 21 is a cut-away perspective view with several elements removed for clarity of the assembly in the retracted position. Part of the perforated end cap 190 and the expandable shaft support 180 have been removed in order to reveal the positions of the microelectrode component 300, and the stiff push rod 170. Most importantly, the microelectrode array shafts 260 are contained within the interior of the perforated end cap 190, and the helical ribbon cable 216 has been reversible compressed into is retracted position.

Figure 23:
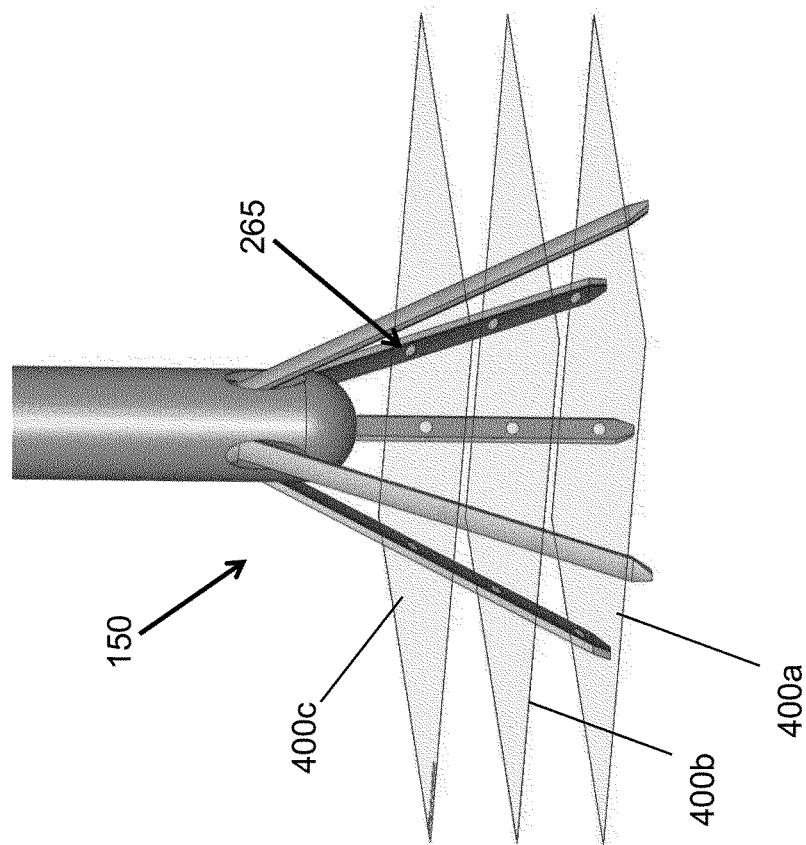
FIG. 23 is a perspective view the assembly and planes of FIG. 22.
Figure 22:
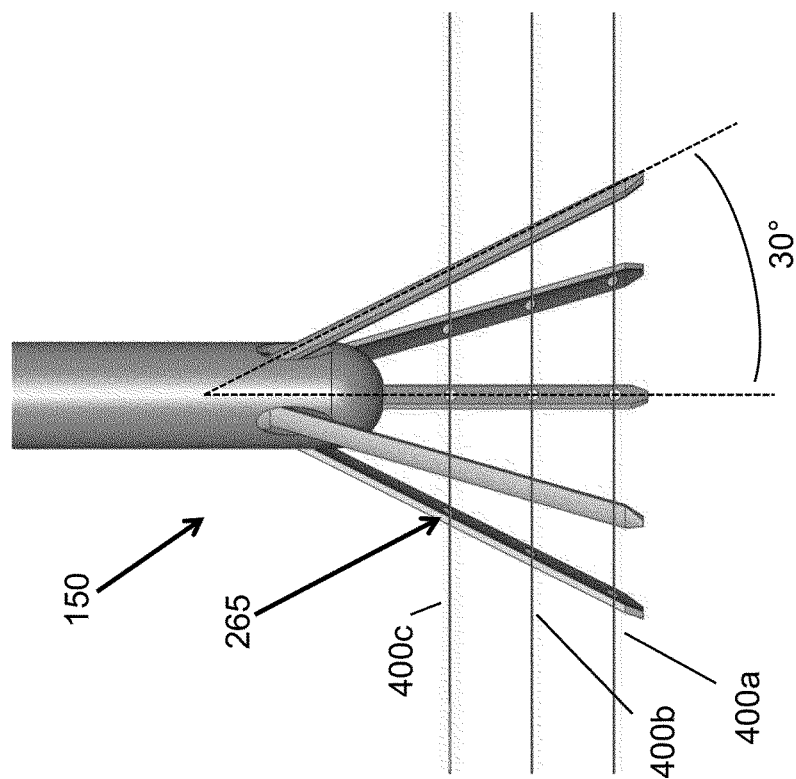
FIG. 22 is a planar view of the microelectrode assembly demonstrating microelectrode elements on the same plane.

When the microelectrodes are in use, they are placed on the same plane, in order to improve the operator's understanding of anatomical placement of the electrophysiological recording, and or stimulation. FIG. 22 is a planar view of the microelectrode assembly demonstrating microelectrode elements on the same plane. FIG. 23 is a perspective view the same assembly and same planes of FIG. 22. In this embodiment, the planes are separated by 1 mm, and are parallel. This arrangement requires that the microelectrode elements 265 on the central protruding shaft 160C have a smaller spacing than the microelectrode elements 265 on the anterior, lateral, posterior, medial protruding shafts 160A, 160L, 160P, 160M. In the present embodiment, it has been chosen that the protruding shafts make a 30° angle with the central shafts once expanded. In the expanded position, the most distal microelectrode elements 265 of the five protruding shafts 160 should all be on the same plane 400a. Additionally, the central microelectrode elements 265 of the five protruding shafts 160 should all be on the same plane 400b. Furthermore, the most proximal microelectrode elements 265 of the five protruding shafts 160 should all be on the same plane 400c.

Additional Embodiments

Figures 24, 25, 26:
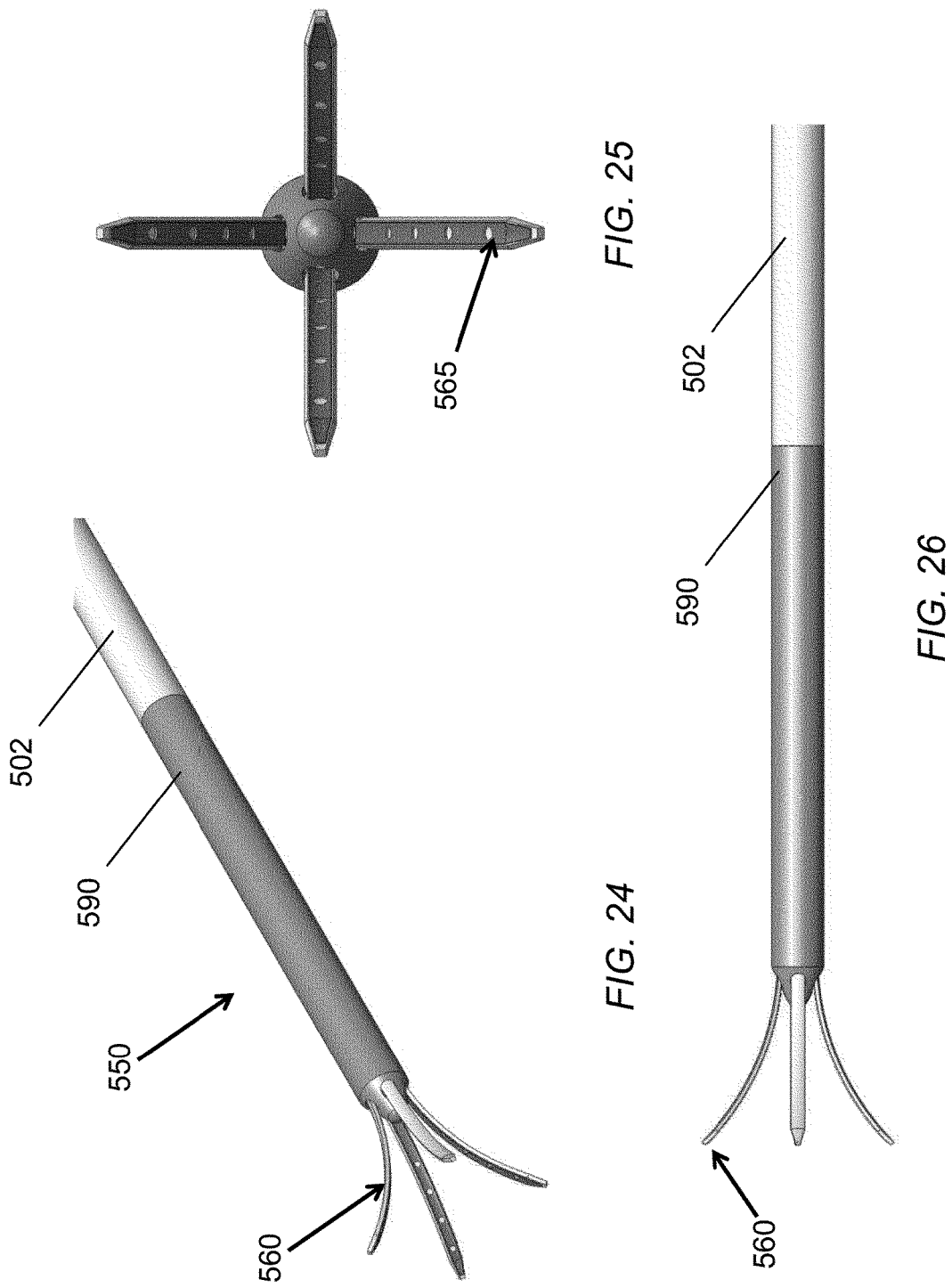
FIG. 24 is a perspective view of an alternative embodiment of the elongated microelectrode assembly of FIG. 1.
FIG. 25 is a planar front view of the alternative embodiment of FIG. 24.
FIG. 26 is a planar side view of the alternative embodiment of FIG. 24.

In some embodiments the protruding shafts may be curved, or bent, into a different angle. This may have the advantage that the tips of the protruding shafts can cover a greater volume. FIG. 24 demonstrates an embodiment of a distal microelectrode assembly 550 where the protruding shafts 560 curl away from the longitudinal axis of the elongated probe. On each of the protruding shafts are four microelectrode elements. In some embodiments the central pin may not be necessary, and the embodiment in FIG. 24 does not contain said central pin. FIG. 25 is a planar view of the same embodiment, and FIG. 26 demonstrates an additional view.

In some embodiments it is advantageous for the protruding shafts to be bent in such a manner that when in the expanded state, they remain parallel to the longitudinal axis of the elongated probe. The alternative embodiment of a distal microelectrode assembly 650 shown in FIG. 27 demonstrates protruding shafts 660 that have been bent in order to remain parallel to the longitudinal axis of the said assembly. This creates a cylindrical volume of influence within the confines of the device. Additionally, the central protruding shaft 660C may consist of a single cylindrical electrode, and not an array of microelectrodes. FIG. 28 demonstrates this alternative embodiment in a planar side view.

Figure 31:
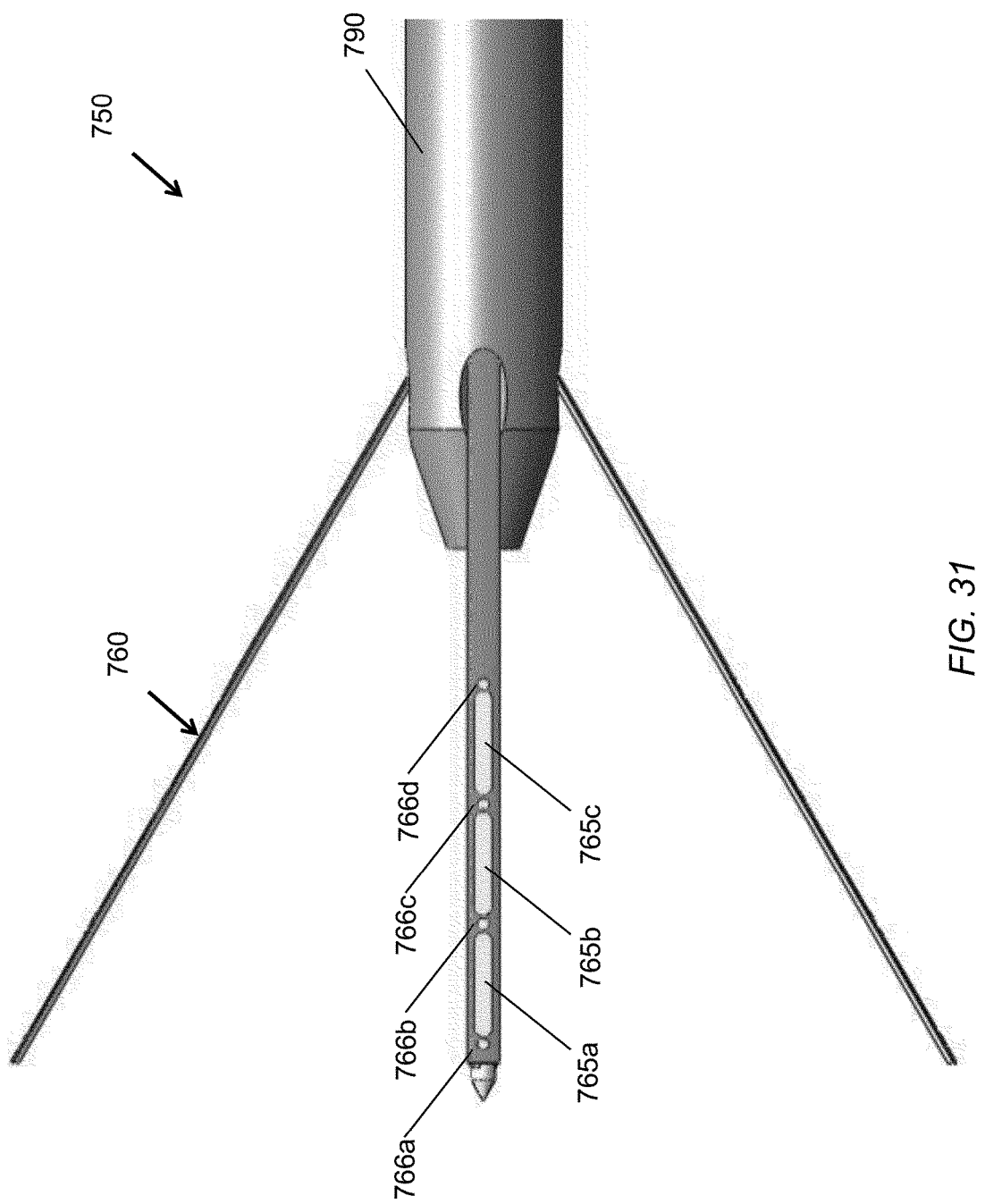
FIG. 31 is a planar side view of the alternative embodiment of FIG. 29 depicting separate stimulation and recording electrodes.

In some embodiments it is advantageous for the microelectrode array film to be positioned on the exterior of the protruding shafts. FIG. 29 is a perspective view of an alternative embodiment of a distal microelectrode assembly 750 where the microelectrode elements are placed on the outside of the protruding shafts. FIG. 30 demonstrates a planar back view of the alternative embodiment. FIG. 31 is a planar side view of the alternative embodiment of FIG. 29 depicting separate stimulation and recording electrodes. In some embodiments it is advantageous for recording microelectrode elements 766 to be smaller in diameter than the stimulation microelectrode elements 765. Additionally, stimulation microelectrode elements 765 may function advantageously with larger effective surface areas.

FIG. 32 is a detail perspective view of the alternative embodiment of FIG. 29 with perforated end-cap removed. Due to the friction that repeated retraction and expansion of the protruding shafts may create on the microelectrode array film, a slide guide 781 is introduced in this embodiment. Additionally, as shown in FIG. 33, the central pin 781 is implemented as a sharpened cylinder, on which a large microelectrode element 767 has been wrapped. Additionally, a central pin support 782 is introduced which permits alignment and added robustness of the central protruding shaft 760C.

Figure 35:
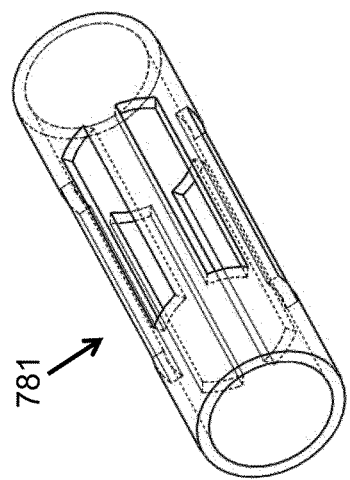
FIG. 35 is an additional component of the alternative embodiment of FIG. 29.
Figure 36:
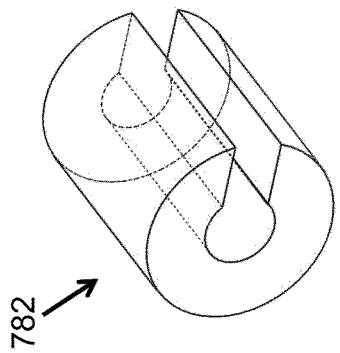
FIG. 36 is yet an additional component of the alternative embodiment of FIG. 29.
Figure 34:
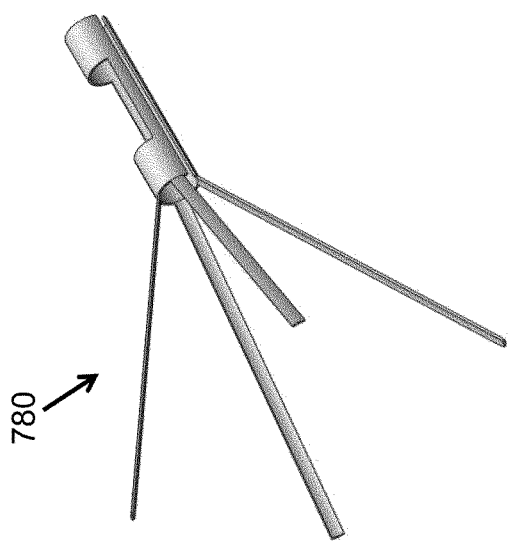
FIG. 34 is a component of the alternative embodiment of FIG. 29.

FIG. 34 demonstrates the required protruding shaft support 780 required to implement the alternative embodiment. FIG. 35 demonstrates the slide guide 781, and FIG. 36 depicts the central pin support 782.

Figure 37:
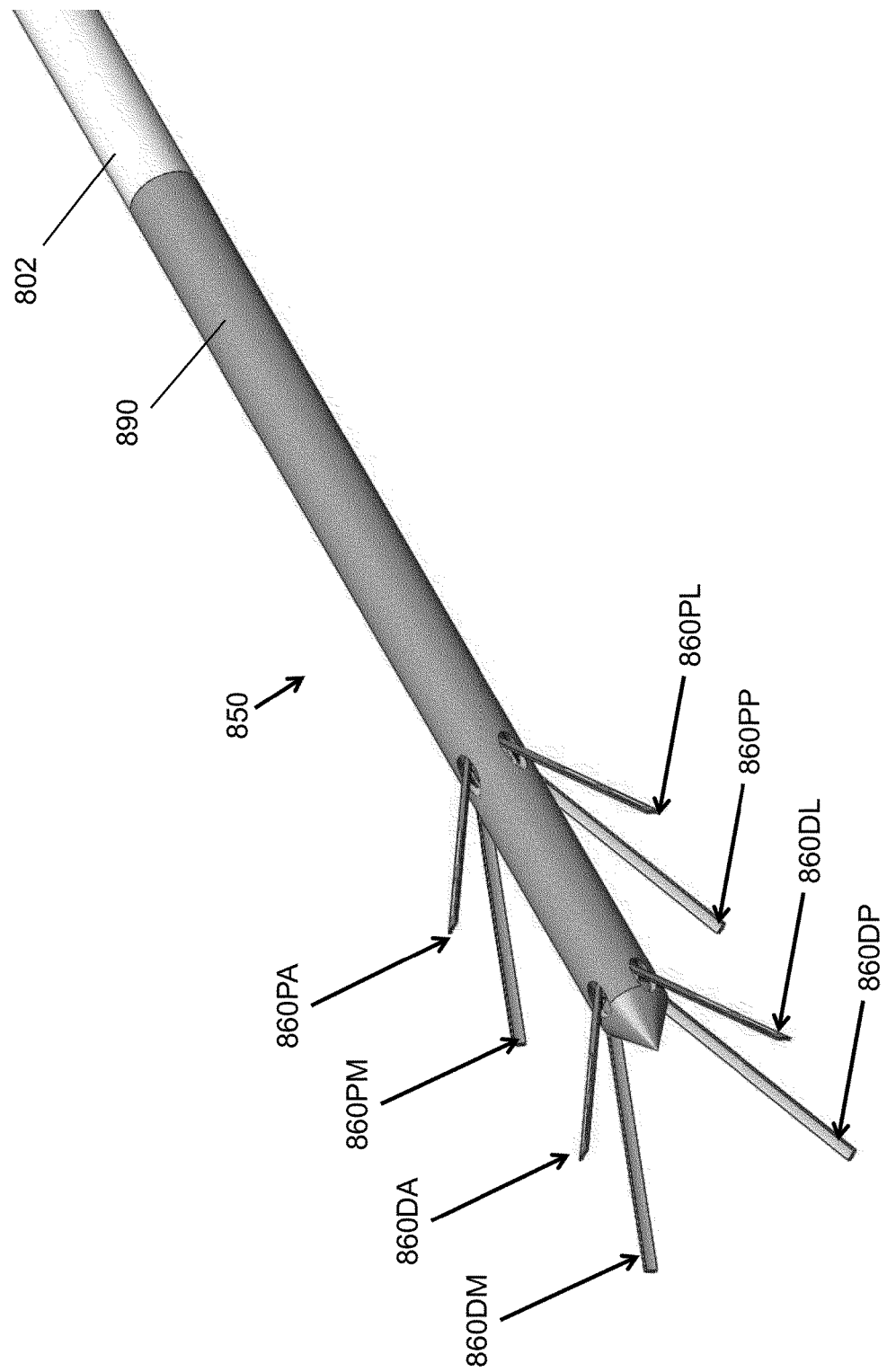
FIG. 37 is a perspective view of an alternative embodiment of FIG. 1 where the protruding shafts have been implemented at two different regions of the longitudinal axis.

In some embodiments it is advantageous to include protruding shafts and different distal distances along the longitudinal axis of the elongated microelectrode probe. FIG. 37 is a perspective view of an alternative embodiment where eight protruding shafts have been implemented at two different distal regions of the longitudinal axis. The components required to implement this embodiment are similar to the previous embodiments presented. Distal microelectrode assembly 850 is composed of an elongated perforated end cap 890 which contains the microelectrode array film 820 and protruding shaft support structure 880. The protruding shafts (generally 860) have been numbered according to their proximal or distal position, as 860P or 860D in general. The protruding shafts have been additionally numbered according to their anatomical position, anterior, lateral, posterior, and medial. For example, the proximal protruding shafts (generally 860P) have been numbered 860PA, 860PL, 860PP, and 860PM.

Figure 38B:
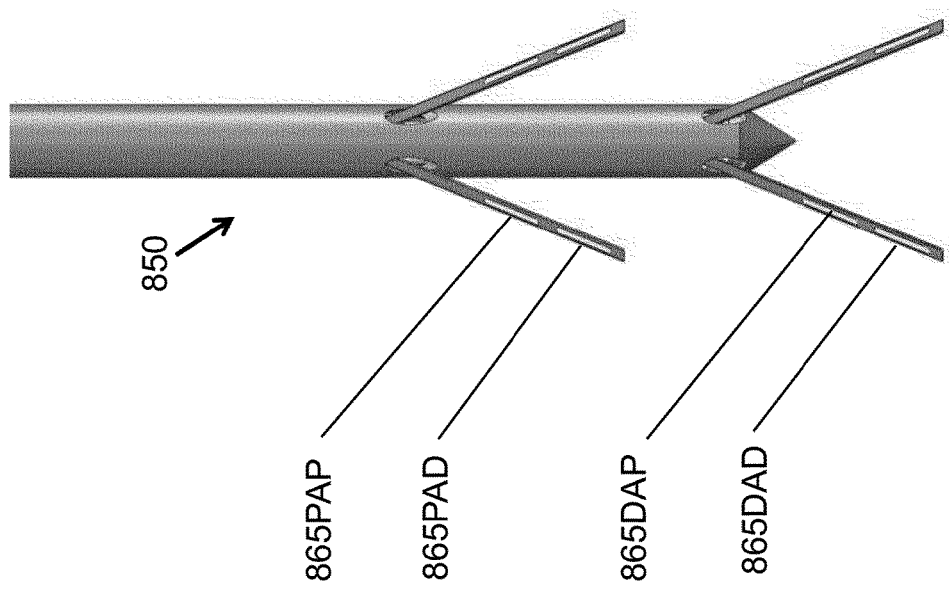
FIG. 38B is an additional planar view of the alternative embodiment of FIG. 37.
Figure 38A:
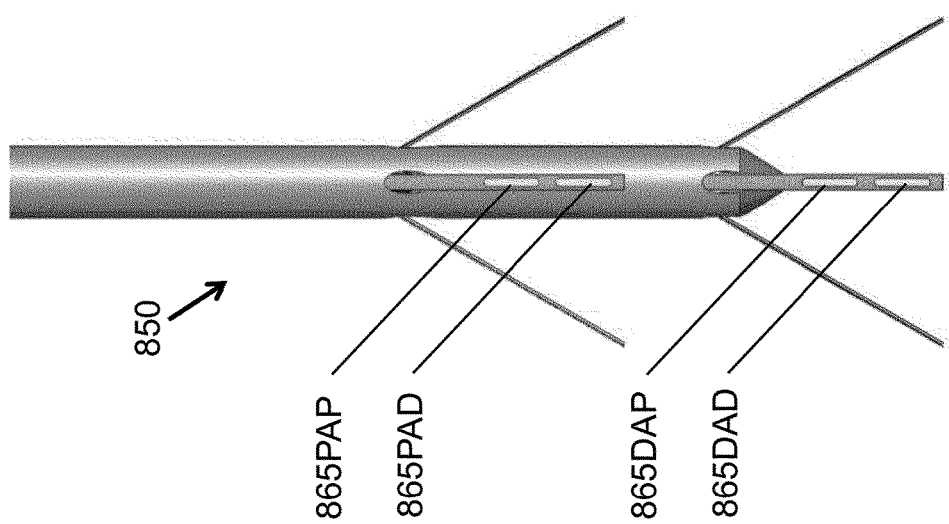
FIG. 38A is a planar view of the alternative embodiment of FIG. 37.

FIG. 38A is a planar view of the alternative embodiment of FIG. 37 which demonstrates the microelectrode elements (generally 865) in more detail. The microelectrode elements 865 in this embodiment are confined to two elongated elliptical shapes per protruding shaft 860 and are dedicated to neural stimulation. However, it is understood, as with previous embodiments, that the geometry, size, and quantity of microelectrode elements can vary. Additionally, as with previous embodiments, the intended use of the microelectrodes can vary, such as microelectrode elements 860 that are designed specifically for neural recording. FIG. 38B is an additional planar view of the same embodiment.

FIG. 39A is a perspective view of the microelectrode array film 820 required in the assembly of the alternative embodiment of FIG. 37. In this embodiment an extended portion 828 is used to add additional microelectrode array shafts 861 to the designs of previous embodiments. It is understood to those knowledgeable in the art that the same microfabrication and assembly methods are used to implement this alternative embodiment.

FIG. 39B is a perspective view of the protruding shaft support 880 required in the assembly of the alternative embodiment of FIG. 37. As with previous embodiments, this shaft support 880 can be cut from a hollow cylinder of material using a laser etch process. The microelectrode array film 820 is then assembled onto the surface of protruding shaft support 880.

Figures 40A, 40B:
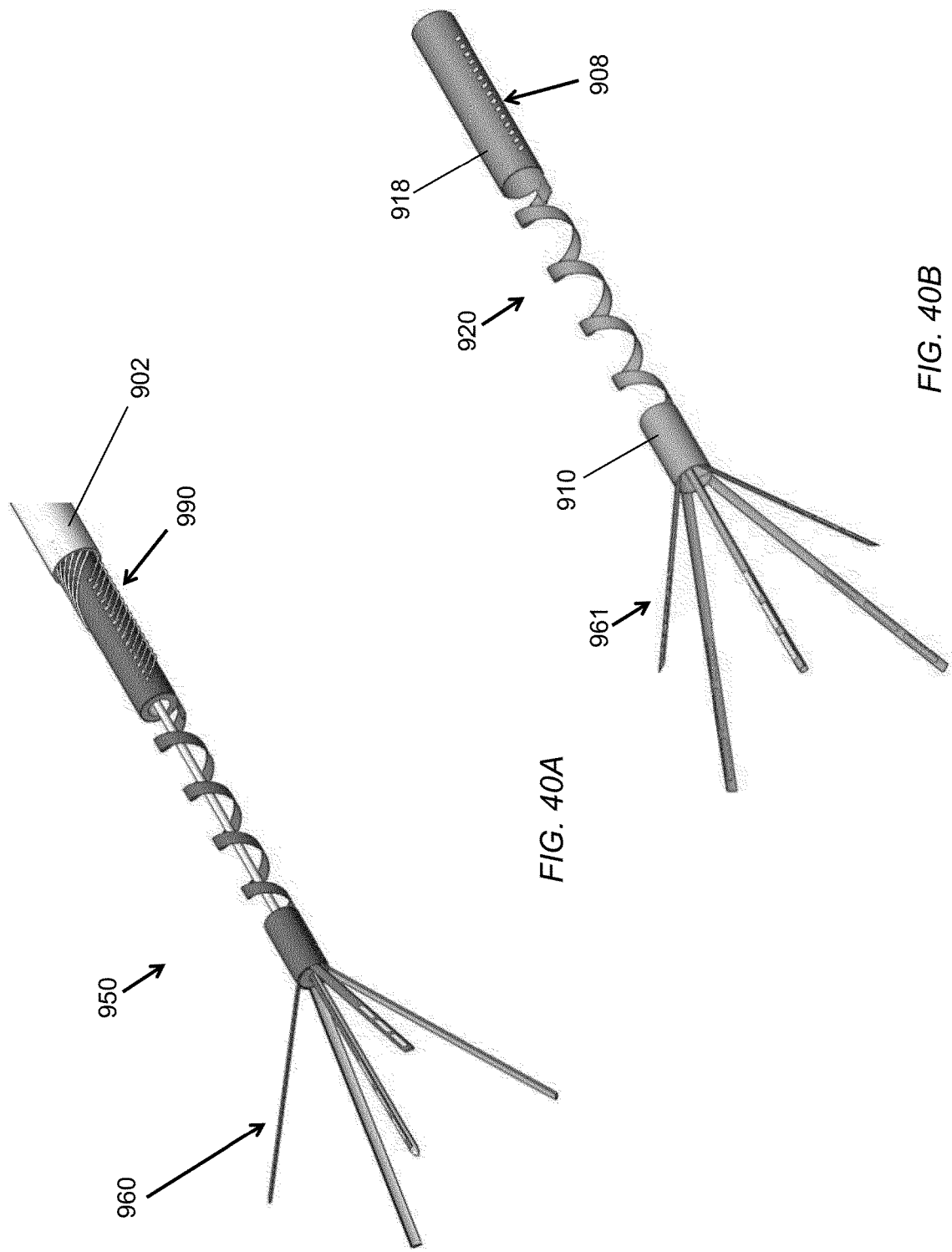
FIG. 40A is a perspective view of an alternative embodiment of FIG. 1 where the microelectronic component is not required.
FIG. 40B is a perspective view of the microelectrode array film required in the assembly of the alternative embodiment of FIG. 40A.

In some embodiments it is advantageous to not require a microelectronic element 300. This may be the case when using the embodiment in a stimulation mode only, or when using low numbers of stimulation sites. FIG. 40A is a perspective view of an alternative embodiment where five protruding shafts 960 are connected directly to the fifteen electrical lead wires 990. The distal microelectrode assembly 950 is therefore in direct electrical communication with the proximal electrical contacts.

FIG. 40B is a perspective view of the microelectrode array film 920 required in the assembly of the alternative embodiment shown in FIG. 40A. In comparison to previous embodiments, it does not have a microelectronic component platform but instead the microelectrodes are electrically connected directly to the lead wire contact pads 908.

In some embodiments it is advantageous to not require that the protruding shafts be rigid, and therefore they do not need to be supported. This may be the case when using the embodiment in delicate tissues. FIG. 40C is a perspective view of an alternative embodiment where five protruding shafts 1060 are not supported by a rigid member, but only consist of the microelectrode array film.

FIG. 40D is a detail perspective view of the internal assembly 1020 of the alternative embodiment shown in FIG. 40C. In comparison to previous embodiments, it does not require a microelectronic component platform but instead the microelectrodes are electrically connected directly to the lead wire contact pads 1008. Furthermore, in comparison to previous embodiments, it does not require a rigid protruding shaft support, but this has been replaced by a cylindrical support 1080. In the present embodiment ten lead wires connect directly to ten microelectrode elements where each flexible shaft 1061 incorporates two microelectrode elements 1065.

Microelectronic Elements

Figure 41:
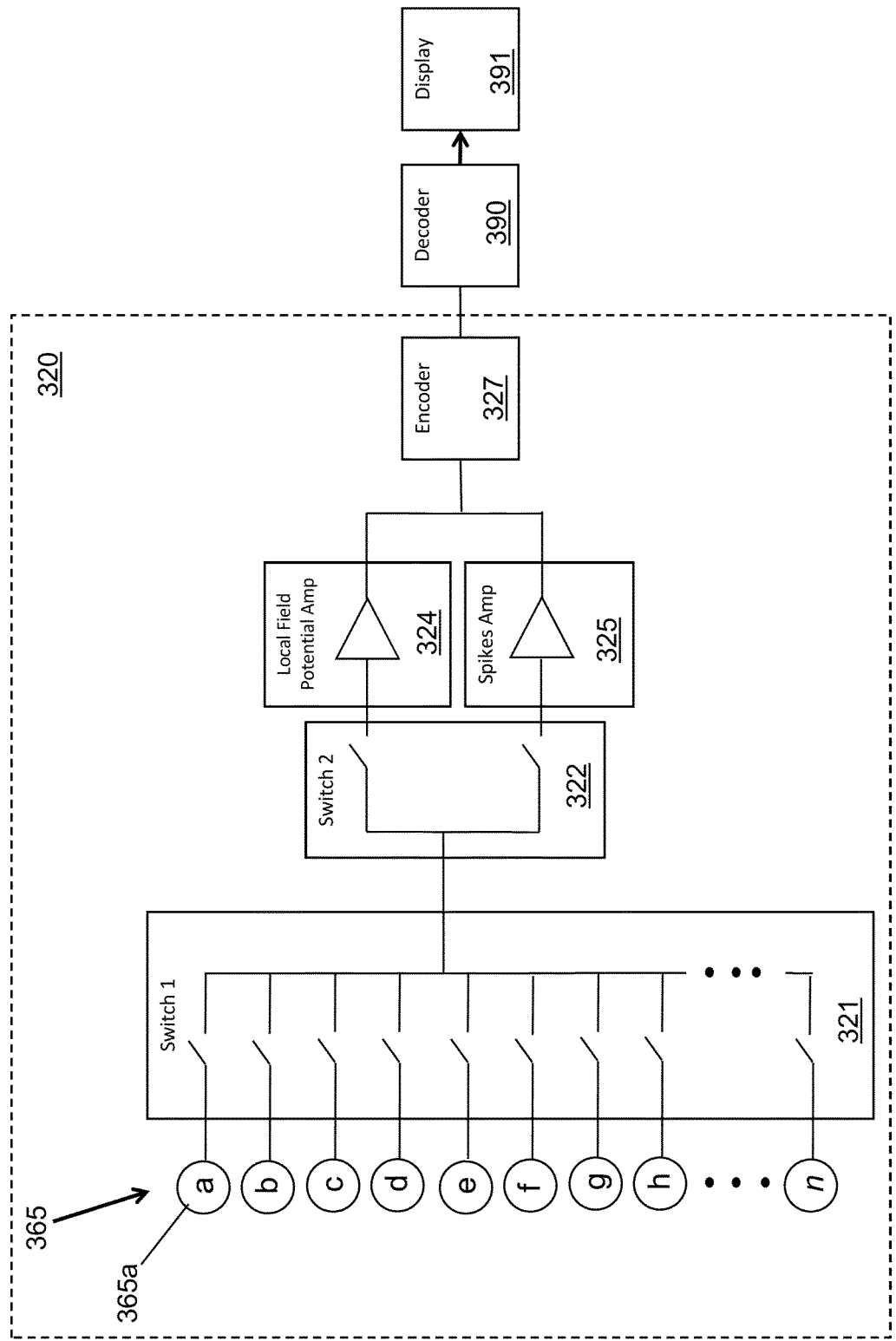
FIG. 41 is a schematic of a neural recording microelectronic circuit.

When the embodiment is in used only for neural recording, the microelectronic element 300 may be configured to only collect electrophysiologically recorded data. FIG. 41 demonstrates a schematic of an electronic circuit that could be implemented within microelectronic element 300. Microelectrode elements 365 are in contact with the neurological tissue. Microelectrode elements 365 are lettered a through n, with dots in between to describe a finite number of possible microelectrode elements 365. Generally there is at least one microelectrode element 365, and in the present embodiment fifteen are required. Electrophysiological signals depolarize microelectrode elements 365 and this signal can be captured by the neural recording microelectronic element 320. The microelectrode element 365 chosen to perform the recording can be selected using switchbox 321. The signal is then routed to switchbox 322, which can chosen to either amplify local field potentials using amplifier 324, or spikes using spike amplifier 325. The signal may then be encoded for transmission to the distal end of the microelectrode lead assembly 100. Connected to the distal end should be a decoder 390, and a display, or data capture device, 391. In some embodiments the circuit can be implemented for each microelectrode element 365. Generally, the frequency bandwidth required for the recording is low enough that all microelectrode elements 365 can time-share the same amplification circuit, whilst display 391 can report the recordings simultaneously.

Figure 42:
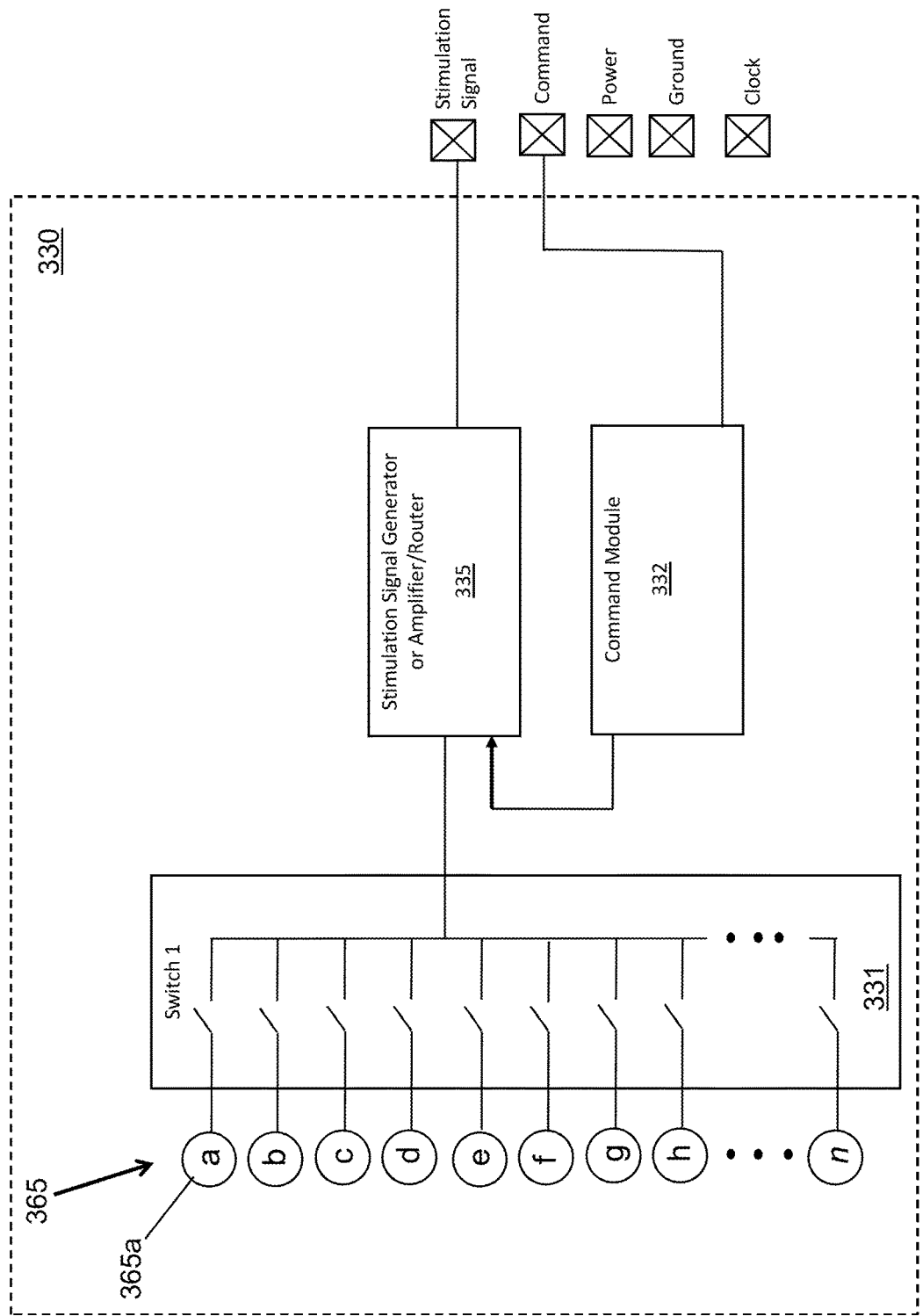
FIG. 42 is a schematic of a neural stimulation microelectronic circuit.

When the embodiment is in used only for neural stimulation, the microelectronic element 300 may be configured to only generate, or alternatively route, stimulation signals. FIG. 42 demonstrates a schematic of an electronic circuit that could be implemented within microelectronic element 300. Microelectrode elements 365 are in contact with the neurological tissue. Stimulation signals are used to stimulate or inhibit neuronal activity and the microelectronic circuit 330 can perform the generation, or routing, of stimulation signals. The microelectrode element 365 chosen to apply the stimulation signal can selected using switchbox 331. In some embodiments, several switches are chosen in order to apply the same signal to several microelectrode elements 365. In some embodiments, several unique signals are generated, or routed, and applied to at least one microelectrode element 365. If the stimulation signal is generated outside of the microelectronic element 300, the signal can be conditioned, and if necessary amplified, using signal conditioner 335. A dedicated lead wire on microelectrode lead assembly 100 can be reserved for this purpose. Additionally, dedicated lead wires on microelectrode lead assembly 100 can be reserved for supplying power to the microelectronic element 330, clock signals, and ground, and command signals.

Figure 43:
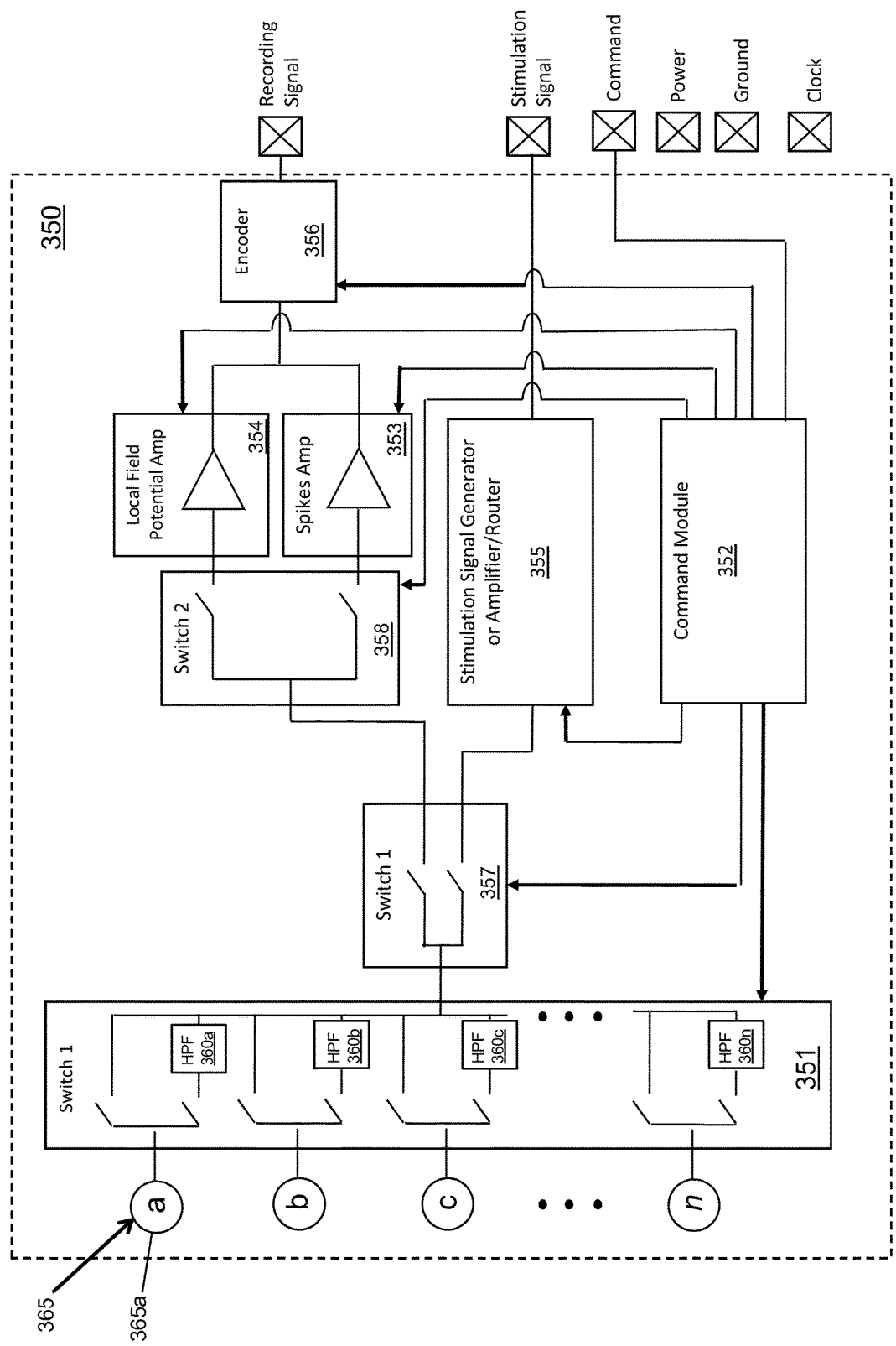
FIG. 43 is a schematic of a combined neural recording and stimulation microelectronic circuit.

In some embodiments the operator wishes to record and stimulate with the same microelectrode elements. To perform this method microelectronic element 300 may be implemented with both recording and stimulation functions. FIG. 43 demonstrates a schematic of an electronic circuit that could be implemented within microelectronic element 300. Microelectrode elements 365 are in contact with the neurological tissue. Electrophysiological signals depolarize microelectrode elements 365 and this signal can be captured by the neural recording and stimulation microelectronic element 350. The microelectrode element 365 chosen to perform the recording can be selected using switchbox 351, and switch box 357 can be selected to the recording state. The signal is then routed to switchbox 358, which can chosen to either amplify local field potentials using amplifier 354, or spikes using spike amplifier 353. The signal may then be encoded for transmission to the distal end of the microelectrode lead assembly 100 using encoder 356.

Stimulation signals are used to stimulate or inhibit neuronal activity and the neuronal recording and stimulation microelectronic circuit 350 can perform the generation, or routing, of stimulation signals. The microelectrode element 365 chosen to apply the stimulation signal can be selected using switchbox 351. In some embodiments, several switches are chosen in order to apply the same signal to several microelectrode elements 365. Additionally, switchbox 357 can be in the stimulation state. In some embodiments, several unique signals are generated, or routed, and applied to at least one microelectrode element 365. If the stimulation signal is generated outside of the microelectronic element 300, the signal can be conditioned, and if necessary amplified, using signal conditioner 355. A dedicated lead wire on microelectrode lead assembly 100 can be reserved for this purpose. Additionally, some embodiments may include high-pass filters 360, of which each filter is dedicated to an individual microelectrode element 365, or shared between several microelectrode elements 365. These high-pass filters 360 may be used in order to tune the stimulation signal to the peak resistance frequency of the microelectrode element 365.

Additionally, dedicated lead wires on microelectrode lead assembly 100 can be reserved for supplying power to the neural recording and stimulation microelectronic element 350, clock signals, and ground, and command signals, recorded signals, and stimulation signals.

Electrical Impedance Tomography

Figure 44:
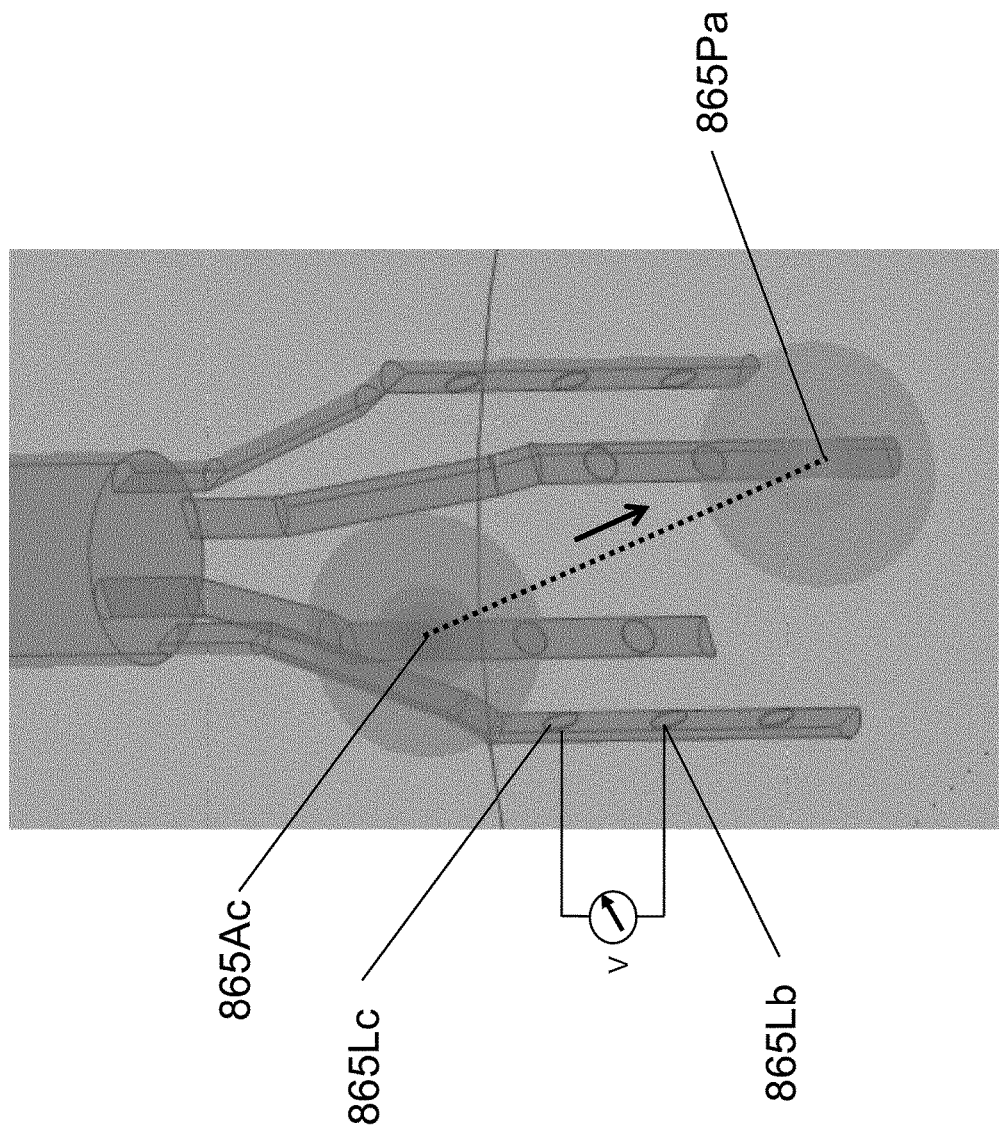
FIG. 44 demonstrates the Electrical Impedance Tomography method described herein.

FIG. 44 demonstrate how Electrical Impedance Tomography may be performed using the devices described. First, an oscillating current is passed between two microelectrode elements 865Ac and 865Pa. The current oscillation may be of a frequency of 1 Hz-10 MHz with a preference of 1 kHz-100 KHz. Additionally, the current oscillation may include other oscillation frequencies. Subsequently, an electric potential is detected between two other microelectrode elements 865Lc and 865L. Alternatively, the electrode potential can be detected at the site of the microelectrode elements that generated and collected the current. This potential gives an indication of the electrical properties of the imaged tissue. Source and detection electrode are alternated, both in 2D space, and 3D space to generate a volumetric and/or tomographic image of the volume contained within the prongs. The signals emanating and detected at the electrodes sites can change in amplitude, frequency, and other characteristics in order to image different tissue properties such as conductivity, permittivity, conductivity direction and/or anisotropy. From this electrical data an understanding of the tissue architecture can be obtained such as location, direction and type of neural fibers, delineation of different tissue types such as grey matter, white matter, and aqueducts, are but a few examples. The image is then reported to the clinician, additionally it can be fitted to known anatomical data in order to provide a first approximation to the device location. Electrode geometries on the prongs can vary, including a single linear array of electrodes, or electrodes that are side-by-side (not shown).

CONCLUSION

Various embodiments of micro-fabricated neurostimulation devices have been described herein. These embodiments are giving by way of example and are not intended to limit the scope of the present invention. It should be appreciated, moreover, that the various features of the embodiments that have been described may be combined in various ways to produce numerous additional embodiments. Moreover, while various materials, dimensions, shapes, implantation locations, etc. have been described for use with disclosed embodiments, others besides those disclosed may be utilized without exceeding the scope of the invention.

Although some devices described herein are identified as either acute or chronic, it is understood that the device may be used acutely, or chronically. They may be implanted for such periods, such as during a surgery, and then removed. They may implanted for extended periods, or even indefinitely. Similarly, any devices described herein as being chronic, it is understood that such devices may also be used acutely.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims.

The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

One or more or any part thereof of the techniques described herein can be implemented in computer hardware or software, or a combination of both. The methods can be implemented in computer programs using standard programming techniques following the method and figures described herein. Program code is applied to input data to perform the functions described herein and generate output information. The output information is applied to one or more output devices such as a display monitor. Each program may be implemented in a high level procedural or object oriented programming language to communicate with a computer system. However, the programs can be implemented in assembly or machine language, if desired. In any case, the language can be a compiled or interpreted language. Moreover, the program can run on dedicated integrated circuits preprogrammed for that purpose.

Each such computer program is preferably stored on a storage medium or device (e.g., ROM or magnetic diskette) readable by a general or special purpose programmable computer, for configuring and operating the computer when the storage media or device is read by the computer to perform the procedures described herein. The computer program can also reside in cache or main memory during program execution. The analysis, preprocessing, and other methods described herein can also be implemented as a computer-readable storage medium, configured with a computer program, where the storage medium so configured causes a computer to operate in a specific and predefined manner to perform the functions described herein. In some embodiments, the computer readable media is tangible and substantially non-transitory in nature, e.g., such that the recorded information is recorded in a form other than solely as a propagating signal.

In some embodiments, a program product may include a signal bearing medium. The signal bearing medium may include one or more instructions that, when executed by, for example, a processor, may provide the functionality described above. In some implementations, signal bearing medium may encompass a computer-readable medium, such as, but not limited to, a hard disk drive, a Compact Disc (CD), a Digital Video Disk (DVD), a digital tape, memory, etc. In some implementations, the signal bearing medium may encompass a recordable medium, such as, but not limited to, memory, read/write (R/W) CDs, R/W DVDs, etc. In some implementations, signal bearing medium may encompass a communications medium such as, but not limited to, a digital and/or an analog communication medium (e.g., a fiber optic cable, a waveguide, a wired communications link, a wireless communication link, etc.). Thus, for example, the program product may be conveyed by an RF signal bearing medium, where the signal bearing medium is conveyed by a wireless communications medium (e.g., a wireless communications medium conforming with the IEEE 802.11 standard).

It is to be understood that any of the signals and signal processing techniques may be digital or analog in nature, or combinations thereof.

While certain embodiments of this invention have been particularly shown and described with references to preferred embodiments thereof, it will be understood by those skilled in the art that various changes in form and details may be made therein without departing from the scope of the invention encompassed by the appended claims.

What is claimed is:

1. An implantable neurological probe, comprising:
    an elongated shaft having a distal end and an internal lumen;
    a support cylinder slidingly disposed in only a distal portion of the internal lumen;
    a plurality of shafts coupled to the support cylinder and arranged for selective extension from the distal end of the elongated shaft;
    a microelectrode array film comprising a first portion coupled toward the distal end of the elongated shaft and a second portion coupled with the support cylinder, the microelectrode array film comprising a plurality of microelectrode film shafts disposed on each of the plurality of shafts, each of the plurality of microelectrode film shafts comprising a plurality of microelectrode elements, the microelectrode array film further comprising:
        a helical ribbon cable that separates the first portion of the microelectrode array film from the second portion of the microelectrode array film, the helical ribbon cable couples each of the plurality of microelectrode elements with a respective proximal contact pad;
        a planar substrate having an insulative layer; and
        a plurality of conductive traces disposed on the insulative layer; and
    a stylet removably disposed in the internal lumen and configured to contact the support cylinder to selectively extend the plurality of shafts during implantation.

2. The implantable neurological probe of claim 1, comprising a push-pull rod which comprises a pull wire and the stylet.

3. The implantable neurological probe of claim 1, wherein the elongated shaft is configured for insertion into a human body using an accepted procedure for insertion of deep brain stimulation leads.

4. The implantable neurological probe of claim 1, wherein a diameter of the elongated shaft is between 1 mm and 3 mm.

5. The implantable neurological probe of claim 1, wherein at least one of the plurality of microelectrode elements is a stimulating electrode and at least one of the plurality of microelectrode elements is a detecting electrode.

6. The implantable neurological probe of claim 1, wherein at least one of the plurality of microelectrodes elements is both a stimulating electrode and a detecting electrode.

7. The implantable neurological probe of claim 1, wherein each of the plurality of microelectrode elements is disposed on the insulative layer.

8. The implantable neurological probe of claim 7, wherein the microelectrode array film is formable into a cylindrical assembly.

9. The implantable neurological probe of claim 8, wherein each of the plurality of shafts can be formed to bend radially from a longitudinal axis of the elongated shaft.

10. The implantable neurological probe of claim 8, where one of the plurality of shafts extends and is centered along a longitudinal axis of the elongated shaft.

11. The implantable neurological probe of claim 9, where each of the plurality of microelectrode film shafts are stiffened by one of the plurality of shafts.

12. An implantable neurological probe, comprising: an elongated shaft having a distal end and an internal lumen; a plurality of shafts coupled to a support cylinder, the plurality of shafts arranged for selective extension from the distal end of the elongated shaft; and a microelectrode array film comprising a first portion coupled toward the distal end of the elongated shaft and a second portion coupled with the support cylinder, the microelectrode array film comprising a plurality of microelectrode film shafts disposed on each of the plurality of shafts, each of the plurality of microelectrode film shafts comprising a plurality of microelectrode elements, the microelectrode array film further comprising: a helical ribbon cable separating the first portion of the microelectrode array film from the second portion of the microelectrode array film, the helical ribbon cable coupling each of the plurality of microelectrode elements with a respective proximal contact pad; a planar substrate having an insulative layer; and a plurality of conductive traces disposed on the insulative layer, wherein the plurality of shafts define a substantially cylindrical volume when fully extended.

13. The implantable neurological probe of claim 12, wherein the elongated shaft is configured for insertion into a human body using an accepted procedure for insertion of deep brain stimulation leads.

14. The implantable neurological probe of claim 12, wherein a diameter of the elongated shaft is between 1 mm and 3 mm.

15. The implantable neurological probe of claim 12, wherein at least one of the plurality of microelectrode elements is a stimulating electrode and at least one of the plurality of microelectrode elements is a detecting electrode.

16. The implantable neurological probe of claim 12, wherein at least one of the plurality of microelectrodes elements is both a stimulating electrode and a detecting electrode.

17. The implantable neurological probe of claim 12, wherein each of the plurality of microelectrode elements is disposed on the insulative layer.

18. The implantable neurological probe of claim 17, wherein the microelectrode array film is formable into a cylindrical assembly.

19. The implantable neurological probe of claim 18, where at least one of the plurality of shafts can be formed to bend radially from a longitudinal axis of the elongated shaft.

20. The implantable neurological probe of claim 18, where one of the plurality of shafts is centered along a longitudinal axis of the elongated shaft.

21. The implantable neurological probe of claim 18, where each of the plurality of microelectrode shafts are stiffened by one of the plurality of shafts.

22. A method of finding a neurological target, comprising:
  implanting a neurological probe within a vicinity of a neurological target site, the neurological probe comprising:
    an elongated shaft having a distal end and an internal lumen;
    a support cylinder slidingly disposed in only a distal portion of the internal lumen;
    a plurality of shafts coupled to the support cylinder and arranged for selective extension from the distal end of the elongated shaft;
    a microelectrode array film comprising a first portion coupled toward the distal end of the elongated shaft and a second portion coupled with the support cylinder, the microelectrode array film comprising a plurality of microelectrode film shafts disposed on each of the plurality of shafts, each of the plurality of microelectrode film shafts comprising a plurality of microelectrode elements, the microelectrode array film further comprising:
      a helical ribbon cable separating the first portion of the microelectrode array film from the second portion of the microelectrode array film, the helical ribbon cable coupling each of the plurality of microelectrode elements with a respective proximal contact pad;
      a planar substrate having an insulative layer; and
      a plurality of conductive traces disposed on the insulative layer; and
    a stylet removably disposed in the internal lumen and configured to contact the support cylinder to selectively extend the plurality of shafts during implantation;
  retracting the plurality of shafts within the internal lumen before surgical implantation;
  extending the plurality of shafts in the vicinity of the neurological target site following implantation;
  recording electrophysiological signals from the neurological target site using at least one of the plurality of microelectrode elements; and
  stimulating the neurological target using at least one of the plurality of microelectrode elements.

23. The method of claim 22, further comprising:
  after the acts of recording and stimulating, retracting the plurality of shafts within the internal lumen and removing the neurological probe from a subject.

24. The method of claim 22, wherein the plurality of shafts are retracted using a pull wire.

25. The method of claim 22, wherein the plurality of shafts are extended using the stylet.

26. The method of claim 22, wherein the neurological probe comprises a push-pull rod which comprises a pull wire and the stylet.

27. The method of claim 22, wherein the act of recording neurophysiological signals comprises recording neural activity detected by at least one of the plurality of microelectrode elements and repositioning the distal end of the elongated shaft as required, until the recorded activity is indicative of the distal end of the elongated probe shaft being located sufficiently at the neurological target site.

28. The method of claim 22, comprising:
  stimulating neural activity at a stimulation site by applying electrical signals to at least one of the plurality of microelectrode elements;
  performing a clinical evaluation of the efficacy on the stimulation site in a patient, and
  repositioning the distal end of the elongated shaft as required, until the patient's response is indicative of the distal end of the elongated shaft being located sufficiently at the neurological target site.

29. The method of claim 22, comprising:
  inhibiting neural activity by applying electrical signals to at least one of the plurality of microelectrode,
  performing a clinical evaluation of the efficacy on the inhibition site in a patient, and
  repositioning the distal end of elongated shaft as required, until the patient's response is indicative of the distal end of the elongated shaft being located sufficiently at the neurological target site.

30. A method of finding a neurological target, comprising:
  implanting a neurological probe within a vicinity of a neurological target site, the neurological probe comprising:
    an elongated shaft having a distal end and an internal lumen;
    a support cylinder slidingly disposed in only a distal portion of the internal lumen;
    a plurality of shafts coupled to the support cylinder and arranged for selective extension from the distal end of the elongated shaft;
    a microelectrode array film comprising a first portion coupled toward the distal end of the elongated shaft and a second portion coupled with the support cylinder, the microelectrode array film comprising a plurality of microelectrode film shafts disposed on each of the plurality of shafts, each of the plurality of microelectrode film shafts comprising a plurality of microelectrode elements, the microelectrode array film further comprising:
      a helical ribbon cable separating the first portion of the microelectrode array film from the second portion of the microelectrode array film, the helical ribbon cable coupling each of the plurality of microelectrode elements with a respective proximal contact pad;
      a planar substrate having an insulative layer; and
      a plurality of conductive traces disposed on the insulative layer; and
    a stylet removably disposed in the internal lumen and configured to contact the support cylinder to selectively extend the plurality of shafts during implantation;
  retracting the plurality of shafts within the internal lumen before surgical implantation;
  expanding the plurality of shafts in the vicinity of the neurological target site following implantation;
  applying an oscillating electric current between at least two of the plurality of microelectrode elements; and
  detecting an electric voltage between at least two of the plurality of microelectrode elements.

31. The method of claim 30, further comprising:
  after the act of detecting, retracting the plurality of shafts within the internal lumen and removing the neurological probe from a subject.

32. The method of claim 30, comprising imaging the electrical characteristics of the volume of neurological tissue between the plurality of shafts based on the applied oscillating electric current and the detected electric voltage.

33. The method of claim 30, wherein the neurological probe comprises a push-pull rod which comprises a pull wire and the stylet.

34. A method of finding a neurological target, comprising:
  implanting a neurological probe within a vicinity of a neurological target site, the neurological probe comprising:

an elongated shaft having a distal end and an internal lumen; a plurality of shafts coupled to a support cylinder, the plurality of shafts arranged for selective extension from the distal end of the elongated shaft; and a microelectrode array film comprising a first portion coupled toward the distal end of the elongated shaft and a second portion coupled with the support cylinder, the microelectrode array film comprising a plurality of microelectrode film shafts disposed on each of the plurality of shafts, each of the plurality of microelectrode film shafts comprising a plurality of microelectrode elements, the microelectrode array film further comprising: a helical ribbon cable separating the first portion of the microelectrode array film from the second portion of the microelectrode array film, the helical ribbon cable coupling each of the plurality of microelectrode elements with a respective proximal contact pad; a planar substrate having an insulative layer; and a plurality of conductive traces disposed on the insulative layer; and wherein the plurality of shafts define a substantially cylindrical volume when fully extended; retracting the plurality of shafts within the internal lumen before surgical implantation; extending the plurality of shafts in the vicinity of the neurological target site following implantation; recording electrophysiological signals from the neurological target site using at least one of the plurality of microelectrode elements; and stimulating the neurological target using at least one of the plurality of microelectrode elements.

35. The method of claim 34, wherein the protruding shafts are retracted using a pull wire.

36. The method of claim 35, wherein the plurality of shafts are extended using a stylet.

37. The method of claim 36, wherein the neurological probe comprises a push-pull rod which comprises the pull wire and the stylet.

38. The method of claim 34, wherein the act of recording neurophysiological signals comprises recording neural activity detected by at least one of the plurality of microelectrode elements and repositioning the distal end of the elongated shaft as required, until the recorded activity is indicative of the distal end of the elongated probe shaft being located sufficiently at the neurological target site.

39. The method of claim 34, further comprising:
after the acts of recording and stimulating, retracting the plurality of shafts within the internal lumen and removing the neurological probe from a subject.

40. The method of claim 34, comprising:
stimulating neural activity at a stimulation site by applying electrical signals to at least one of the plurality of microelectrode elements;
performing a clinical evaluation of the efficacy on the stimulation site in a patient, and
repositioning the distal end of the elongated shaft as required, until the patient's response is indicative of the distal end of the elongated shaft being located sufficiently at the neurological target site.

41. The method of claim 34, comprising:
inhibiting neural activity by applying electrical signals to at least one of the plurality of microelectrode elements;
performing a clinical evaluation of the efficacy on the inhibition site in a patient, and
repositioning the distal end of elongated shaft as required, until the patient's response is indicative of the distal end of the elongated shaft being located sufficiently at the neurological target site.

42. A method of finding a neurological target, comprising:
implanting a neurological probe within a vicinity of a neurological target site, the neurological probe comprising:
an elongated shaft having a distal end and an internal lumen;
a plurality of shafts coupled to a support cylinder, the plurality of shafts arranged for selective extension from the distal end of the elongated shaft; and
a microelectrode array film comprising a first portion coupled toward the distal end of the elongated shaft and a second portion coupled with the support cylinder, the microelectrode array film comprising a plurality of microelectrode film shafts disposed on each of the plurality of shafts, each of the plurality of microelectrode film shafts comprising a plurality of microelectrode elements, the microelectrode array film further comprising:
a helical ribbon cable separating the first portion of the microelectrode array film from the second portion of the microelectrode array film, the helical ribbon cable coupling each of the plurality of microelectrode elements with a respective proximal contact pad;
a planar substrate having an insulative layer; and
a plurality of conductive traces disposed on the insulative layer,
wherein the plurality of shafts define a substantially cylindrical volume when fully extended;
retracting the plurality of shafts within the internal lumen before surgical implantation;
extending the plurality of shafts in the vicinity of the neurological target site following implantation;
applying an oscillating electric current between at least two of the plurality of microelectrode elements on at least one of the plurality of shafts;
detecting an electric voltage between at least two of the plurality of microelectrode elements on at least one of the plurality of shafts.

43. The method of claim 42, comprising imaging the electrical characteristics of the volume of neurological tissue between the plurality of shafts based on the applied oscillating electric current and the detected electric voltage.

44. The method of claim 32, further comprising:
after the act of detecting, retracting the plurality of shafts within the internal lumen and removing the neurological probe from a subject.

* * * * *